(12) United States Patent
Parhami et al.

(10) Patent No.: US 9,526,737 B2
(45) Date of Patent: *Dec. 27, 2016

(54) OXYSTEROLS FOR ACTIVATION OF HEDGEHOG SIGNALING, OSTEOINDUCTION, ANTIADIPOGENESIS, AND WNT SIGNALING

(75) Inventors: Farhad Parhami, Los Angeles, CA (US); Michael E. Jung, Los Angeles, CA (US); Khanhlinh Nguyen, Los Angeles, CA (US); Dongwon Yoo, Los Angeles, CA (US); Woo-Kyun Kim, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 773 days.

This patent is subject to a terminal disclaimer.

(21) Appl. No.: 12/745,888

(22) PCT Filed: Dec. 3, 2008

(86) PCT No.: PCT/US2008/013319
§ 371 (c)(1),
(2), (4) Date: Sep. 20, 2010

(87) PCT Pub. No.: WO2009/073186
PCT Pub. Date: Jun. 11, 2009

(65) Prior Publication Data
US 2011/0008297 A1 Jan. 13, 2011

Related U.S. Application Data

(60) Provisional application No. 60/996,729, filed on Dec. 3, 2007.

(51) Int. Cl.
*A01N 63/00* (2006.01)
*A61K 31/575* (2006.01)
*A61K 45/06* (2006.01)

(52) U.S. Cl.
CPC ............ *A61K 31/575* (2013.01); *A61K 45/06* (2013.01)

(58) Field of Classification Search
CPC ... A61K 31/575; A61K 45/06; A61K 2300/00
USPC ........ 424/93.7, 676; 514/182, 11.8, 8.6, 8.8, 514/8.5, 171, 8.9; 435/375, 377; 552/546, 556; 540/120
See application file for complete search history.

(56) References Cited

U.S. PATENT DOCUMENTS

| | | |
|---|---|---|
| 3,309,387 A | 3/1967 | Furst et al. |
| 3,887,545 A | 6/1975 | Iacobelli et al. |
| 4,183,852 A | 1/1980 | Kaiser |
| 4,264,512 A | 4/1981 | Okamura et al. |
| 4,559,157 A | 12/1985 | Smith et al. |
| 4,608,392 A | 8/1986 | Jacquet et al. |
| 4,743,597 A | 5/1988 | Javitt et al. |
| 4,820,508 A | 4/1989 | Wortzman |
| 4,938,949 A | 7/1990 | Borch et al. |
| 4,961,922 A | 10/1990 | Shroot et al. |
| 4,992,478 A | 2/1991 | Geria |
| 5,166,320 A | 11/1992 | Wu et al. |
| 5,183,815 A | 2/1993 | Saari et al. |
| 5,219,740 A | 6/1993 | Miller et al. |
| 5,288,641 A | 2/1994 | Roizman |
| 5,723,455 A | 3/1998 | Tanabe et al. |
| 5,840,752 A | 11/1998 | Henry et al. |
| 5,929,062 A | 7/1999 | Haines |
| 6,017,904 A | 1/2000 | Reed et al. |
| 6,080,779 A | 6/2000 | Gasper et al. |
| 6,177,420 B1 | 1/2001 | Leemhuis et al. |
| 6,184,215 B1 | 2/2001 | Elias et al. |
| 6,316,503 B1 | 11/2001 | Li et al. |
| 6,420,353 B1 | 7/2002 | Lathe et al. |
| 6,436,917 B1 | 8/2002 | Droescher et al. |
| 6,518,262 B1 | 2/2003 | Leysen et al. |
| 6,586,189 B2 | 7/2003 | Forman |
| 6,863,900 B2 | 3/2005 | Kadiyala et al. |
| 6,893,830 B1 | 5/2005 | Janowski et al. |
| 6,906,069 B1 | 6/2005 | Li et al. |
| 7,060,450 B1 | 6/2006 | Tabin et al. |
| 7,196,220 B2 | 3/2007 | Pierce, Jr. et al. |
| 7,427,610 B2 | 9/2008 | Hillisch et al. |
| 8,071,575 B2 | 12/2011 | Pierce, Jr. et al. |
| 2003/0153541 A1 | 8/2003 | Dudley et al. |
| 2004/0072806 A1 | 4/2004 | Yao et al. |
| 2004/0077613 A1 | 4/2004 | Bamberg et al. |
| 2004/0176423 A1 | 9/2004 | Paralkar |
| 2004/0235739 A1 | 11/2004 | Mahanthappa |
| 2005/0095677 A1 | 5/2005 | Liu et al. |
| 2006/0251735 A1 | 11/2006 | Parhami |
| 2006/0270645 A1 | 11/2006 | Parhami |

(Continued)

FOREIGN PATENT DOCUMENTS

DE 10204042822 3/2006
EP 337890 A1 10/1989

(Continued)

OTHER PUBLICATIONS

Nagahisa et al (J. Biol. Chem., 1983, 258, 6721-6723).*
Burstein et al (Steroids, 1969, 399-412).*
RN102814-21-1(available Jun. 21, 1986), corresponding to (5S)-5-((3S,8S,9S,10R,13S,14S,17S)-3-hydroxy-10,13-dimethyl-2,3,4,7,8,9,10,11,12,13,14,15,16,17-tetradecahydro-1H-cyclopenta[a]phenanthren-17-yl)-2-methylhexane-1,5-diol.*
RN135873-40-4( available Aug. 30, 1991), corresponding to (5-phenylpentyl)magnesium bromide.*

(Continued)

*Primary Examiner* — Jeffrey S Lundgren
*Assistant Examiner* — Ibrahim D Bori
(74) *Attorney, Agent, or Firm* — Mintz Levin Cohn Ferris Glovsky and Popeo, P.C.

(57) ABSTRACT

Synthetic oxysterols can be made and can be used for the treatment of bone disorders, obesity, cardiovascular disorders, and neurological disorders.

14 Claims, 26 Drawing Sheets

(56) References Cited

U.S. PATENT DOCUMENTS

| | | |
|---|---|---|
| 2008/0070883 A1 | 3/2008 | Nagpal |
| 2009/0202661 A1 | 8/2009 | Kirkpatrick |
| 2009/0220562 A1 | 9/2009 | Parhami |
| 2010/0012030 A1 | 1/2010 | Todd et al. |
| 2010/0034781 A1 | 2/2010 | Parhami et al. |
| 2010/0048944 A1 | 2/2010 | Parhami |
| 2010/0105645 A1 | 4/2010 | Parhami et al. |
| 2011/0008297 A1 | 1/2011 | Parhami et al. |
| 2012/0309730 A1 | 12/2012 | Parhami et al. |

FOREIGN PATENT DOCUMENTS

| | | |
|---|---|---|
| EP | 0 415 731 A2 | 3/1991 |
| GB | 869007 A | 5/1961 |
| GB | 2 320 190 A | 6/1998 |
| JP | S51-11114 B1 | 4/1976 |
| JP | 2000-508911 A | 7/2000 |
| JP | 2000-511404 A | 9/2000 |
| JP | 2002-506030 A | 2/2002 |
| JP | 2002-506817 A | 3/2002 |
| WO | WO-90/07936 A1 | 7/1990 |
| WO | WO-91/02805 A2 | 3/1991 |
| WO | WO-93/09191 A1 | 5/1993 |
| WO | WO-93/10218 A1 | 5/1993 |
| WO | WO-93/11230 A1 | 6/1993 |
| WO | WO-93/25234 A1 | 12/1993 |
| WO | WO-93/25698 A1 | 12/1993 |
| WO | WO-94/03622 A1 | 2/1994 |
| WO | WO-94/26914 A1 | 11/1994 |
| WO | WO-95/13365 A1 | 5/1995 |
| WO | WO-97/40137 A1 | 10/1997 |
| WO | WO-99/45923 A1 | 9/1999 |
| WO | WO-99/47136 A1 | 9/1999 |
| WO | WO-00/54759 A2 | 9/2000 |
| WO | WO-01/15676 A2 | 3/2001 |
| WO | WO-02/080952 A2 | 10/2002 |
| WO | WO-2004/019884 A2 | 3/2004 |
| WO | WO-2005/020928 A2 | 3/2005 |
| WO | WO-2005/028616 A2 | 3/2005 |
| WO | WO-2005/123757 A1 | 12/2005 |
| WO | WO-2006/012902 A2 | 2/2006 |
| WO | WO-2006/110490 A2 | 10/2006 |
| WO | WO-2007/028101 A2 | 3/2007 |
| WO | WO-2007/098281 A2 | 8/2007 |
| WO | WO-2008/011071 A2 | 1/2008 |
| WO | WO-2008/041003 A2 | 4/2008 |
| WO | WO-2008/082520 A2 | 7/2008 |
| WO | WO-2008/115469 A2 | 9/2008 |
| WO | WO-2009/073186 A1 | 6/2009 |
| WO | WO-2011/006087 A1 | 1/2011 |
| WO | WO-2011/103175 A2 | 8/2011 |
| WO | WO-2012/024581 A2 | 2/2012 |
| WO | WO-2012/024583 A2 | 2/2012 |
| WO | WO-2012/024584 A2 | 2/2012 |
| WO | WO-2013/169397 A1 | 11/2013 |
| WO | WO-2013/169399 A1 | 11/2013 |
| ZA | 6808005 | 6/1969 |

OTHER PUBLICATIONS

RN72535-09-2( available Nov. 16, 1984), corresponding to (4-methylpent-4-en-1-yl)magnesium bromide.*
Arnsdorf EJ et al.; Tissue Engineering: Part A (15) pp. 1-6 (2009).
Ayukawa, Y. et al., "Local application of statin promotes bone repair through the suppression of osteoclasts and the enhancement of osteoblasts at bone-healing sites in rats," Oral Surgery, Oral Medicine, Oral Pathology, Oral Radiology, and Endodontics, 107(3), pp. 336-342 (2009).
Beckers L. et al., "Disruption of hedgehog signaling in ApoE -/- mice reduces plasma lipid levels, but increases atherosclerosis due to enhanced lipid uptake by macrophages". J Pathol. Aug. 2007;212(4):420-8.
Bunta W. et al., Steroids 2004, 69: 483-493.
Chuu C. et al., "The liver X receptor agonist 10901317 acts as androgen receptor antagonist in human prostate cancer cells". Biochem Biophys Res Commun. Jun. 1, 2007;357(2):341-6. Epub Mar. 28, 2007.
Dwyer J et al., "Oxysterols are novel activators of the hedgehog signaling pathway in pluripotent mesenchymal cells". J Biol Chem 2007, 282: 8956-8968.
Kim, WK et al., "20(S)-hydroxycholesterol inhibits PPARgamma expression and adipogenic differentiation of bone marrow stromal cells through a hedgehog-dependent mechanism," J. Bone Miner Res., 22(11), pp. 1711-1719, (Nov. 2007).
Liu M. et al., "The effect of simvastatin on the differentiation of marrow stromal cells from aging rats," Die Pharmazie 64(1), pp. 43-48 (2009).
Schambony A. et al., "Wnt-5A/Ror2 regulate expression of XPAPC through an alternative noncanonical signaling pathway". Dev Cell. May 2007;12(5):779-92.
Aghaloo et al. (2005) Oxysterols enhance osteoblast differentiation in vitro and bone healing in vivo. J. Bone & Mineral Research. American Society for Bone and Mineral Research (27th Annual Meeting). 20:9, sup. 1.: S361 (Abstract M203).
Aghaloo et al., (2007) Oxysterols enhance osteoblast differentiation in vitro and bone healing in vivo. J Orthop Res. 11:1488-97 (also known as Aghaloo 2006 in press).
Akazawa et al., (2004) The upregulated expression of sonic hedgehog in motor neurons after rat facial nerve axotomy. J Neuroscience 24:7923-7930.
Albrektsson et al., (2001) Osteoinduction, osteoconduction and osseointegration. Eur Spine J. 10:S96-S101.
Almeida et al., (2005) Wnt proteins prevent apoptosis of both uncommitted osteoblast progenitors and differentiated osteoblasts by beta-catenin-dependent and -independent signaling cascades involving Src/ERK and phosphatidylinositol 3-kinase/AKT. J Biol Chem. 16;(280(50):41342-51.
Amantea et al. (2006) Oxysterols are novel activators of hedgehog and Wnt signaling. J Bone Miner Res 21:SI-S156.
Banerjee et al., (1997) Runt homology domain proteins in osteoblast differentiation: AML3/CBFA1 is a major component of a bone-specific complex. J Cell Biochem. 66;(1):1-8.
Bannai et al., (1979) Studies on steroids. Part 37. Synthesis of the four stereoisomers of 20,22-epoxycholesterol. J Chem Soc Perkins Trans, pp. 2116-2120.
Basu et al., (2001) Association between oxidative stress and bone mineral density. Biochem Biophys Res Commun. 288;(1):275-9.
Bennett et al., (2002) Regulation of Wnt signaling during adipogenesis. J Biol Chem. 277;(34): 30998-1004.
Bennett et al., (2005) Regulation of osteoblastogenesis and bone mass by Wnt10b. Proc Natl Acad Sci U S A. 102(9):3324-9.
Bergman et al., (1996) Age-related changes in osteogenic stem cells in mice. J Bone Miner Res 11:568-577.
Bestmann et al., (1979) Synthesis and reaction of diazoacetyl chloride. Angew Chem 91:1012-1013.
Bijlsma et al., (2004) Hedgehog: an unusual signal transducer. BioEssays 26:387-394.
Bijlsma et al., (2006) Hedgehog morphogen in cardiovascular disease. Circulation 114:1985-1991.
Bilezikian et al., (2001) Therapy of male osteoporosis with parathyroid hormone. Calcif Tissue Int 69:248-251.
Bjorkhem et al., (1987) On the possible use of the serum level of 7α-hydroxycholesterol as a marker for incrased activity of the cholesterol 7α-hydroxylase in humans. J Lipid Res 28: 889-894.
Bjorkhem et al., (2002) Oxysterols in human circulation: which role do they play? Curr Opion Lipidol 13:247-253.
Bjorkhem et al., (2002) Oxysterols: friends, foes, or just fellow passengers? Arterioscler Thromb Vasc Biol 22:734-742.
Boguslawski et al., (2000) Activation of osteocalcin transcription involves interaction of protein kinase A- and protein kinase C-dependent pathways. J Biol Chem. 275;(2):999-1006.
Boland et al., (2004) Wnt 3a promotes proliferation and suppresses osteogenic differentiation of adult human mesenchymal stem cells. J Cell Biochem. 93;(6):1210-30.
Braunersreuther et al., (2006) Leukocyte recruitment in atherosclerosis: potential targets for therapeutic approaches? Cell Mol Life Sci 63: 2079-2088.

(56) References Cited

OTHER PUBLICATIONS

Burger et al., (1988) Tetrahedron 44:1141-1152.
Burger et al., (1988), 44, 1141-1152.
Burstein et al.,(1969) A Preliminary Report on the Intermediates in the Conversion in Vitro of Cholesterol to Pregnenolone in Adrenal Preparations. Steroids 14;(2):207-217.
Burstein, et al., (1969) Reactions of 20-Hydroxylated Steroids with Bovine Adrenal Tissue Preparations. Steroids 13;(3):399-412.
Byon et al., (1976) Stereospecific synthesis of the four 20,22-epoxycholesterols and of (Z)-20(22)-Dehydrocholesterol. J Org Chem 41:3716-3722.
Byrd et al., (2004) Hedgehog signaling in murine vasculogenesis and angiogenesis. Trends Cardiovasc Med 14:308-313.
Cadot et al., (2006) Tetrahedron, 62: 4384-4392.
Caplan AI. (1994) The mesengenic process. Bone Repair and Regeneration 21:429-435.
Caplan et al., (2001) Mesenchymal stem cells: building blocks for molecular medicine in the 21st century. Trends Mol Med. (6):259-64. Review.
Chan et al., (2002) Age-related bone loss: old bone, new facts. Gerontology 48:62-71.
Chaudhuri et al., (1969) Stereochemistry of the addition reactions of Grignard reagents to 20-keto steroids. Syntheses of 17α,20α-dihydroxycholesterol. J Org Chem; 34:3759-3766.
Chen et al., (2002) Inhibition of hedgehog signaling by direct binding of cyclopamine to Smoothened. Genes & Develop, 16:2743-2748.
Chen et al., (2002) Age-related osteoporosis in biglycan-deficient mice is related to defects in bone marrow stromal cells. J Bone Miner Res. 17(2):331-40.
Chen et al., (2004) Bone morphogenetic proteins. Growth Factors. 22(4):233-41. Review.
Cheng et al., (1977) Chemistry and Biochemistry of Chinese Drugs. Part 1. Sterol Derivatives Cytotoxic to Hepatoma Cells, Isolated from the Drug Bombyx cum Botryte. J. Chem. Res. (S), v. 9 p. 217.
Choo et al., (1999) Otolaryngology Head Neck Surgery, 120: 84-91.
Chuu et al., (2006) Inhibition of tumor growth and progression of LNCaP prostate cancer cells in athymic mice by androgen and liver X receptor agonist. Cancer Res. 66(13):6482-6.
Clevers H., (2006) Wnt/beta-catenin signaling in development and disease. Cell. 127(3):469-80. Review.
Clément-Lacroix et al., (2005) Lrp5-independent activation of Wnt signaling by lithium chloride increases bone formation and bone mass in mice. Proc Natl Acad Sci U S A. 102(48):17406-11.
Cohen MM., (2003) The hedgehog signaling network. Am J Med Gen 123A:5-28.
Corcoran et al., (2006) Oxysterols stimulate sonic hedgehog and proliferation of medulloblastoma cells. Proceedings of the National Academy of Sciences, 103(22): 8408-8413.
Cummings et al., (2002) Epidemiology and outcomes of osteoporotic fractures. Lancet. 359(9319):1761-7. Review.
Day et al., (2005) Wnt/beta-catenin signaling in mesenchymal progenitors controls osteoblast and chondrocyte differentiation during vertebrate skeletogenesis. Dev Cell. 8(5):739-50.
De La Rosa et al., (1990) Synthetic Commun. 20: 2059-2064.
Debiais et al., (2004) Fibroblast growth factor-2 induces osteoblast survival through a phosphatidylinositol 3-kinase-dependent, -beta-catenin-independent signaling pathway. Exp Cell Res. 297(1):235-46.
Devos et al., (1979) Syntheseis of acyl halides under very mild conditions. J Chem soc Chem Commun, 1180-1181.
Dimmeler et al. (2001) HMG-CoA reductase inhibitors (statins) increase endothelial progenitor cells via the PI 3-kinase/Akt pathway. Journal of Clin Invest. 108:(3): 391-397.
Drew et al., (1987) J of Org. Chem, 52: 4047-4052 (no detailed info found in PubMed).
Ducy et al., (1997) Osf2/Cbfa1: A transcriptional activator of osteoblast differentiation. Cell, 89:747-754.
Ducy P., (2000) Cbfa1: a molecular switch in osteoblast biology. Dev Dyn., 219(4):461-71.

Eastell R., (1998) Treatment of postmenopausal osteoporosis. New Eng J Med, 338(11):736-746.
Edwards et al., (1999) Sterols and isoprenoids: signaling molecules derived from the cholesterol biosynthetic pathway. Annu Rev Biochem 68:157-185.
Edwards et al., (2002) BAREing it all: the adoption of LXR and FXR and their roles in lipid metabolism. J Lipid Res, 43:2-12.
Ettinger MP., (2003) Aging bone and osteoporosis: strategies for preventing fractures in the elderly. Arch Intern Med. 163(18):2237-46. Review.
Fajas et al., (1999) Regulation of peroxisome proliferator-activated receptor gamma expression by adipocyte differentiation and determination factor 1/sterol regulatory element binding protein 1: implications for adipocyte differentiation and metabolism. Mol Cell Biol., (8):5495-503.
Franceschi et al., (2000) Gene therapy for bone formation: in vitro and in vivo osteogenic activity of an adenovirus expressing BMP7. J Cell Biochem, 78(3):476-86.
Franceschi et al., (2003) Regulation of the osteoblast-specific transcription factor, Runx2: responsiveness to multiple signal transduction pathways. J Cell Biochem., 88(3):446-54. Review.
Fujita et al., (2004) Runx2 induces osteoblast and chondrocyte differentiation and enhances their migration by coupling with PI3K-Akt signaling. J Cell Biol., 166(1):85-95. Epub Jun. 28, 2004.
Fukuchi et al., (2004) Antiproliferative effect of liver X receptor agonists on LNCaP human prostate cancer cells. Cancer Res., 64(21):7686-9.
Galus et al., (2006) Fluvastatin does not elevate periosteal osteogenesis induced by Moloney sarcoma virus (MSV) in mice. Pharmacol. Rep., 58(1): 60-66.
Garrett et al., (2002) The role of statins as potential targets for bone formation. Arthritis Res., 4(4): 237-240.
Garrett et al., (2003) Selective inhibitors of the osteoblast proteasome stimulate bone formation in vivo and in vitro. J Clin Invest., 111(11):1771-82.
Gaur et al., (2005) Canonical WNT signaling promotes osteogenesis by directly stimulating Runx2 gene expression. J Biol Chem., 280(39):33132-40.
Gen et al., (1973) J Am Chem Soc., 95: 2656-2663.
Ghosh-Choudhury et al., (2002) Requirement of BMP-2-induced phosphatidylinositol 3-kinase and Akt serine/threonine kinase in osteoblast differentiation and Smad-dependent BMP-2 gene transcription. J Biol Chem., 277(36):33361-8. Epub Jun. 25, 2002. Erratum in: J Biol Chem. May 2, 2003;278(18):16452.
Ghosh-Choudhury et al., (2007) Statin-induced Ras activation integrates the phosphatidylinositol 3-kinase signal to Akt and MAPK for bone morphogenetic protein-2 expression in osteoblast differentiation. J Biol Chem., 282(7):4983-93.
Gimble et al., (1996) Peroxisome proliferator-activated receptor-γ activation by thiazolidinediones induces adipogenesis in bone marrow stromal cells. Mol Pharmacol 50:1087-1094.
Goltzman et al., (2002) Discoveries, drugs and skeletal disorders. Nat Rev Drug Discov., (10):784-96.
Gordon et al., (2006) Wnt signaling: multiple pathways, multiple receptors, and multiple transcription factors. J Biol Chem., 281(32):22429-33. Epub Jun. 22, 2006. Review.
Gori et al., (1999) Differentiation of human marrow stromal precursor cells: bone morphogenetic protein-2 increases OSF2/CBFA1, enhances osteoblast commitment, and inhibits late adipocyte maturation. J Bone Miner Res., 14(9):1522-35.
Hanada et al., (1997) Stimulatory effects of basic fibroblast growth factor and bone morphogenetic protein-2 osteogenic differentiation of rat bone marrow-derived mesenchymal stem cells. J. Bone and Mineral Research 12(10): 1606-1614.
Hanley et al., (2000) Oxysterols induce differentiation in human keratinocytes and increase AP-1-dependent involucrin transcription. J Invest Dermatol 114:545-553.
Hayden et al., (2002) Induction of moncyte differentiation and foam cell formation in vitro by 7-ketocholesterol. J Lipid Res., 43:26-35.
Hicok et al., (1998) Development and characterization of conditionally immortalized osteoblast precursor cell lines from human bone marrow stroma. J Bone Miner Res, 13(2):205-2217.

(56) References Cited

OTHER PUBLICATIONS

Hill et al., (2005) Canonical Wnt/beta-catenin signaling prevents osteoblasts from differentiating into chondrocytes. Dev Cell. 8(5):727-38.
Honda et al., (1986) Biologically active glycosides from Asteroidia. XI. Structures of thornasterols A and B. Tetrahedron Lett, 27:3369-3372.
Honda et al., (1996) J Chem Soc., Perkin Trans., 1: 2291-2296 (no detailed info found in PubMed).
Hosack et al., (2003) Identifying biological themes within lists of genes with EASE. Genome Biol. 4(10):R70. Epub Sep. 11, 2003.
Hu et al., (2004) Sequential roles of hedgehog and Wnt signaling in osteoblast development. Development 132:49-60.
Ichioka et al., (2002) Prevention of senile osteoporosis in SAMP6 mice by intrabone marrow injection of allogeneic bone marrow cells. Stem Cells. 20(6):542-51.
ISR for PCT/US03/027105 mailed May 5, 2004.
ISR for PCT/US04/028162 mailed Feb. 22, 2005.
ISR for PCT/US06/012902 mailed Jul. 7, 2008.
ISR for PCT/US06/34374 mailed Jun. 16, 2008.
ISR for PCT/US07/016309 mailed Sep. 16, 2008.
ISR for PCT/US07/05073 mailed Oct. 29, 2007.
ISR for PCT/US07/25833 mailed Sep. 11, 2008.
ISR for PCT/US08/013319 mailed Apr. 8, 2009.
Iwata et al., (2002) Demineralized bone matrix and native bone morphogenetic protein in orthopaedic surgery. Clin Orthop Relat Res., (395):99-109. Review.
Izumo et al., (2001) Lipophilic statins can be osteogenic by promoting osteoblastic calcification in a Cbfa1- and BMP-2-independent manner. Methods and Findings in Experimental and Clinical Pharmacology, 23(7): 389-394.
Johnson et al., (2004) LRP5 and Wnt signaling: a union made for bone. J Bone Miner Res., 19(11):1749-57.
Jung et al., (1999) First total synthesis of Zestobergesterol A and active structural analogues of the Zestobergesterol. Organic Lett 1:1671-1674.
Juvet et al., (2003) On the role of liver X receptors in lipid accumulation in adipocytes. Mol Endocrinol., 17(2):172-82.
Kadiyala et al., (1997) Culture expanded canine mesenchymal stem cells possess osteochondrogenic potential in vivo and in vitro. Cell Transplantation, 6;(2):125-134.
Kametani et al., (1986) J Org Chem., 51: 2932-2939.
Kennell et al., (2005) Wnt signaling inhibits adipogenesis through beta-catenin-dependent and -independent mechanisms. J Biol Chem., 280(25):24004-10.
Kha et al., (2004) Oxysterols regulate differentiation of mesenchymal stem cells: pro-bone and anti-fat. J Bone Miner Res 19:830-840.
Kim et al., (1998) ADD1/SREBP1 activates PPARgamma through the production of endogenous ligand. Proc Natl Acad Sci U S A. 95(8):4333-7.
Kim et al., (2006) Osteogenic oxysterol, 20(S)-Hydroxycholesterol, inhibits PPAR gamma expression and adipogenic differentioation of bone marrow stromal cells through s hedgehog-, wnt-, and MAPK-Dependent Mechanism. J Bone Miner Res. 21(1): S394.
Komori et al., (2005) Regulation of skeletal development by the Runx family of transcription factors. J Cell Biochem., 95(3):445-53.
Kurland et al., (2000) Parathyroid hormone as a therapy for idiopathic osteoporosis in men: effects on bone mineral density and bone markers. J Clin Endocrinol Metab 85:3069-3076.
Lefevre et al., (1978) Adrenal cholesterol-binding protein: properties and partial purification. FEBS Letters 89(2): 287-292.
Lehmann et al., (1997) Activation of the nuclear receptor LXR by oxysterols defines a new hormone response pathway. J Biol Chem 272:3137-3140.
Li et al., (2001) Delivering on the promise of bone morphogenetic proteins. Trends Biotechnol. 19(7):255-65. Review.
Libby et al., (2002) Inflammation in atherosclerosis. Nature 420:868-874.
Lieberman et al., (2002) The role of growth factors in the repair of bone. J Bone & Joint Surg, 84A:1032-1044.
Long et al., (2001) Genetic manipulation of hedgehog signaling in the endochondral skeleton reveals a direct role in the regulation of chondrocyte proliferation. Development 128:5099-5108.
Lum et al., (2004) The hedgehog response network: sensors, switches, and routers. Science 304:1755-1759.
Maeda et al., (2001) Simvastatin promotes osteoblast differentiation and mineralization in MC3T3-E1 cells. Biochem Biophys Res Commun. 280(3):874-7.
Maggio et al., (2003) Marked decrease in plasma antioxidants in aged osteoporotic women: results of a cross-sectional study. J Clin Endocrinol Metab. 88(4):1523-7.
Majors et al., (1997) Characterization of human bone marrow stromal cells with respect to osteoblastic differentiation. J Bone & Joint Surgery 15:546-557.
Makino et al., (1978) Steroid conformations in solid and solution: stereoselectivity of Grignard addition to 20-keto steroids. J. Org. Chem. 43(2): 276-280.
Manolagas et al., (2000) Birth and death of bone cells: basic regulatory mechanisms and implications for the pathogenesis and treatment of osteoporosis. Endocr Rev. 21(2):115-37.
Manolagas SC, (1998) Cellular and molecular mechanisms of osteoporosis. Aging 10(3):182-190.
Mazzocchi et al., (1983) J Org Chem 48: 2981-2989 (no detailed info found in PubMed).
Mbalaviele et al., (2005) Beta-catenin and BMP-2 synergize to promote osteoblast differentiation and new bone formation. J Cell Biochem. 94(2):403-18.
Meaney et al., (2001) Evidence that the major oxysterols in human circulation originate from distinct pools of cholesterol: a stable isotope study. J Lipid Res 42:70-78.
Melton LI. et al., (1995) How many women have osteoporosis now? J Bone Miner Res 10:175-177.
Meunier et al., (1971) Osteoporosis and the replacement of cell populations of the marrow by adipose tissue: A quantitative study of 84 iliac bone biopsies. Clinical Orthopedics and Related Res 80:147-154.
Mezey et al., (2009) Oral Diseases, Abstract.
Mitsunobu O., (1981) The use of diethyl azodicarboxylate and triphenylphosphine in syntheses and transformation of natural products. Synthesis 1-28.
Miyamoto et al., (2003) Prostaglandin E2-mediated anabolic effect of a novel inhibitor of phosphodiesterase 4, XT-611, in the in vitro bone marrow culture.J Bone Miner Res. (8):1471-7.
Mody et al., (2001) Oxidative stress modulates osteoblastic differentiation of vascular and bone cells. Free Radic Biol Med., 31(4):509-19.
Moerman et al., (2004) Aging activates adipogenic and suppresses osteogenic programs in mesenchymal marrow stroma/stem cells: the role of PPAR-gamma2 transcription factor and TGF-beta/BMP signaling pathways. Aging Cell. 3(6):379-89.
Morisaki et al., (1977) Studies on steroids. XLV. Synthesis of the four stereoisomers of 20,22-dihydroxycholesterol. Chem Pharm Bull 25:2576-2583.
Mullor et al., (2001) Wnt signals are targets and mediators of Gli function. Curr Biol. 11(10):769-73.
Mullor et al., (2002) Pathways and consequences: hedgehog signaling in human disease. Trends Cell Bio 12:562-569.
Mundy et al., (1999) Science 286: 1946-1949.
Mundy et al., (2002) Directions of drug discovery in osteoporosis. Annu Rev Med 53;337-354.
Nagano et al., (1977) Chemistry and biochemistry of Chinese drugs, Part II—Hydroxylated sterols, cytotoxic towards cancerous cells: synthesis and testing. J. Chem. Res. (M) V. 9, pp. 2522-2571.
Nakamura et al., (1997) Stimulation of bone formation by intraosseous application of recombinant basic fibroblast growth factor in normal and ovariectomized rabbits. J. Orthopaedic Research, 15:(2):307-313.
Office Action for U.S. Appl. No. 10/524,945 dated Mar. 23, 2009.
Office Action for U.S. Appl. No. 10/524,945 dated Jun. 11, 2008.
Office Action for U.S. Appl. No. 10/569,994 dated Jan. 2, 2009.
Office Action for U.S. Appl. No. 10/569,994 dated May 30, 2008.

(56) References Cited

OTHER PUBLICATIONS

Office Action mailed Aug. 31, 2009 in related U.S. Appl. No. 10/569,994.
Olkkonen et al., (2004) Oxysterols and oxysterol binding proteins: role in lipid metabolism and atherosclerosis. Ann Med 36:562-572.
Otto et al., (1997) Cbfa1, a candidate gene for cleidocranial dysplasia syndrome, is essential for osteoblast differentiation and bone development. Cell 89:765-771.
Panakova et al., (2005) Lipoprotein particles are required for hedgehog and wingless signaling. Nature 435:58-65.
Parhami et al., (2002) Role of the cholesterol biosynthetic pathway in osteoblastic differentiation of marrow stromal cells. J Bone Miner Res. 17(11):1997-2003.
Parish et al., (1995) Side-chain oxysterol regulation of 3-hydroxy-3-methylglutaryl coenzyme A reductase activity. Lipids 247-251.
Peet et al., (1998) The LXRs: a new class of oxysterol receptors. Curr Opin Genetics & Develop 8:571-575.
Pikuleva et al., (2001) Putative Helix F Contributes to Regioselectivity of Hydroxylation in Mitochondrial Cytochrome P450 27A1. Biochemistry, v. 40 pp. 7621-7629.
Pittenger et al., (1999) Multilineage potential of adult human mesenchymal stem cells. Science 284:143-147.
Poza et al., (2007) Synthesis and evaluation of new 6-hydroximinosteroid analogs as cytotoxic agents. Bioorg Med Chem. 15(14):4722-40.
Prockop DJ., (1997) Marrow stromal cells as stem cells for nonhematopoietic tissues. Science, 276:71-74.
Quarto et al., (1995) Bone progenitor cell deficits and the age-associated decline in bone repair capacity. Calcif Tissue Int., 56(2):123-9.
Raisz LG., (1997) The osteoporosis revolution. Ann Int Med 126:458-462.
Rao AS., (1991) Addition reactions with formation of carbon-oxygen bonds: (1) General methods of epoxidation. Comprehensive Organic Synthesis, Pergamon Press, Eds. Trost BM, Fleming I. 7 (chapter 3.1); 376-380.
Rao et al., (1999) Lovastatin-mediated G1 arrest is through inhibition of the proteosome, independent of hydroxymethyl glutarl-CoA reductase. Proc. Natl. Acad. Sci. 96: 7797-7802.
Rawadi et al., (2003) BMP-2 controls alkaline phosphatase expression and osteoblast mineralization by a Wnt autocrine loop. J Bone Miner Res., 18(10):1842-53.
Reeve et al., (2001) Treatment with parathyroid peptides and estrogen replacement for severe postmenopausal vertebral osteoporosis: prediction of long-term responses in spine and femur. J Bone Miner Res 19:102-114.
Reinholz et al., (2000) Bisphosphonates directly regulate cell proliferation, differentiation, and gene expression in human osteoblasts. Cancer Res., 60(21):6001-7.
Richardson JA et al. (2005) Characterization of osteogenic oxysterols and their molecular mechanism(s) of action. J Bone Miner Res 20:S1;S414.
Rickard et al., (1994) Induction of rapid osteoblast differentiation in rat bone marrow stromal cell cultures by dexamethasone and BMP-2. Dev Biol., 161(1):218-28.
Riggs et al., (1992) The prevention and treatment of osteoporosis. N Engl J Med., 327(9):620-7. Review.
Riobó et al., (2006) Phosphoinositide 3-kinase and Akt are essential for Sonic Hedgehog signaling. Proc Natl Acad Sci U S A. 103(12):4505-10.
Rodan et al., (2000) Therapeutic approaches to bone diseases. Science 289:1508-1514.
Rodda et al., (2006) Distinct roles for Hedgehog and canonical Wnt signaling in specification, differentiation and maintenance of osteoblast progenitors. Development. 133(16):3231-44.
Ruan et al., (1999) An improved synthesis of (20R,22R)-cholest-5-ene-3β,20,22-triol, and intermediate in steroid hormone formation and an activator of nuclear orphan receptor LXRα. Steroids 64:385-395.
Rubin CD., (1999) Treatment considerations in the management of age-related osteoporosis. The American J Medical Sciences, 318 (3):158-170.
Russell DW., (2000) Oxysterol biosynthetic enzymes. Biochimica et Biophysica Acta, 1529:126-135.
Sammons et al., (2004) The role of BMP-6, IL-6, and BMP-4 in mesenchymal stem cell-dependent bone development: effects on osteoblastic differentiation induced by parathyroid hormone and vitamin D3. Stem Cells and Development, 13: 273-280.
Sanchez et al., (2004) Inhibition of prostate cancer proliferation by interference with SONIC Hedgehog-GLI1 signaling. Proc Natl Acad Sci U S A. 101(34):12561-6.
Sang et al., (2005) Ectopic overexpression of adipogenic transcription factors induces transdifferentiation of MC3T3-E1 osteoblasts. Biochemical and Biophysical Research Communications 327(3): 811-819.
Schaafsma et al. (2001) Delay of natural bone loss by higher intake of specific minerals and vitamins. Crit Rev Food Sci Nutr 41:225-249.
Schroepfer GJ Jr., (2000) Oxysterols: modulators of cholesterol metabolism and other processes. Physiol Rev. 80(1):361-554. Review.
Seo et al., (2004) Activated liver X receptors stimulate adipocyte differentiation through induction of peroxisome proliferator-activated receptor gamma expression. Mol Cell Biol. 24(8):3430-44.
Shan et al., (2003) Chromatographic behavior of oxygenated derivatives of cholesterol. Steroids 68 pp. 221-233.
Shea et al., (2003) BMP treatment of C3H10T1/2 mesenchymal stem cells induces both chondrogenesis and osteogenesis. J Cell Biochem. 90(6):1112-27.
Shimaoka et al., (2004) Recombinant growth/differentiation factor-5 (GDF-5) stimulates osteogenic differentiation of marrow mesenchymal stem cells in porous hydroxyapatite ceramic. J Biomed Mater Res A. 68(1):168-76.
Shimizu et al., (1962) 20α, 22-Dihydroxycholesterol, an Intermediate in the Biosynthesis of Pregnenolone (3β-Hydroxypregn-5-en-20-one) from Cholesterol. J. Biol. Chem., 237;(3): 699-702.
Shouhed et al., (2005) Osteogenic oxysterols inhibit the adverse effects of oxidative stress on osteogenic differentiation of marrow stromal cells. J Cell Biochem 95:1276-1283.
Silva-Vargas et al., (2005) Beta-catenin and Hedgehog signal strength can specify number and location of hair follicles in adult epidermis without recruitment of bulge stem cells. Dev Cell. ;9(1):121-31.
Sohal et al., (2002) Mechanisms of aging: an appraisal of the oxidative stress hypothesis. Free Radic Biol Med. 33(5):575-86. Review.
Song et al., (2002) Chinese Journal of Reparative and Reconstructive Surgery, 16: 384-387.
Spinella-Jaegle et al., (2001) Sonic hedgehog increases the commitment of pluripotent mesenchymal cells into the osteoblastic lineage and abolishes adipocytic differentiation. J Cell Sci 114:2085-2094.
Spiro et al., (2001) Spinal fusion with recombinant human growth and differentiation factor-5 combined with a mineralized collagen matrix. Anat Rec. 263(4):388-95.
St-Jacques et al., (1999) Indian hedgehog signaling regulates proliferation and differentiation of chondrocytes and is essential for bone formation. Genes Dev., 13:2072-2086.
Stein et al., (1993) Molecular mechanisms mediating proliferation/differentiation interrelationships during progressive development of the osteoblast phenotype. Endocrine Rev 14:424-442.
Steitz et al., (2001) Smooth Muscle Cell Phenotypic Transition Associated With Calcification: Upregulation of Cbfa1 and Downregulation of Smooth Muscle Lineage Markers. Circ. Res. 89:1147-1154.
Stewart et al., (2003) Expression of the developmental Sonic hedgehog (Shh) signalling pathway is up-regulated in chronic lung fibrosis and the Shh receptor patched1 is present in circulating T lymphocytes. J Pathol 199:488-495.
Suh et al., (2006) Hedgehog signaling plays a conserved role in inhibiting fat formation. Cell Metab. 3(1):25-34.

(56) References Cited

OTHER PUBLICATIONS

Supplemental European Search Report (EP 06824888.9) Jul. 1, 2009.
Swarthout et al., (2002) Parathyroid hormone-dependent signaling pathways regulating genes in bone cells. Gene. 282(1-2):1-17. Review.
Szendi et al., (2002) 1,5-Hydride shift in Wolff-Kishner reduction of (20R)-3β,20, 26-trihydroxy-27-norcholest-5-en-22-one; synthetic, quantum chemical, and NMR studies, Steroids 67;31-38.
Taipale et al., (2001) The Hedgehog and Wnt signalling pathways in cancer. Nature. 411(6835):349-54. Review.
Taylor et al., (1986) 24,25-Epoxysterol metabolism in cultured mammalian cells and repression of 3-hydroxy-3-methylglutaryl-CoA reductase. J Biol Chem. 261(32):15039-44.
Thies et al., (1992) Recombinant human bone morphogenetic protein-2 induces osteoblastic differentiation in W-20-17 stromal cells. Endocrinology 130(3): 1318-1324.
Tintut et al., (2003) Multilineage Potential of Cells From the Artery Wall. Circulation.108: 2505-2510.
Valentin-Opran et al., (2002) Clinical evaluation of recombinant human bone morphogenetic protein-2. Clin Orthop & Related Res; v. 395:110-120.
Velgova et al., (1969) Collect. Czech. Chem. Commun. 34: 3354-3375.
Viccica et al., (2007) Role of the cholesterol biosynthetic pathway in osteoblastic differentiation. J. Endocrinol. Invest. 30(6S): 8-12.
Vine et al., (1998) Dietary oxysterols are incorporated in plasma triglyceride-rich lipoproteins, incrase their susceptibility to oxidation and increase aortic cholesterol concentrations in rabbits. J Lipid Res 1995-2004.
Väänänen HK., (2005) Mesenchymal stem cells. Ann Med. 37(7):469-79. Review.
Wada et al., (1999) Calcification of Vascular Smooth Muscle Cell Cultures : Inhibition by Osteopontin. Circ. Res. 84:166-178.
Wada et al., (2000) Lack of Positive Correlation Between Statin Lie and Bone Mineral Density in Japanese Subjects With Type 2 Diabetes. Arch Intern Med. 160:2865.
Wang et al., (1995) Lipid Clearing Agents in Steroid-Induces Osteoporosis. J Formos Med Assoc. 94(10): 589-592.
Wang et al., (2000) The Nicolas Andry award. The pathogenesis and prevention of steroid-induced osteonecrosis. Clin Orthop Relat Res. (370):295-310.
Watanabe et al.,(2004) Stereoselective synthesis of (22R)- and (22S)-castasterone/ponasterone A hybrid compounds and evaluation of their molting hormone activity. Steroids 69: 483-493.
Watson et al., (1994) TGF-beta and 25-hydroxycholesterol stimulate osteoblast-like vascular cells to calcify. J Clin Invest 93:2106-2113.
Westendorf et al., (2004) Wnt signaling in osteoblasts and bone diseases. ene. 341:19-39. Review.
Wiersig et al., (1979) Stereospecific synthesis of the side chain of the steroidal plant sex hormone oogoniol. J. Org. Chem. 44(19): 3374-3382.
Woo et al., (2001) Enhancement of bone growth by sustained delivery of recombinant human bone morphogenetic protein-2 in a polymeric matrix. Pharm Res 18:1747-1753.
Written Opinion for PCT/US04/028162 mailed Feb. 22, 2005.
Written Opinion for PCT/US06/012902 mailed Jul. 7, 2008.
Written Opinion for PCT/US06/34374 mailed Jun. 16, 2008.
Written Opinion for PCT/US07/016309 mailed Sep. 16, 2008.
Written Opinion for PCT/US07/05073 mailed Oct. 29, 2007.
Written Opinion for PCT/US08/013319 mailed Apr. 8, 2009.
Yamaguchi et al., (2000) Regulation of osteoblast differentiation mediated by bone morphogenetic proteins, hedgehogs, and Cbfa1. Endocrine Rev 21:393-411.
Yang et al., (2002) Transcription factors in bone: developmental and pathological aspects. Trends Mol Med. 8(7):340-5. Review.
Yang et al., (2006) Parathyroid hormone activates PKC-delta and regulates osteoblastic differentiation via a PLC-independent pathway. Bone. 38(4):485-96. Epub Dec. 1, 2005.
Yeh et al., (2002) Journal of Cell Biochemistry, 87: 292-304.
Yoon et al., (2002) Osteoinductive molecules in orthopaedics: basic science and preclinical studies. Clin Orthop & Related Res, v. 395:33-43.
Yoshida et al., (2002) Core-binding factor beta interacts with Runx2 and is required for skeletal development. Nat Genet. 32(4):633-8.
Yoshida et al., (2002) Stimulation of bone formation and prevention of bone loss by prostaglandin E EP4 receptor activation. Proc Natl Acad Sci U S A. 99(7):4580-5. Epub Mar. 26, 2002 (author typo: Yoshia).
Zanchetta et al., (2003) Systematic effects on bone healing of a new hyaluronic acid-like bacterial exopolysaccharide. Calcif Tissue Int., 73:232-236.
Zander et al., (1977) Chemistry and Biochemistry of Chinese Drugs. Part III. Mechanism of Action of Hydroxylated Sterols on Cultured Hepatoma Cells, J. Chem. Res. (S) v. 9, p. 219.
Zelcer et al., (2006) Liver X receptors as integrators of metabolic and inflammatory signaling. J Clin Invest 116:607-614.
Zhang et al., (2002) Cyclooxygenase-2 regulates mesenchymal cell differentiation into the osteoblast lineage and is critically involved in bone repair, J. Clinical Investigation, 109;(11);1405-1415.
Zhao et al., (2003) E3 ubiquitin ligase Smurf1 mediates core-binding factor alpha1/Runx2 degradation and plays a specific role in osteoblast differentiation. J Biol Chem. 278(30):27939-44.
Zhao et al., (2006) The zinc finger transcription factor Gli2 mediates bone morphogenetic protein 2 expression in osteoblasts in response to hedgehog signaling. Mol Cell Biol 26:6197-6208.
Ziros et al., (2002) The bone-specific transcriptional regulator Cbfa1 is a target of mechanical signals in osteoblastic cells. J Biol Chem. 277(26):23934-41.
Kim, S. et al., "Identification of Two Brassinosteroids from the Cambial Region of Scots Pine (*Pinus silverstris*) by Gas Chromatography-Mass Spectometry, after Detection Using a Dwarf Rice Lamina Incilnation Bioassay," vol. 94, pp. 1709-1713 (1990).
ISR for PCT/US05/19870 mailed Oct. 14, 2005.
Antonio, V. et al. "Oxysterol and 9-*cis*-retinoic acid stimulate the group IIA secretory phospholipase A2 gene in rat smooth-muscle cells," Biochem J., vol. 376, pp. 351-360 (2003).
Yao, Z. et al., "22*R*-Hydroxycholesterol protects neuronal cells from β-amyloid-induced cytotoxicity by binding β-amyloid peptide," Journal of Neurochemistry vol. 83, pp. 1110-1119 (2002).
Cheng et al., (1977) Chemistry and Biochemistry of Chinese Drugs. Part 1. Sterol Derivatives Cytotoxic to Hepatoma Cells, Isolated from the Drug Bombyx cum Botryte. J. Chem. Res. (M) v. 9 pp. 2519-2521.
Nagano et al., (1977) Chemistry and biochemistry of Chinese drugs, Part II—Hydroxylated sterols, cytotoxic towards cancerous cells: synthesis and testing. J. Chem. Res. (S) v. 9, p. 218.
Zander et al., (1977) Chemistry and Biochemistry of Chinese Drugs. Part III. Mechanism of Action of Hydroxylated Sterols on Cultured Hepatoma Cells, J. Chem. Res. (M) v. 9, p. 2572.
Hummasti, S. et al., "Liver X receptors are regulators of adipocyte gene expression but not differentiation: identification of apoD as a direct target," Journal of Lipid Research, vol. 45, pp. 616-625 (2004).
Supplementary European Search Report issued in EP 03749213.9, mailed Jun. 15, 2009.
ISR from PCT/US2011/025064 mailed Nov. 9, 2011.
Office Action dated May 22, 2012, issued in U.S. Appl. No. 12/224,430.
Ciobanu, L. et al., "Synthesis and steroid sulphatase inhibitory activity of C19- and C21-steroidal derivatives bearing a benzyl-inhibiting group," European Journal of Medicinal Chemistry, vol. 36(7-8), pp. 659-671 (2001).
Abe et al., "Effects of bisphosphonates on osteoclastogenesis in RAW264.7 cells," 2012, *International Journal of Molecular Medicine* 29.6: 1007-1015.
Acsadi et al., "Human dystrophin expression in mdx mice after intramuscular injection of DNA constructs," 1991, *Nature* 352: 815-818.
Albers M. et al., "A novel principle for partial agonism of liver X receptor ligands," 2006, *Journal of Biological Chemistry* 281(8):4920-4930.

(56) References Cited

OTHER PUBLICATIONS

Amantea et al., "Oxysterol-induced osteogenic differentiation of marrow stromal cells is regulated by Dkk-1 inhibitable and P13-Kinase mediated signaling," 2008, *Journal of Cellular Biochemistry* 105(2): 424-436.
Arns et al., "Design and synthesis of novel bone-targeting dual-action pro-drugs for the teament and reversal of osteoporosis," 2012, *Bioorganic and Medicinal Chemistry*. 20(6):2131-2140.
Aspray et al., "Treatment of osteoporosis in women intolerant of oral bisphosphonates," 2012, *Maturitas*, 71:76-78.
Bailey et al., "Sonic Hedgehog paracrine signaling regulates metastasis and lymphangiogenesis in pancreatic cancer," 2009, *Oncogene* 28(40): 3513-3525.
Barginear et al., "The hedgehog pathway as a therapeutic target for treatment of breast cancer," 2009, *Breast cancer research and treatment* 116(2):239-246.
Bauss et al., "Effect of 17B-estradiol-biphosphonate conjugates, potentiial bone-seeking estrogen pro-drugs, on 17B-estradiol serum kinetics and bone mass in rats," 1996, *Calcified Tissue International* 59: 168-173.
Black et al., "Continuing bisphosphonate treatment for osteoporosis - for whom and for how long?" 2012, *New England Journal of Medicine* 366(22), 2051-2053.
Brewer et al., "Current and future treatment options in osteoporosis," 2011, *European Journal of Clinical Pharmacology* 67(4): 321-331.
Bruice, T. C. et al. *Bioorganic Mechanisms*, vol. 1, W. A. Benjamin, New York, 1966, 1-258.
Canalis, "Update in new anabolic therapies for osteoporosis," 2010, *The Journal of Clinical Endocrinology and Metabolism* 95(4), 1496-1504.
Chen et al., "Small molecule modulation of Smoothened activity," 2002, *Proceedings of the National Academy of Sciences*, 99(22), 14071-14076.
Chisholm et al., "The LXR ligand T0901317 induces severe lipogenesis in the db/db diabetic mouse," 2003, *Journal of Lipid Research* 44(11):2039-2048; 2003.
Cline et al., "Perspectives for gene therapy: inserting new genetic information into mammalian cells by physical techniques and viral vectors," 1985, *Pharmacology and therapeutics* 29(1):69-92.
Cosman. "Anabolic and Atiresorptive Therapy for Osteoporosis: Combination and Sequential Approaches," 2014, *Current osteoporosis reports* 12(4):385-395.
Dimitriou et al., "Bone regeneration: current concepts and future directions," 2011, *BMC Medicine* 9(1):1-10.
Dlugosz et al., "Following the Hedgehog to new cancer therapies," 2009, *New England Journal of Medicine* 361(12):1202-1205.
Ebetino et al., "The relationship between the chemistry and biological activity of the bisphosphonates," 2011, *Bone* 49(1):20-33.
Feldmann et al., "Blockade of Hedgehog signaling inhibits pancreatic cancer invasion and metastasis: A new paradigm for combination therapy in solid tumors," 2007, *Cancer Research* 67(5):2187-2196.
Fievet et al., "Liver X receptor modulators: Effects on lipid metabolism and potential use in the treatment of atherosclerosis," 2009, *Biochemical Pharmacology* 77(8):1316-1327.
Forman et al., "The orphan nuclear receptor LXRa is positively and negatively regulated by distinct products of mevalonate metabolism," 1997, *Proceedings of the National Academy of Sciences of the United States of America* 94(20), pp. 10588-10593.
Friedmann et al., "Progress toward human gene therapy," 1989, *Science* 244(4910):1275-1281.
Geyeregger et al., "Liver x receptors interfere with cytokine-induced proliferation and cell survival in normal and leukemic lymphocytes," 2009, *Journal of Leukocyte Biology* 86:1039-1048.
Gill et al., "Sterol regulators of cholesterol homeostasis and beyond: The oxysterol hypothesis revisited and revised," 2008, *Progress in Lipid Research* 47(6):391-404.
Gregorio-King et al., "Effect of oxysterols on hematopoietic progentior cells," 2002, *Experimental Hematology* 30(7): 670-678.
Hilton M. et al., "Ihh controls cartilage development by antagonizing Gli3, but requires additional effectors to regulate osteoblast and vascular development," 2005, *Development* 132(19):4339-4351.
Hirotsu et al., "Smoothened as a new therapeutic target for human osteosarcoma," 2010, *Molecular Cancer* 9(1):1-14.
Hochman E. et al., "Molecular pathways regulating pro-migratory effects of hedgehog signaling," 2006, *Journal of Biological Chemistry* 281(45):33860-33870.
Hokugo et al., "A novel oxysterol promotes bone regenration in rabbit cranial bone defects," 2013, *Journal of Tissue Engingeering and Regenerative Medicine*.
International Search Report and Written Opinion issued in PCT/US2015/028917 dated Jul. 27, 2015.
International Search Report and Written Opinion issued in PCT/US2013/032693 dated Jul. 18, 2013.
International Search Report and Written Opinion issued in PCT/US2014/036680 dated Sep. 10, 2014.
International Search Report and Written Opinion issued in PCT/US2008/003493 dated Oct. 12, 2009.
International Search Report and Written Opinion issued in PCT/US2010/041560 dated Aug. 31, 2010.
International Search Report and Written Opinion issued in PCT/US2013/032650 dated Jul. 18, 2013.
International Search Report and Written Opinion issued in PCT/US2013/039748 dated Sep. 25, 2013.
Jahnke et al., "An in vitro Assay to Measure Targeted Drug Delivery to Bone Mineral," 2010, *ChemMedChem* 5(5):770-776.
Jiang et al., "Hedgehog signaling in development and cancer". 2008, *Developmental Cell* 15(6):801-812.
Johnson et al., "Novel oxysteols have pro-osteogenic and anti-adipogenic effects in vitro and induce spinal fusion in vivo," 2011, *Journal of Cellular Biochemistry* 112(6): 1673-1684.
Johnson et al., "Human bone morphogenetic protein allografting for reconstruction of femoral nonunion," 2000, *Clinical Orthopaedics and Related Research* 371:61-74.
Joseph S., et al., "Synthetic LXR ligand inhibits the development of atherosclerosis in mice," 2002, *Proceedings of the National Academy of Sciences* 99(11):7604-7609.
Kaneko et al., "Induction of Intestinal ATP-binding cassette transporters by a phytosterol-derived liver x receptor agonist," 2003, *The Journal of Biological Chemistry* 278(38)36091-36098.
Kim et al., "Hedgehog signaing and osteogenic differentiation in multioptent bone marrow stromal cells are inhibited by oxidative stress," 2010, *Journal of Biological Chemistry* 111(5):1199-1209.
Kim et al., "Osteogenic oxysterol, 20(S)-hydroxycholesterol, induces Notch target gene expression in bone marrow stromal cells," 2010, *Journal of Bone and Mineral Research* 25(4):782-795.
Koreeda et al., "Chirality transfer in stereoselective synthesis. A highly stereocontrolled synthesis of 22-hydroxylated steroid side chains via the [2,3]-Wittig rearrangmeent," 1986, *Journal of Organic Chemistry* 51(21):4090-4092.
Larsson et al. "Kinetics of GI progression in 3T6 and SV-3T3 cells following treatment by 25-hydroxycholesterol." 1986, *Cancer Research* 46(3):1233-1238.
Liao X. et al., "Aberrant activation of hedgehog signaling pathway in ovarian cancers: effect on prognosis, cell invasion and differentiation," 2009, *Carcinogenesis* 30(1):131-140.
Lin, "Bisphosphonates: A review of their pharmacokinetic properties," 1996, *Bone* 18(2):75-85.
Lin et al., "Pharmacokinetics of alendronate: an overview," 1999, *International journal of clinical practice. Supplement* 101:18-26.
Liu et al., "Interferon-inducible cholesterol-25-hydroxylase broadly inhibits viral entry by production of 25-hydroxycholesterol," 2013, *Immunity* vol. 38, pp. 92-105.
Luhmann et al., "Bone targeting for the treatment of osteoporosis," 2012, *Journal of Controlled Release* 161(2):198-213.
Lyritis et al., "Bone anabolic versus bone anticatabolic treatment of postmenopausl osteoporosis," 2010, *Annals of the New York Academy of Sciences* 1205:277-283.
Mimaki et al., "Lipid and steroidal constituents of *Lilium auratum* var. *platyphyllum* and *L. tenuifolium*," 1989, *Phytochemistry* 28(12), 3453-3458.

(56) References Cited

OTHER PUBLICATIONS

Montgomery et al., "A Novel Osteogenic Oxysterol Compound for Therapeutic Development to Promote Bone Growth: Activation of Hedgehog Signaling and Osteogenesis through Smoothened Binding," 2014, *Journal of Bone and Mineral Research* 29(8):1872-1885).

Morioka et al., "Design, synthesis and biological evaluation of novel estradio-biphosphonate conjugates as bone-specific estrogens," 2010, *Bioorganic and Medicinal Chemistry* 18(3):1143-1148.

Morisaki et al., "Stereochemical specificity at carbon-20 and -22 of hydroxylated cholsterals for side-chain cleavage by adrenocortical cytochrome P-450sec," 1976, *FEBS Letters* 72(2):337-40.

Muschitz et al., "Antiesorptives overlapping ongoing teriparatide treatment result in additional increases in bone mineral density," 2013, *Journal of Bone and Mineral Research* 28(1):196-205.

Myers et al., "Hedgehog pathway modulation by multiple lipid binding sites on the smoothened effector of signal response," 2013, *Developmental Cell* 26(4):346-357.

Nachtergaele et al., "Oxysterols are allosteric activators of the oncoprotein Smoothened," 2012, *Nature Chemical Biology* 8(2):211-220.

Nachtergaele et al., "Structure and function of the Smoothened extracellular domain in vertebrate Hedgehog signaling," 2013, *eLife* 2:e01340.

Nasim et al., "3-O-Phosphate ester conjugates of 17-beta-O-1,3,5(10)-estratriene as novel bone-targeting agents," 2010, *Bioorganic and Medicinal Chemistry Letters* 20:7450-7453.

Nedelcu et al., "Oxysterol binding to the extracellular domain of Smoothened in Hedgehod signaling," 2013, *Nature chemical biology* 9(9):557-564.

Nelson et al., "The oxysterol, 27-hydroxycholesterol, links cholesterol metabolism to bone homeostasis through its actions on the estrogen and liver x receptors," 2011, *Endocrinology* 152(12):4691-4705.

Nickolson et al., "Stereospecific synthesis of (20S,22R)-17α,20,22-trihydroxycholesterol and (20S,22S)-17a,20,22-trihydroxycholesterol," 1972, *Journal of Organic Chemistry* 37(13), 2119-2127.

Nishio et al., "3-hydroxy-3-methylglutaryl coenzyme A reductase inhibitor impairs cell differentiation in cultured adipogenic cells (3T3-L1)." 1996, *European Journal of Pharmacology* 301(1):203-206.

Parhami et al., "Lipid oxidation products have opposite effects on calcifying vascular cell and bone cell differentiation. A possible explanation for the paradox of arterial calcification in osteoporotic patients," 1997, *Arteriosclerosis, thrombosis, and vascular biology* 17(4):680-687.

Parish et al., "Regulation of 3-hydroxy-3-methylglutaryl coenzyme A reductase activity by side-chain oxysterols and their derivatives," 1999, *Critical Reviews in Biochemistry & Molecular Biology* 34(4):265-272.

Peacock C. et al., "Hedgehog signaling maintains a tumor stem cell compartment in multiple myeloma," 2007, *Proceedings of the National Academy of Sciences* 104(10):4048-4053.

Peng et al., "Antiatherosclerotic effects of a novel synthetic tissue-selective steroidal liver X receptor agonist in low-density lipoprotein receptor-deficient mice," 2008, *Journal of Pharmacology and Experimental Therapeutics* 327(2):332-342.

Pezacki et al., "Transcriptional profiling of the effects of 25-hydroxycholesterol on human hepatocyte metabolism and the antiviral state it conveys against the hepatitis C virus," 2009, *BMC Chemical Biology* 9(2):1-15.

Phelan C. et al., "Selective partial agonism of liver X receptor a is related to differential corepressor recruitement," 2008, *Molecular Endocrinology* 22(10): 2241-2249.

Porter J. et al., "Cholesterol modification of Hedgehog signaling proteins in animal development," 1996, *Science* 274:255-259.

Rachner et al., "New Horizons in Osteoporosis," 2011, *Lancet* 377(9773):1276-1287.

Raghow et al., "SREBPs: the crossroads of physiological and pathological lipid homeostasis," 2008, *Trends in Endocrinology and Metabolism* 19(2):65-73.

Raisz et al., "Pathgenesis of osteoporosis: concepts, conflicts, and prospects," 2005, *Journal of Clinical Investigation* 115(12):3318-3325.

Rehman et al., "Antiviral drugs against hepatitus C virus," 2011, *Genetic Vaccines and Therapy* 9(11): 1-10.

Reszka et al., "Mechanism of action of bisphosphonates," 2003, *Current Osteoporosis Reports* 1(2):45-52.

Richardson et al., "Oxysterol-induced osteoblastic differentiation of pluripotent mesenchymal cells is mediated through a PKC-and PKA-dependent pathway," 2007, *Journal of Cellular Biochemistry* 100(5):1131-45.

Roodman et al., "Bone Building with bortezomib," 2008, *Journal of Clinical Investigation* 118(2):462-464.

Rubin et al., "Targeting the Hedgehog pathway in cancer," 2006, *Nature reviews Drug discovery* 5(12):1026-1033.

Rudin et al., Treatment of medulloblatoma with Hedgehog pathway inhibitor GDC-0449, 2009, *New England Journal of Medicine* 361(12):1173-1178.

Sagan et al., "The influence of cholesterol and lipid metabolism on host cell structure and hepatitis C virus replication," 2006, *Biochemistry and Cell Biology* 84(1):67-79.

Schmidt et al., "A 15-ketosterol is a liver x receptor ligand that suppresses sterol-responsive element binding proteing-2 activity," 2006, *Journal of Lipid Research* 47:1037-1044.

Scott et al., "Comparison of a novel oxsterol molecule and rhBMP2 fusion rates in a rabbit posterolateral lumbar spine model," 2015, *The Spine Journal* 15:733-742.

Semb, "Isozymes of bone esterases," 1970, *Calcified Tissue Research* 6(1):77-80.

Shaw et al., "The Sonic Hedgehog pathway stimulates prostate tumor growth by paracrine signaling and recapitulates embryonic gene expression in tumor myofibroblasts". 2009, *Oncogene* 28(50):4480-4490.

Sheikh et al., "Mass spectometry in structural and stereochemical problems. CCXXX Preparation of 5a, 20a and 5a, 17a, 20a-cholestane-3b, 6a -diol. Electron impact induced framentation of steroidal D 17(20), D 20(21) and D 20(22) olefins," 1973, *Journal of Organic Chemistry* 38(20):3545-3553.

Shinoda et al., "HMG-CoA Reductase Inhibitor, Acceleration of Bone Formation with Satin," 2000, *Pharmacia* 649-650.

Silva et al., "New approaches to the treatment of osteoporosis," 2011, *Annual Review of Medicine* 62:307-322.

Sottero et al., "Cholesterol oxidation products and disease: an emerging topic of interest in medicinal chemistry," 2009, *Current Medicinal Chemistry* 16(6):685-705.

Stappenbeck et al., "Novel oxysterols activate the Hedgehod pathway and induce osteogenesis," 2012, *Bioorganic & Medicinal Chemistry Letters*, 22(18): 5893-5897.

Sugano et al., "Identification of intermediates in the conversion of cholesterol to pregnenolone with a reconstituted cytochrome P-450sec system: accumulation of the intermediate modulated by the adrenodoxin level," 1996, *Journal of Biochemistry* 120(4), pp. 780-787.

Sydykov et al., "Synthesis of (20S)-propargyl-5-pregnene-3β,20-diol and its use in the preparation of C27-steroids with an oxidized side chain," 1976, *Bioorganicheskaya Khimiya* 2(11):1531-1537. English Abstract Provided Only.

Sydykov et al, "Partial synthesis of 20(R),22(R)-D 5-cholestene-3b ,20,22-triol," 1977, *Izvestiya Akademiii Nauk SSSR, Seriya Khimicheskaya* 1:191-194.

Ta et al., "Osteosarcoma treatment: state of the art," 2009, *Cancer Metastasis Reviews* 28(1-2):247-263.

Teplyuk et al., "The osteogenic transcription factor runx2 controls genes involved in sterol/steroid metabolism, including CYP11A1 in osteoblasts," 2009, *Molecular Endocrinology* 23(6):849-861.

Thayer et al., "Hedgehog is an early and late mediator of pancreatic cancer tumorigenesis," 2003, *Nature* 425(6960):851-856.

Vedin et al., "The oxysterol receptor LXR inhibits proliferation of human breast cancer cells," 2009, *Carcinogenesis* 30(4):575-579.

(56) References Cited

OTHER PUBLICATIONS

Vescini et al., "PTH 1-84: bone rebuilding as a target for the therapy of severe osteoporosis." 2012, *Clinical Cases in Mineral and Bone Metabolism* 9(1):31-36.

Von Hoff et al., "Inhibition of the Hedgehog pathway in advanced basal-cell carcinoma," 2009, *New England Journal of Medicine* 361:1164-1172.

Wang et al., "Structure of the human smoothened receptor 7TM bound to an antitumour agent," 2013, *Nature* 497(7449):338-343.

Wolf et al., "A broad-spectrum antiviral targeting entry of enveloped viruses," 2010, *Proceedings of the National Academy of Sciences* 107(7):3157-3162.

Yamaguchi et al., "Osteoporosis and Vascular Calcfication," 2002, *Clinical Calcium* 39-43. English Abstract Provided Only.

Yao et al., "22R-hydroxycholesterol induces differentiation of human nt2 precursor (Ntera2/d1 teratocarcinoma) cells." 2007, *Neuroscience* 148(2):441-453.

Yauch et al., "A paracrine requirement for Hedgehog signaling in cancer," 2008, *Nature* 455(7211):406-410.

Yauch et al., "Hedgehog overexpression is associated with stromal interactions and predicts for poor outcome in breast cancer," 2011, *Cancer Research* 71(11): 4002-4015.

Zimmerman et al., "Stereochemical effects in cyclopropane ring openings: biomimetic ring openings of all isomers of 22,23-methylenecholesterol acetate," 1984, *Journal of the American Chemical Society* 106(19):5602-5612.

\* cited by examiner

[Oxy22]

[Oxy26]

[Oxy27]

[Oxy28]

[Oxy39]

[Oxy40]

[Oxy36]

[Oxy38]

[Oxy50]

[Oxy51]

[Oxy52]

[Oxy53]

SEQUENCE LISTING

```
<160> NUMBER OF SEQ ID NOS: 12

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tctctctgac ctcacagatg cc                                              22

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 2
taccttattg ccctcctgct tg                                              22

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gaggcagaag ccacacagag a                                               21

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ctggccgaca gtgcaagac                                                  19

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gacaccaatc tcctcaacga c                                               21

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tcacagacct ccagcatcc                                                  19

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gaagacaacc gccaagaatg                                                 20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
```

```
ggaggagtga ttgacagagg                                              20

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
caagtgtaag tgcccgaaag g                                            21

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ctggctccat acctcttatt gc                                           22

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
attgtcagca atgcatcctg                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
atggactgtg gtcatgagcc                                              20
```

OXYSTEROLS FOR ACTIVATION OF HEDGEHOG SIGNALING, OSTEOINDUCTION, ANTIADIPOGENESIS, AND WNT SIGNALING

This application is a U.S. National Stage of International Application No. PCT/US2008/013319, filed Dec. 3, 2008, which claims the benefit of U.S. Provisional Application No. 60/996,729, filed Dec. 3, 2007, all of which are hereby incorporated by reference herein in their entirety.

This invention was made with Government support of NIH/NIAMS grant RO1AR050426, awarded by the National Institutes of Health. The government has certain rights in the invention.

SEQUENCE LISTING

The instant application contains a Sequence Listing which has been submitted in ASCII format via EFS-Web and is hereby incorporated by reference in its entirety, Said ASCII copy, created on Sep. 13, 2010, is named 58086288.txt and is 3,147 bytes in size.

BACKGROUND

Oxysterols form a large family of oxygenated derivatives of cholesterol that are present in the circulation, and in human and animal tissues. Oxysterols that have been identified in human plasma to date include 7α-hydroxycholesterol, 24S-hydroxycholesterol, and 4α- and 4β-hydroxycholesterol, which are present at concentrations ranging from 5-500 ng/ml. These oxysterols have a variety of half-lives in circulation ranging from 0.5-60 hours, and their levels can be altered by aging, drug interventions, and disease processes. Oxysterols may be formed either by autooxidation, as a secondary byproduct of lipid peroxidation, or by the action of specific monooxygenases, most of which are members of the cytochrome P450 family of enzymes. Examples of these enzymes are cholesterol 7α-hydroxylase (CYP7A1) that forms 7α-hydroxycholesterol, cholesterol 25-hydroxylase that forms 25-hydroxycholesterol, cholesterol 24S-hydroxylase (CYP46) that forms 24S-hydroxycholesterol, and others. In addition, oxysterols may be derived from the diet. Cytochrome P450 enzymes are also involved in the further oxidation of oxysterols and their metabolism into active or inactive metabolites that leads to their eventual removal from the system. Certain oxysterols can have potent effects on cholesterol metabolism. Oxysterols have been found to be present in atherosclerotic lesions. Oxysterols may play a role in various physiologic processes, such as cellular differentiation, inflammation, apoptosis, and steroid production.

Osteoporosis and its complications cause morbidity and mortality in the aging population, and can result from increased bone resorption by osteoclasts in parallel with decreased bone formation by osteoblasts.

SUMMARY

In an embodiment according to the invention, a compound has the formula

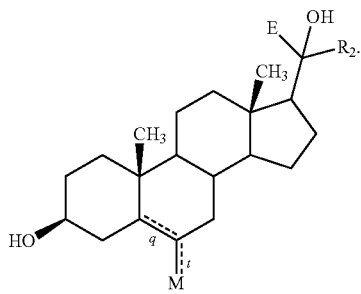

(Formula I)

q can be a single bond or a double bond; and t can be a single bond or a double bond. At least one of q and t can be a single bond. M can be hydrogen (—H), hydroxy (OH), formoxy (—O(C═O)H), acetoxy (—O(C═O)CH$_3$), acyloxy (—O(C═O)-alkyl), oxygen (═O), alkoxy (—O-alkyl), sulfhydryl (—SH), alkylthio (—S-alkyl), amino (—NH$_2$), methylamino (—NHCH$_3$), alkylamino (—NH-alkyl), formamido (—NH(C═O)H), acetamido (—NH(C═O)CH$_3$), and alkylamido (—NH(C═O)-alkyl), with alkyl of from 1 to 6 carbons. When M is oxygen, then t can be a double bond and q can be a single bond. When M is hydrogen, hydroxy, or acetoxy, then t can be a single bond. E can be alkyl of from 1 to 6 carbons, for example, methyl. R$_2$ can be alkane of from 1 to 6 carbons, alkene of from 2 to 6 carbons, alkyne of from 2 to 6 carbons, aralkyl of from 4 to 12 carbons, aralkene from 5 to 12 carbons, aralkyne of from 5 to 12 carbons, halogen-substituted aralkyl of from 4 to 12 carbons, halogen-substituted aralkene from 5 to 12 carbons, halogen-substituted aralkyne of from 5 to 12 carbons, alkyl-substituted aralkyl of from 5 to 18 carbons, alkyl-substituted aralkene from 6 to 18 carbons, alkyl-substituted aralkyne of from 6 to 18 carbons, hydroxy-substituted alkyl of from 1 to 6 carbons, hydroxy-substituted alkene of from 2 to 6 carbons, or hydroxy-substituted alkyne of from 2 to 6 carbons. For example, R$_2$ can be phenalkane of from 7 to 12 carbons, halogen-substituted phenalkane of from 7 to 12 carbons, phenyl-substituted alkene of from 8 to 12 carbons, phenyl-substituted alkyne of from 8 to 12 carbons, thiophene-substituted alkyl of from 5 to 11 carbons, thiophene-substituted alkene of from 6 to 11 carbons, or thiophene-substituted alkyne of from 6 to 11 carbons.

In an embodiment according to the invention, the compound has an activity when contacted with a human or animal cell of stimulating osteoblastic differentiation, inhibiting adipocyte differentiation, stimulating cartilage formation, stimulating hair growth, and/or stimulating angiogenesis.

For example, when q is a double bond, M is hydrogen, and E is methyl, then R$_2$ can be other than ethyl, n-propyl, 4-methylpentyl, 4-methyl-3-pentenyl, 4-methyl-4-pentenyl, and 1-hydroxy-4-methylpentyl. For example, when q is a double bond and M is hydrogen, then R$_2$ can be other than methylbenzyl.

For example, when q is a single bond, M is hydrogen, and E is methyl, then R$_2$ can be other than 4-methylpentyl, vinyl, 1-hydroxy-4-methylpentyl, 3-hydroxy-3-methylbutyl, 4-hydroxy-4-methylpentyl, 1,4-dihydroxy-4-methylpentyl, 1,5- dihydroxy-4-methylpentyl, and 2-phenylethenyl. For example, when q is a single bond, M is hydroxy, and E is methyl, then $R_2$ can be other than 4-methyl-pentyl and 4-methyl-3-pentenyl. For example, when q is a double bond, M is hydrogen, and E is methyl, then $R_2$ can be other than ethyl, n-propyl, n-butyl, n-pentyl, t-butyl, 1-methylpropyl, 3-methylbutyl, 3-methylpentyl, 4-methylpentyl, vinyl, allyl, 1-propenyl, 4-methyl-3-pentenyl, 4-methyl-4-pentenyl, 3-hydroxy-3-methylbutyl, 4-hydroxy-3-methylbutyl, 1-hydroxy-4-methylpentyl, 4-hydroxy-4-methylpentyl, 4-hydroxy-4-methyl-1-pentenyl, 4-hydroxy-4-methyl-2-pentenyl, 1,4-dihydroxy-4-methylpentyl, and 1-(2-pyridinyl)ethyl. For example, when q is a double bond, M is hydrogen, and E is 4-methylpentyl, then $R_2$ can be other than hydroxymethyl. For example, when q is a double bond and M is hydrogen, then $R_2$ can be other than methylbenzyl. For example, when t is a double bond, M is oxygen, and E is methyl, then $R_2$ can be other than 4-methyl-pentyl and 1-hydroxy-4-methylpentyl.

For example, when q is a double bond, M is hydrogen, and $R_2$ is alkane or alkene, then $R_2$ can be

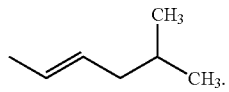

For example, M can be hydroxy and $R_2$ can include

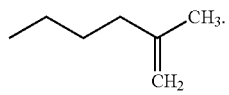

In an embodiment according to the invention, a compound has the formula

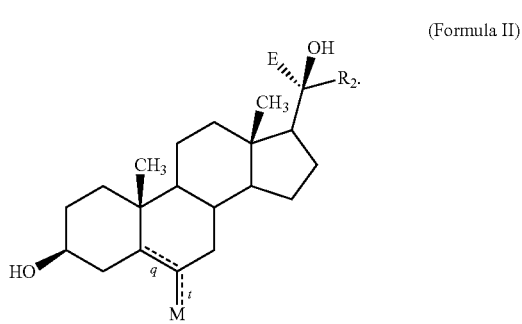

(Formula II)

In an embodiment according to the invention, q is a single bond and t is a single bond. M can be hydroxy, and E can be methyl. $R_2$ can be $R_3$-$R_4$, with $R_3$ being bonded to the two sequentially bonded carbons bonded to the 5-carbon ring. $R_3$ can be alkane of from 1 to 6 carbons, alkene of from 2 to 6 carbons, or alkyne of from 2 to 6 carbons. $R_4$ can be phenyl or thiophene.

In an embodiment according to the invention, q is a double bond. M can be hydrogen, and E can be methyl. $R_2$ can be $R_5$-$R_6$, with $R_5$ being bonded to the two sequentially bonded carbons bonded to the 5-carbon ring. $R_5$ can be alkane of from 1 to 6 carbons, alkene of from 2 to 6 carbons, or alkyne of from 2 to 6 carbons. $R_6$ can be hydrogen, phenyl, halogen-substituted phenyl, thiophene, or hydroxy.

When $R_6$ is hydrogen and $R_5$ is alkane of from 1 to 6 carbons or alkene of from 2 to 6 carbons, then $R_2$ can be

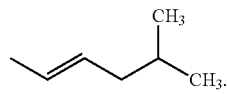

In an embodiment according to the invention q is a single bond and t is a single bond. M can be acetoxy (O(C=O)$CH_3$), and E can be methyl. $R_2$ can be alkane of from 2 to 6 carbons or alkene of from 2 to 6 carbons.

In an embodiment according to the invention q is a single bond and t is a single bond. M can be hydroxy (OH), and E can be methyl. $R_2$ can be alkane of from 2 to 6 carbons, alkene of from 2 to 6 carbons, hydroxy-substituted alkane of from 2 to 6 carbons, or hydroxy-substituted alkene of from 2 to 6 carbons.

In an embodiment according to the invention M can be hydrogen (H), hydroxy (OH), or acetoxy (O(C=O)$CH_3$). When M is hydroxy or acetoxy, then q can be a single bond. When M is hydrogen, then q can be a double bond. $R_2$ can be $R_7$-$R_8$, with $R_7$ being bonded to the two sequentially bonded carbons bonded to the 5 carbon ring. $R_7$ can be selected from the group consisting of alkane of from 1 to 4 carbons, alkene of from 2 to 4 carbons, or alkyne of from 2 to 4 carbons. $R_8$ can be selected from the group consisting of alkane of from 3 to 4 carbons, hydroxy-substituted alkane of from 3 to 4 carbons, alkene of from 3 to 4 carbons, or thiophene. For example, $R_7$ can be 2 single-bonded carbons, 2 double-bonded carbons, or 2 triple-bonded carbons. For example, $R_8$ can be isopropyl, isopropenyl, tert-butyl, hydroxy-substituted isopropyl, hydroxy-substituted isopropenyl, hydroxy-substituted tert-butyl, or thiophene.

In an embodiment according to the invention, a compound can be Oxy50, Oxy51, Oxy52, Oxy53, Oxy20, Oxy22, Oxy26, Oxy27, Oxy39, Oxy40, Oxy42, Oxy28, Oxy41, Oxy48, Oxy49, or Oxy28.

In an embodiment, a bioactive composition or pharmaceutical composition can include an oxysterol compound according to the invention and a pharmaceutically acceptable carrier. In an embodiment, the bioactive composition or pharmaceutical composition can include the compound Oxy34, Oxy36, and/or Oxy38 and a pharmaceutically acceptable carrier. A bioactive composition or pharmaceutical composition can include one or more agents in addition to an oxysterol, for example, parathyroid hormone, sodium fluoride, insulin-like growth factor I (ILGF-I), insulin-like growth factor II (ILGF-II), transforming growth factor beta (TGF-β), a cytochrome P450 inhibitor, an osteogenic prostanoid, BMP 2, BMP 4, BMP 7, and/or BMP 14.

A method for modulating a hedgehog (Hh) pathway mediated response, a Wnt Inhibitory Factor-1 (Wif-1) pathway mediated response, and/or a Wnt pathway mediated response in a cell or tissue, according to the invention, includes contacting the cell or tissue with an effective amount of an oxysterol compound according to the invention. The cell or tissue can be in vitro or in a subject, such as a human, mammal, or animal. For example, the hedgehog (Hh) pathway mediated response can be induced, a Wnt Inhibitory Factor-1 gene can be induced, and/or Wnt pathway related signaling can be activated. For example, the hedgehog (Hh) pathway mediated response can include the stimulation of osteoblastic differentiation, osteomorphogenesis, osteoproliferation, and/or hair growth, and/or the inhibition of adipocyte differentiation, adipocyte morphogenesis, and/or adipocyte proliferation.

A method for treating a subject suffering from a bone disorder, osteoporosis, osteoporitis, osteoarthritis, a bone fracture, obesity, xanthoma formation, a cardiovascular disorder, ateriosclerosis, myocardial infarction, peripheral vascular disease, stroke, and/or alopecia, according to the invention, can include administering to the subject an effective amount of a bioactive composition or pharmaceutical composition comprising an oxysterol compound according to the invention. The subject can be administered the bioactive composition or pharmaceutical composition at a therapeutically effective dose in an effective dosage form at a selected interval to increase bone mass. The subject can be administered the bioactive composition or pharmaceutical composition at a therapeutically effective dose in an effective dosage form at a selected interval to ameliorate the symptoms of osteoporosis. A subject can be treated, for example, to induce bone formation, by harvesting mammalian mesenchymal stem cells, treating the mammalian mesenchymal cells with an oxysterol compound according to the invention to induce osteoblastic differentiation of the cells, and administering the differentiated cells to the subject.

A method for treating a subject suffering from a neurological disorder, according to the invention, can include administering to the subject an effective amount of a bioactive composition or pharmaceutical composition comprising an oxysterol compound according to the invention.

In an embodiment according to the invention, an implant for use in a human or animal body includes a substrate having a surface. The surface of the implant can include a bioactive composition or pharmaceutical composition comprising an oxysterol compound according to the invention in an amount sufficient to induce bone formation in the surrounding bone tissue.

DETAILED DESCRIPTION

Figure 1A:
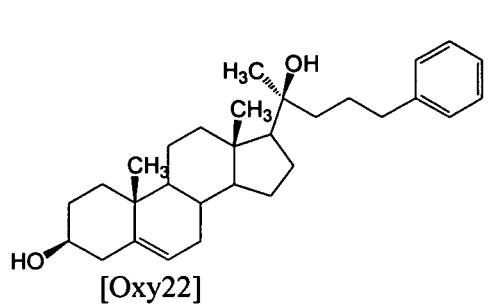
FIG. 1 presents the chemical structures of oxysterol compounds designated as Oxy22, Oxy26, Oxy27, Oxy28, Oxy39, Oxy40, Oxy41, Oxy42, Oxy48, Oxy49, Oxy20, Oxy34, Oxy36, Oxy38, Oxy50, Oxy51, Oxy52, and Oxy53.
Figure 1A:
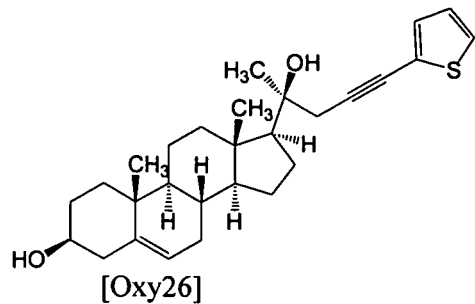
Figure 1A:
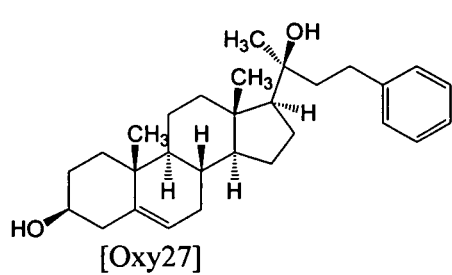
Figure 1A:
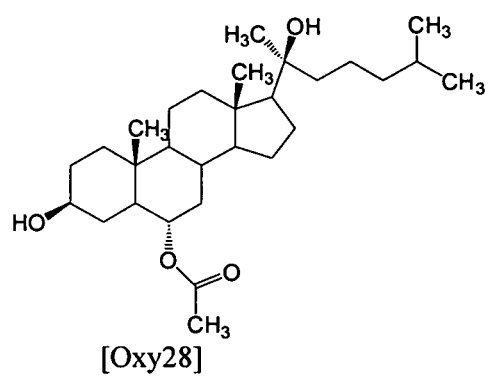
Figure 1A:
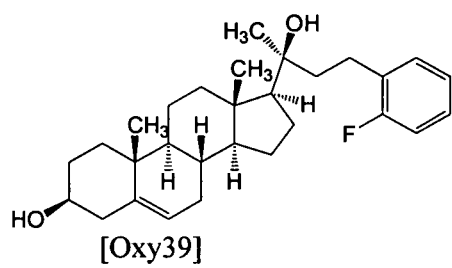
Figure 1A:
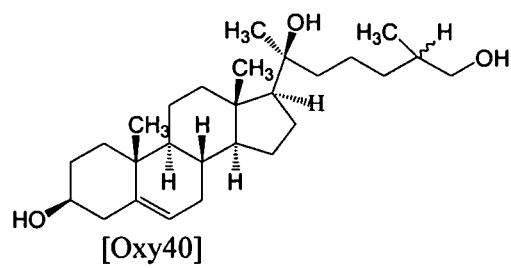
Figure 1B:
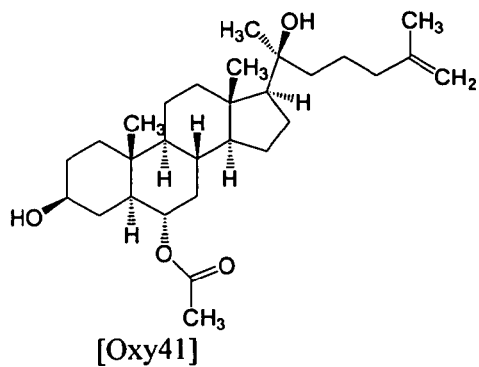
Figure 1B:
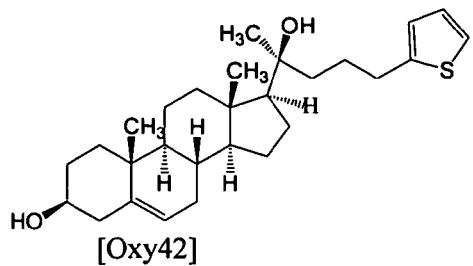
Figure 1B:
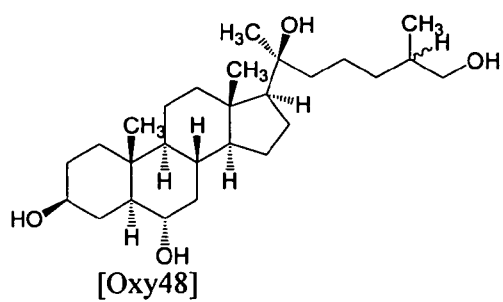
Figure 1B:
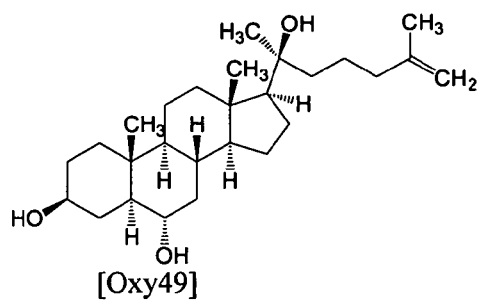
Figure 1B:
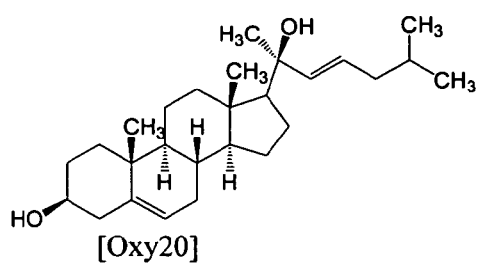
Figure 1B:
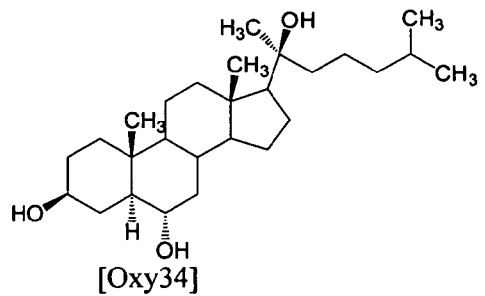
Figure 1C:
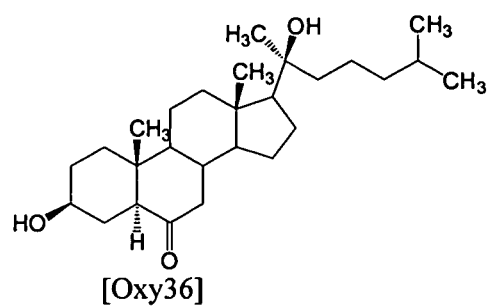
Figure 1C:
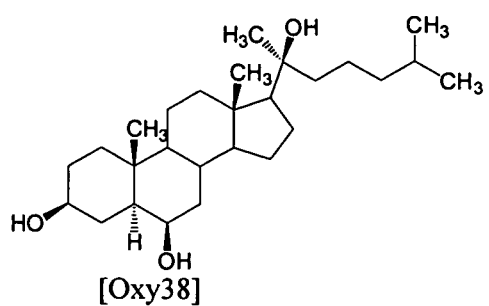
Figure 1C:
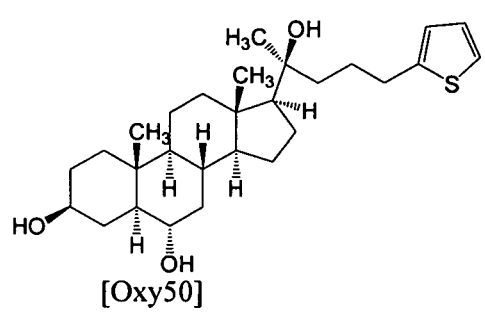
Figure 1C:
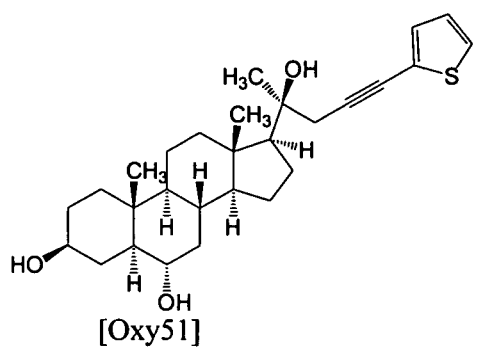
Figure 1C:
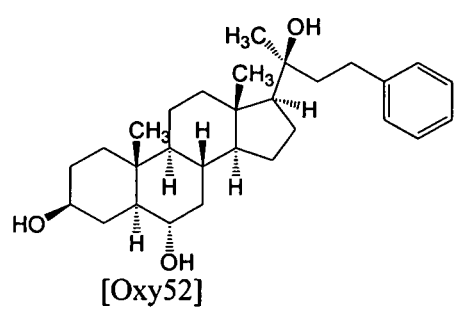
Figure 1C:
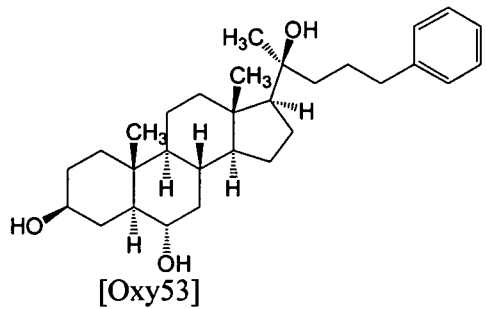

Embodiments of the invention are discussed in detail below. In describing embodiments, specific terminology is employed for the sake of clarity. However, the invention is not intended to be limited to the specific terminology so selected. A person skilled in the relevant art will recognize that other equivalent parts can be employed and other methods developed without parting from the spirit and scope of the invention. All references cited herein are incorporated by reference in their entirety as if each had been individually incorporated. Patent Cooperation Treaty (PCT) international applications published as WO/2008/115469, WO/2008/082520, WO/2007/098281, WO/2007/028101, WO/2006/110490, WO/2005/020928, and WO/2004/019884 are hereby incorporated by reference in their entirety.

In this text, "aralkyl" can mean a chemical functional group in which an aryl ring is bound to an alkyl group. "Aralkene" can mean a chemical functional group in which an aryl ring is bound to an alkene group. "Aralkyne" can mean a chemical functional group in which an aryl ring is bound to an alkyne group. An "aryl" group can mean a chemical functional group including one or more rings, of which at least one ring is aromatic. The ring or rings may be formed of carbon atoms or may be heterocyclic. Examples of aryl rings include a benzene ring, a naphthalene, pyridine, pyrrole, thiophene, furan, oxazole, thiazole, imidazole, indole, and quinoline. In an embodiment, the aryl ring may be substituted, for example, by halogen, alkyl (e.g., methyl), amine, hydroxy, and/or sulfhydryl.

Oxysterols can play a role in cellular differentiation. Specific oxysterols induce the differentiation of human keratinocytes in vitro, while monocyte differentiation can be induced by the oxysterol 7-ketocholesterol. Differentiation of keratinocytes by oxysterols is mediated by the nuclear hormone receptor, liver X receptor β (LXRβ). LXRα and LXRβ, initially identified as orphan nuclear receptors, act as receptors for oxysterols. However many of the effects of oxysterols are mediated by LXR-independent mechanisms. These include their effects on mesenchymal cells, since activation of LXR by specific LXR ligands inhibited, rather than stimulated, the osteogenic differentiation of mesenchymal cells. Furthermore, MSC derived from LXR null mice were able to respond to osteogenic oxysterols as well as their wild type counterparts. Additional oxysterol binding proteins have been reported that can regulate the activity of signaling molecules such as mitogen-activated protein kinase (MAPK).

Hedgehog molecules can play roles in a variety of processes including tissue patterning, mitogenesis, morphogenesis, cellular differentiation and embryonic developments. In addition to its role in embryonic development, hedgehog signaling can play a role in postnatal development and maintenance of tissue/organ integrity and function. Hedgehog signaling can be important during skeletogenesis as well as in the development of osteoblasts in vitro and in vivo. Hedgehog signaling can inhibit adipogenesis when applied to pluripotent mesenchymal cells, C3H-10T 1/2.

Hedgehog signaling can involve a complex network of signaling molecules that includes plasma membrane proteins, kinases, phosphatases, and factors that facilitate the shuffling and distribution of hedgehog molecules. Production of hedgehog molecules from a subset of producing/signaling cells involves its synthesis, autoprocessing and lipid modification. Lipid modification of hedgehog, which may be essential for its functionality, can involve the addition of a cholesterol molecule to the C-terminal domain of the auto-cleaved hedgehog molecule and palmitoylation at its N-terminal domain. Additional accessory factors can help shuttle hedgehog molecules to the plasma membrane of the signaling cells, release them into the extracellular environment, and transport them to the responding cells.

In the absence of hedgehog molecules, Patched (Ptch), present on the plasma membrane of the responding cells, can keep hedgehog signaling in a silent mode by inhibiting the activity of another plasma membrane associated signal transducer molecule, Smoothened (Smo). In the presence of hedgehog, the inhibition of Smo by Ptch can be alleviated and Smo can transduce the signal for the regulation of transcription of hedgehog-regulated genes. This transcriptional regulation in part can involve the Ci/Gli transcription factors that enter the nucleus from the cytoplasm after an interaction between the members of a complex of accessory molecules that regulate Gli and its conversion from a 75 kd transcriptional repressor to a 155 kd transcriptional activator (63).

Pluripotent mesenchymal stem cells found in the bone marrow stroma, also known as bone marrow stromal cells (MSC), have the potential to differentiate into several different cell types including osteoblasts, chondrocytes, myocytes, fibroblasts, and adipocytes (1-3). Regulation of stem cell fate down these various lineages is important for tissue development, homeostasis and repair (4, 5). Osteoporosis is a degenerative disease of the skeleton that generally occurs due to an alteration in bone turnover homeostasis and is characterized by fragile bones and increased susceptibility to bone fractures (6). Decreased bone synthesis due to reduced osteoblast formation and/or activity of progenitor cells, which occurs in parallel with increased adipocyte formation at the expense of osteoblasts, in addition to increased bone resorption from excessive osteoclast formation and/or activity are mechanisms leading to this degenerative disorder (7). In addition to anti-resorptive agents, therapeutic molecules having pro-osteogenic and anti-adipogenic effects on MSC may help intervene with osteoporosis by enhancing bone formation through a shift in the apparent imbalance in cellular differentiation in favor of osteoblasts (8-10).

Oxysterols are products of cholesterol oxidation and are formed in vivo by a variety of cell types including osteoblasts (11, 12). Certain oxysterols, such as 20(S)-hydroxycholesterol (20S), alone or in combination with, 22(S)- or 22(R)-hydroxycholesterol, can be potent inducers of osteogenic differentiation in pluripotent mesenchymal cells such as M2-10B4 (M2) marrow stromal cells and C3H10T1/2 embryonic fibroblasts (13). These oxysterols can induce osteogenic and inhibit adipogenic differentiation of MSCs through activation of the hedgehog signaling pathway, which in turn regulates the master switches that control osteogenic and adipogenic differentiation, namely Runx2 and PPARγ, respectively (14-16). Oxysterols may be able to serve as potential therapeutics for intervention with osteoporosis and other musculoskeletal disorders. Certain mechanisms may play a synergistic and/or cooperative role with hedgehog signaling in mediating the effects of osteogenic oxysterols on MSC differentiation.

Wnts are small (39-46 kDa) lipid-modified secreted glycoproteins that influence many aspects of embryological development, such as cell patterning, proliferation, and stem cell fate determination (17-19). Wnt proteins signal through Frizzled (Fz) molecules, which are a family of seven-pass transmembrane receptors that transduce the signal through either β-catenin-dependent (i.e., canonical β-catenin/TCF/Lef pathway) or independent (i.e, non-canonical Wnt/planar cell polarity and the Wnt/calcium pathways) mechanisms. Activation of the β-catenin-dependent pathway requires the presence of low-density lipoprotein receptor related protein (LRP)5/6 (20). Certain Wnts induce osteogenesis, through direct stimulation of Runx2 gene expression (21, 22), and inhibit adipogenesis by inhibition of PPARγ and C/EBPα (23, 24). Furthermore, humans loss of function mutations in the LRP5 gene results in the osteopenic disorder osteoporosis-pseudoglioma syndrome (25), whereas gain of function mutations in this same gene results in high bone mass disorders (26). It is possible to specifically inhibit the β-catenin-dependent Wnt signaling pathway using the protein Dickkopf-1 (Dkk-1), which directly binds to and removes LRP5/6 from the cell surface though endocytosis, thereby preventing β-catenin-dependent Wnt signaling from occurring (22, 27). Although classically thought to specifically act as an inhibitor of β-catenin dependent Wnt signaling, several reports have shown the inhibitory effects of Dkk-1 independent of β-catenin (28, 29). Hedgehog and Wnt signaling act synergistically and/or cooperatively in regulating several physiologic and pathologic processes including osteoblast development, and hair follicle morphogenesis (30-33).

The PI3-kinase/Akt pathway is involved in a variety of cellular processes including cell growth, proliferation, survival, metabolism, invasion, angiogenesis, and DNA repair. The PI3-kinase/Akt pathway can play a role in the survival of uncommitted osteoblast precursor cells (34, 35) and in the regulation of osteoblast differentiation and migration (36-38). Akt−/− mice have severely delayed bone development (39), and specific deletion of Akt inhibitor, Pten phosphatase, in osteoblasts results in increased bone density throughout life in mice (40). PI3-kinase/Akt activation may play a direct or synergistic role in mediating the biological effects of hedgehog signaling including cell cycle progression, neuronal and chondrogenic differentiation, and capillary morphogenesis by endothelial cells (41-44).

Certain oxysterols can exert their osteogenic effects through a Dkk-1 inhibitable and PI3-kinase-dependent mechanism(s). Although Dkk-1 is able to block the oxysterol-induced osteogenic differentiation of MSC, oxysterols appear to regulate some but not all targets of Wnt signaling.

To improve bone health, osteoprogenitor cells can be targeted in order to stimulate their osteogenic differentiation and bone forming properties through the use of osteoinductive/anabolic factors. Certain naturally-occurring oxysterols have osteoinductive properties, mediated in part through activation of hedgehog signaling in osteoprogenitor cells. In parallel to activating the hedgehog signaling pathway, osteogenic oxysterols can activate the Wnt-related signaling pathway through a Dkk-1-inhibitable and β-catenin independent manner. Bone marrow stromal cells treated with oxysterols can demonstrate increased expression of osteogenic differentiation markers, along with selective induced expression of Wnt target genes. These oxysterol effects, which can occur in the absence of β-catenin accumulation or TCF/Lef activation, can be inhibited by the hedgehog pathway inhibitor, cyclopamine, and/or by the Wnt pathway inhibitor, Dkk-1. The inhibitors of PI3-Kinase signaling, LY 294002 and wortmanin, can inhibit oxysterol-induced osteogenic differentiation and induction of Wnt signaling target genes. Osteogenic oxysterols are small molecule modulators of signaling pathways in pluripotent mesenchymal cells that regulate numerous developmental and post-developmental processes.

It has been demonstrated that bone formation in vivo in a rat calvarial defect model can be enhanced when the defects are implanted with a carrier PLGA disc containing osteogenic oxysterols 20S-hydroxycholesterol+22S-hydroxycholesterol. This finding demonstrated that osteogenic oxysterols that induce osteogenic differentiation of osteoprogenitor cells, for example bone marrow stromal cells, in vitro also stimulate osteogenic activity of cells in vivo and enhance bone healing (74).

The oxysterols presented herein can be useful in creating new therapeutic formulations for induction of bone formation, treatment of osteoporosis, and for other indications. These oxysterols can have a lower cost of synthesis/production as well as better safety and activity profiles than conventional compounds presently used to induce bone formation and treat osteoporosis. Such applications can be based on the ability of these oxysterols to induce the hedgehog signaling pathway. Certain oxysterols can target pluripotent cells to induce their lineage specific differentiation into various cell types, for example, osteoblasts, due to the induction of hedgehog signaling in these cells. Mesenchymal stem cells treated with these compounds can show induced expression of markers of osteoblast differentiation. In this study, oxysterols have been synthesized and tested in vitro for activation of hedgehog signaling pathway in pluripotent mesenchymal cells and induction of markers of osteogenic differentiation. Certain oxysterols can inhibit adipogenic differentiation of similar cells and/or can induce Wnt related signaling. The oxysterols presented herein can be used in therapeutic formulations for various indications including but not limited to induction of local bone formation, treatment of osteoporosis, and anti-obesity applications. Other indications that are applicable based on the hedgehog pathway activating property of these molecules are 1) cardiovascular diseases including, but not limited to, arteriosclerosis, angina pectoris, myocardial infarction, and stroke, 2) hair growth/alopecia, and 3) cartilage formation.

Oxysterols discussed in this application include those designated as Oxy22, Oxy26, Oxy27, Oxy28, Oxy39, Oxy40, Oxy41, Oxy42, Oxy48, Oxy49, Oxy20, Oxy34, Oxy36, Oxy38, Oxy50, Oxy51, Oxy52, and Oxy53. The chemical structures of these molecules is presented in FIG. 1 (64, 65). At least the following oxysterols have been identified as osteoinductive: Oxy22, Oxy26, Oxy27, Oxy28, Oxy39, Oxy40, Oxy41, Oxy42, Oxy48, Oxy49, Oxy50, Oxy51, Oxy52, and Oxy53. The osteoinductive properties of these oxysterols is shown by their ability to induce the expression of various osteoblast differentiation markers, including alkaline phosphatase activity, osteocalcin mRNA expression, and mineralization. These oxysterols are activators of the hedgehog signaling pathway. These oxysterols also inhibit adipogenesis of pluripotent cells.

An oxysterol compound according to the invention can have an activity, that is, can induce a biological response, when contacted with a human or animal cell. For example, the cell can be a mesenchymal stem cell or a bone marrow stromal cell. This activity or response can be correlated with stimulating osteoblastic differentiation, inhibiting adipocyte differentiation, stimulating cartilage formation, stimulating hair growth, and/or stimulating angiogenesis. A bioactive composition, for example, a pharmaceutical composition including a pharmaceutically acceptable carrier and an oxysterol compound according to the invention can have an activity, that is, can induce a biological response, when administered to a mammalian cell, for example, a cell in vitro or a cell in a human or an animal. This activity or response can be correlated with stimulating osteoblastic differentiation, inhibiting adipocyte differentiation, stimulating cartilage formation, stimulating hair growth, and/or stimulating angiogenesis. Such an activity or response can arise from stimulation of the hedgehog pathway. For example, such an activity or response of an oxysterol compound according to the invention can be characterized by one or more of the following when the oxysterol compound is administered to a cell, a human, a mammal, or an animal: osteocalcin, Gli1, Patched, bone sialoprotein, Axin2, Cyclin D1, Nkd2, and/or WIF-1 mRNA expression above that observed for a control; adipocyte growth less than that observed for a control (the oxysterol compound according to the invention and any control compound each administered with Troglitazone); Gli induced reporter activity above that observed for a control, TCF/Lef reporter activity above that observed for a control; and/or $^{45}$Ca incorporation and/or alkaline phosphatase activity above that observed for a control. The control can be, for example, an untreated cell, in vitro or in a human or animal, such as a mammal. Alternatively, the control can be a cell to which a control compound has been administered. For example, such a control compound can be a vehicle, a pharmaceutically acceptable carrier, a naturally occurring or synthetic oxysterol, and/or another compound. A biological response may be identified via a cell-level laboratory assay, such as an assay discussed herein, including measurements of various types of protein expression and other activity. According to the invention, these biological responses are considered to be "correlated with" desirable tissue-level pharmaceutical effects identified herein, such as stimulating osteoblastic differentiation, inhibiting adipocyte differentiation, stimulating cartilage formation, stimulating hair growth, and/or stimulating angiogenesis. "Above that observed" and "less than that observed" refers to a statistically significant difference, for example, with $p<0.05$.

The induction of BSP expression may be important for the maximal potency of oxysterols, such as the Oxy compounds discussed herein, to induce mineralization in cultures of M2-1084 cells. Induction of BSP expression may be important for the osteoinductive property of oxysterol molecules. Based on structure-activity relationship (SAR) studies we performed, for example, experiments discussed herein, it appears that the osteoinductive potential of the oxysterols may increase when a double bond is added between the 25-carbon and the 27-carbon of 20(S)-hydroxycholesterol. For example, the osteoinductive potential of an oxysterol may be increased if it has a double bond between the 25-carbon and the 27-carbon and/or a hydroxy group pendant from the 6-carbon of the B-ring, such as Oxy49.

Thus, some applications of oxysterols discussed herein include the following. An oxysterol can be used to activate the hedgehog pathway in order to target any cell, organ, or tissue in humans and/or animals for an indication that would benefit from the activation of the hedgehog pathway. An oxysterol can be used to induce systemic bone formation to treat a disorder such as osteoporosis, to induce local bone formation to treat conditions such as non-union fractures, and bone defects of any sort, such as calvarial bone or jaw bone defects in dental applications/implants, and to induce spinal fusion. An oxysterol can be used alone or in combination with one or more bone morphogenetic proteins and other osteoinductive and osteoconductive molecules. A combination of different oxysterols can be used. An oxysterol can be used to inhibit systemic fat formation to treat a condition such as obesity, and can be used to inhibit local fat formation to treat a conditions such as a xanthoma. An oxysterol can be used to induce the formation of cartilage, for example, by activating the hedgehog pathway, when used alone or in combination with other inducers of chondrocyte differentiation. For example, the used of an oxysterol to induce the formation of cartilage can be used to treat a condition such as osteoarthritis or in the repair of normal wear and tear of joints. An oxysterol can be used to treat a cardiovascular condition, for example, a condition that may benefit from increased hedgehog pathway activity resulting in protective effects on cells of all origin, including neural and vascular, in indications such as, but not limited to, stroke, myocardial infarction, arteriosclerosis, and peripheral vascular disease. An oxysterol can be used to induce new blood vessel formation and/or angiogenesis, for example, by activating the hedgehog pathway. An oxysterol can be used to induce hair growth to treat alopecia. An oxysterol can be used to induce Wif-1 (Wnt Inhibitory Factor-1) in any cell type of human or animal origin. An oxysterol can be used to activate Wnt pathway related signaling in any cell type of human or animal origin.

Oxysterol-Induced Osteogenesis is Inhibited by the Wnt Signaling Inhibitor, Dickkopf-1 (Dkk-1)

Figure 2A:
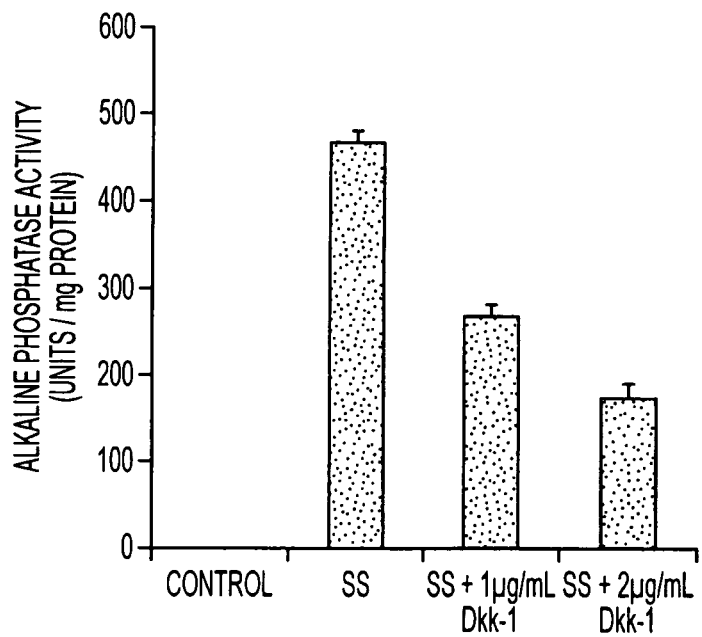
FIG. 2 shows how the LRP5/6 inhibitor, Dickkopf-1 (Dkk-1), inhibits oxysterol-induced osteogenic differentiation in marrow stromal cells.
Figure 2B:
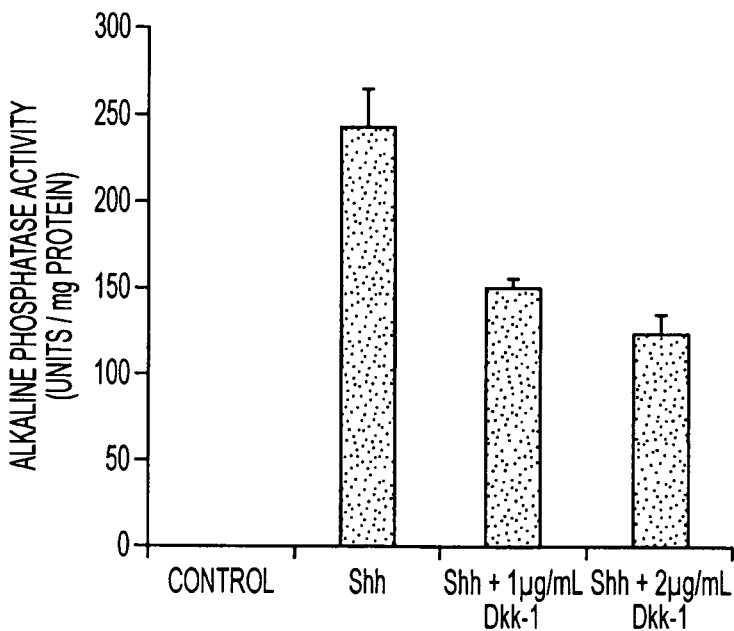
Figure 2C:
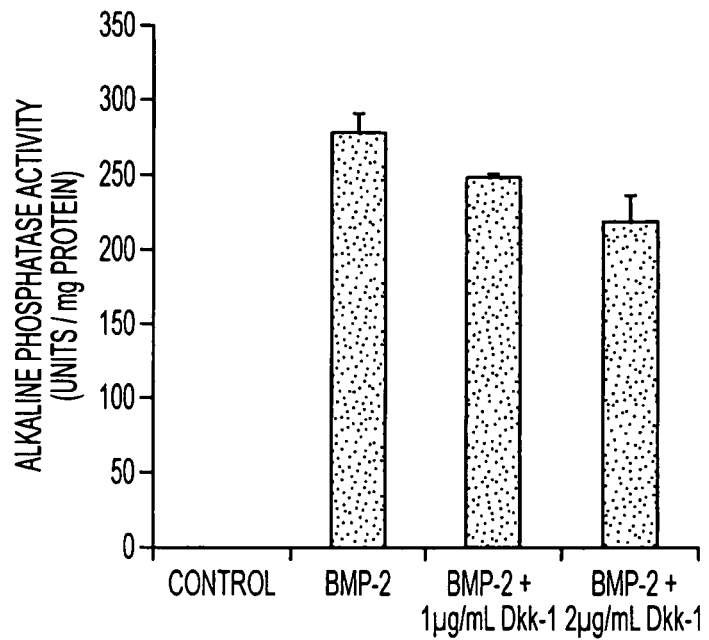
Figure 2D:
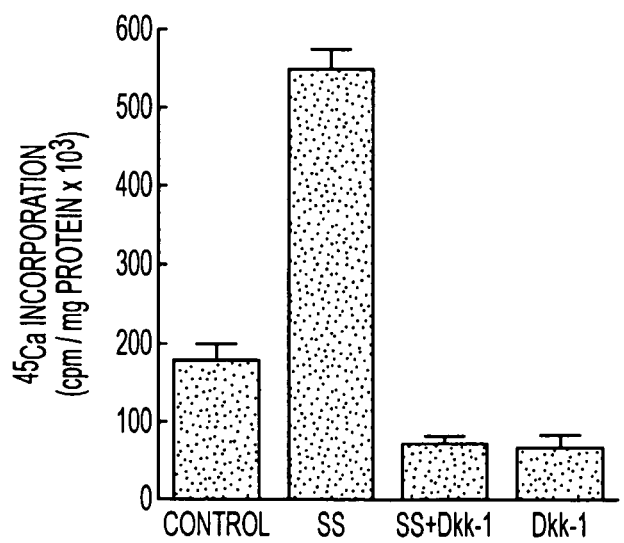
Figure 2E:
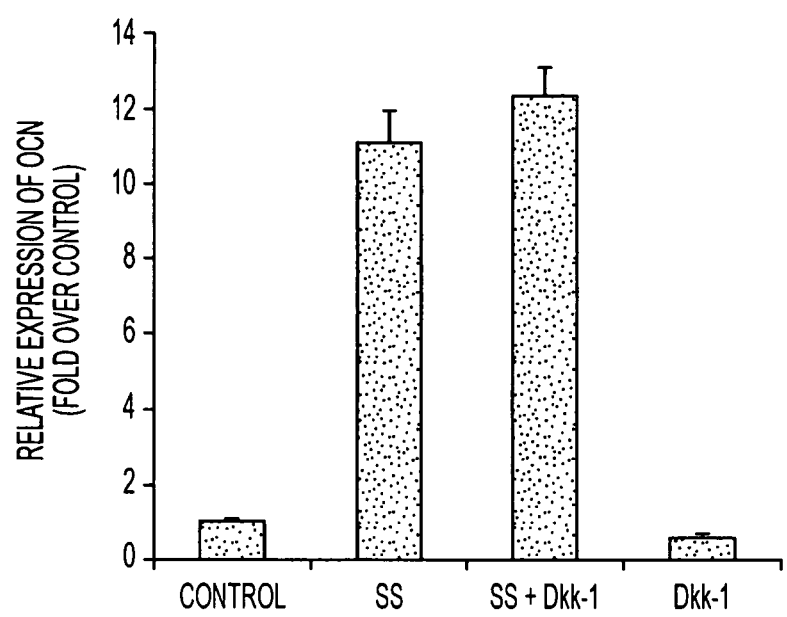

We examined the possible role of Wnt signaling in oxysterol-induced osteogenic differentiation of MSC (mesenchymal stem cells) by treating M2 cells with Dkk-1. Several markers of osteogenic differentiation were analyzed, including alkaline phosphatase (ALP) activity, osteocalcin (OCN) mRNA expression, and mineralization. Pre-treatment with Dkk-1 caused a partial but significant inhibition of oxysterol-induced ALP activity in M2 cells (FIG. 2A); Dkk-1 alone had no observed effect. To assess if the observed inhibition of ALP activity using Dkk-1 was specific to oxysterols, we examined the effect Dkk-1 pre-treatment had on other osteoinductive factors, namely sonic hedgehog (Shh) and bone morphogenetic protein-2 (BMP-2). As with oxysterol-induced ALP activity, Dkk-1 pre-treatment partially inhibited Shh-induced ALP activity (FIG. 2B). However, BMP-2-induced ALP activity was only significantly inhibited by using the higher concentration of Dkk-1, and to a lesser extent than that achieved for oxysterol- and Shh-induced ALP activity despite similar levels of ALP activity induction by all three molecules (FIG. 2C). Complete and below baseline level inhibition of oxysterol-induced mineralization in M2 cells pretreated with Dkk-1 was observed (FIG. 2D). Dkk-1 did not inhibit oxysterol-induced OCN mRNA expression in M2 cells (FIG. 2E), and did not inhibit oxysterol-induced Runx2 DNA binding activity assessed by EMSA analysis.

Osteogenic Oxysterols Selectively Regulate Targets of Wnt Signaling

Figure 3A:
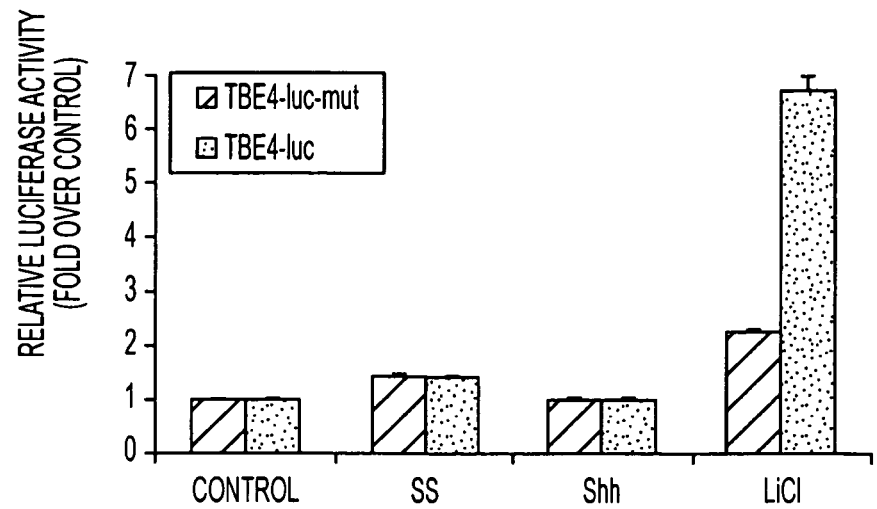
FIG. 3 shows the effect of osteogenic oxysterols on TCF/Lef transcriptional activity in marrow stromal cells.
Figure 3B:
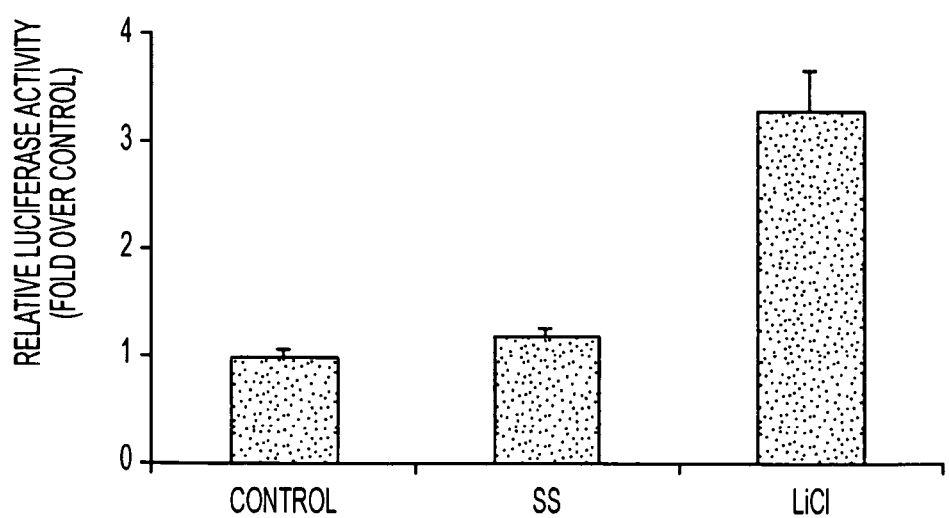

To demonstrate the role of Wnt signaling in oxysterol-induced biological effects in M2 cells, we examined the effects of oxysterols on several markers of Wnt signaling, including TCF/Lef-mediated transcriptional activity, cytosolic accumulation of β-catenin, and induced expression of several known Wnt target genes. Transcriptional activity of TCF/Lef in M2 cells treated with 5 µM SS, 200 ng/ml Shh, or 40 mM lithium chloride (LiCl) was measured using a luciferase reporter containing 4 wild-type or mutant TCF/Lef binding sites (47). No significant change in reporter activity was observed in SS- or Shh-treated cells compared to untreated control cells after 24 hours, whereas the positive control, LiCl, significantly induced TCF/Lef reporter activity (FIG. 3A). Reporter activity was not induced after 48 or 72 hours of treatment with oxysterols or Shh. Similar results were obtained when we used a different TCF/Lef reporter construct containing a Cyclin D1 promoter element, which has a TCF/Lef binding site (48) and was activated by LiCl, but not oxysterols, after 24 hours of treatment (FIG. 3B). LiCl had no effect on pGL3basic luciferase control reporter (48). Cytosolic extracts from M2 cells treated for 8, 24, and 48 hours with 5 µM SS showed no significant change in β-catenin levels as measured by Western blot analysis and normalized to β-actin levels.

Figure 4A:
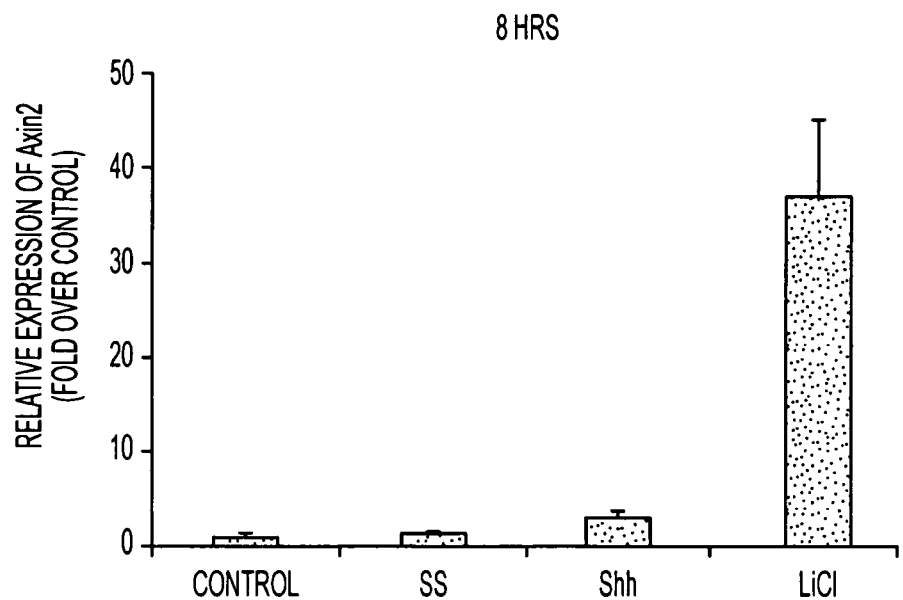
FIG. 4 shows how osteogenic oxysterols differentially regulate Wnt target gene expression in marrow stromal cells.
Figure 4B:
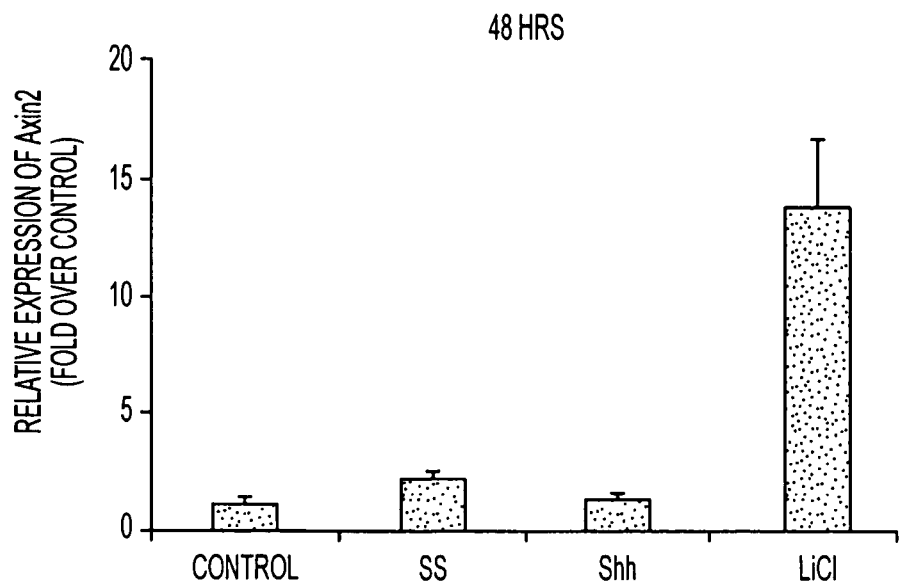
Figure 4C:
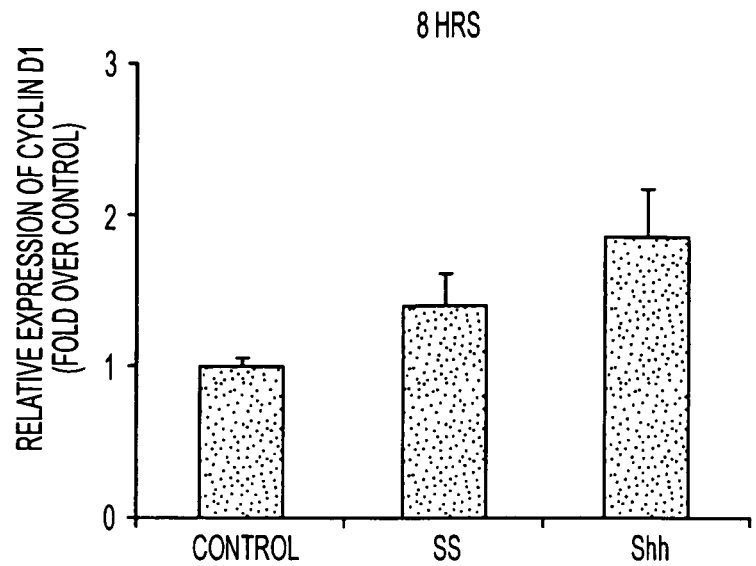
Figure 4D:
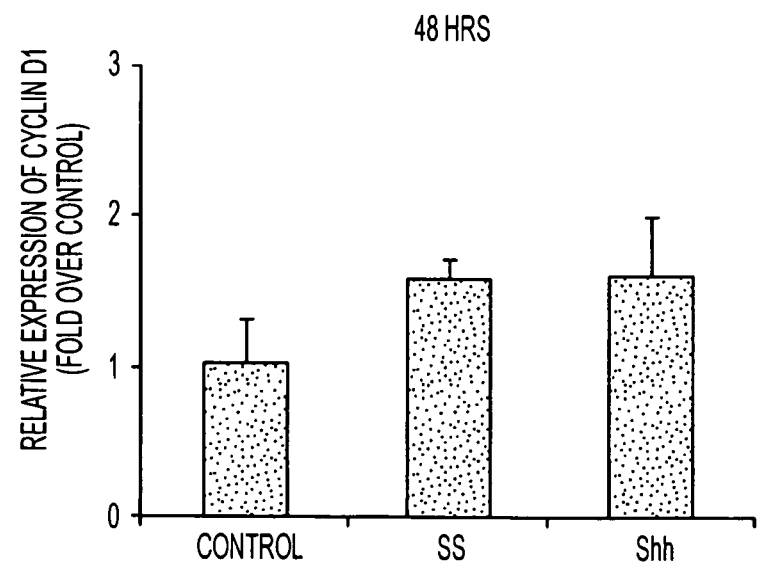
Figure 4E:
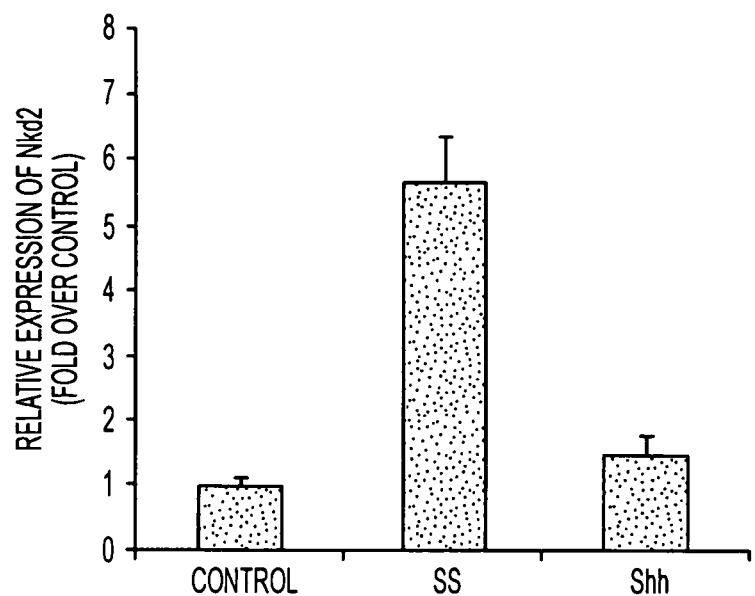
Figure 4F:
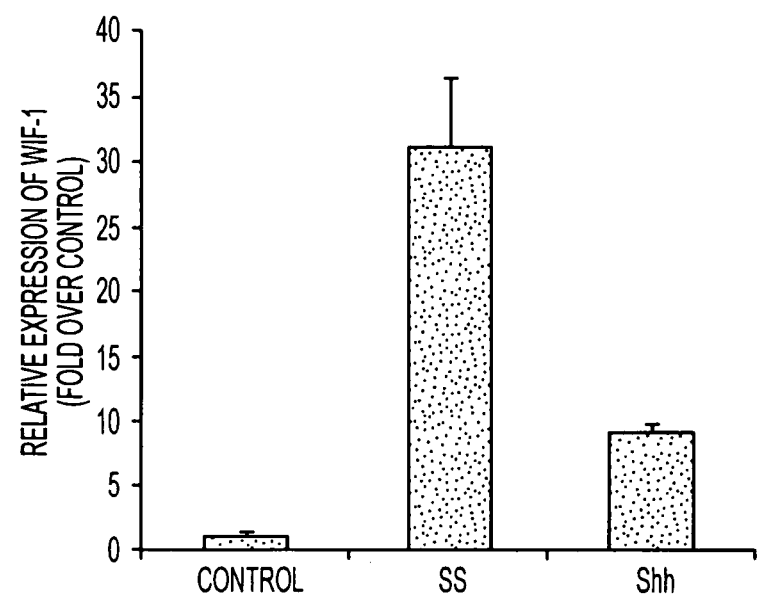
Figure 5A:
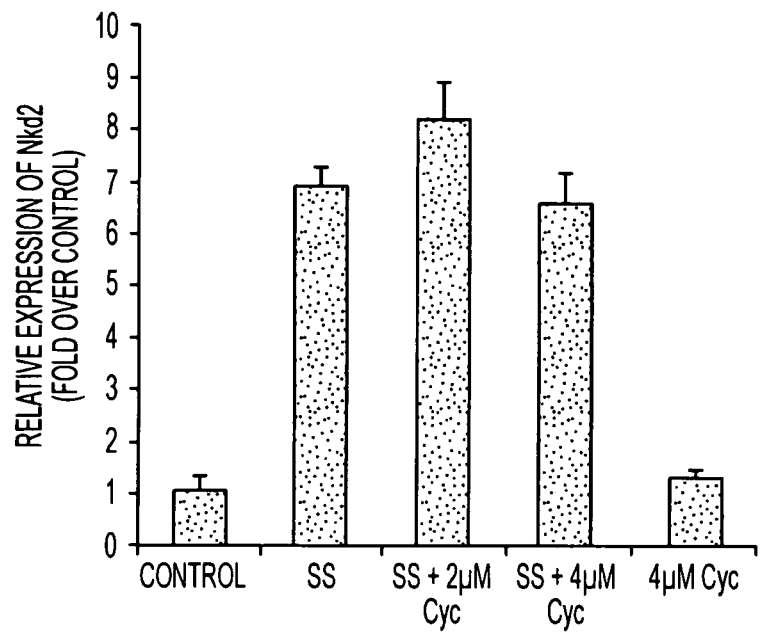
FIG. 5 shows the effects of various inhibitors on oxysterol-induced Nkd2 and Wif-1 expression in marrow stromal cells.
Figure 5B:
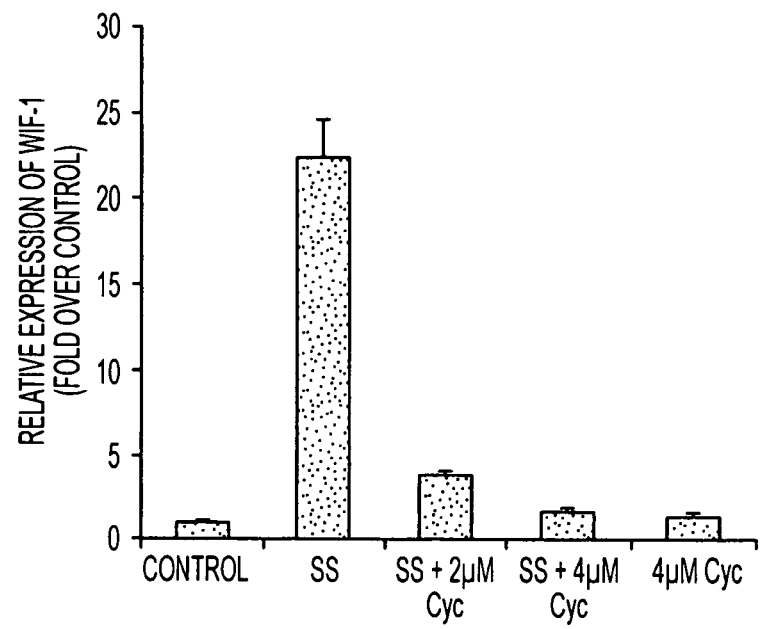
Figure 5C:
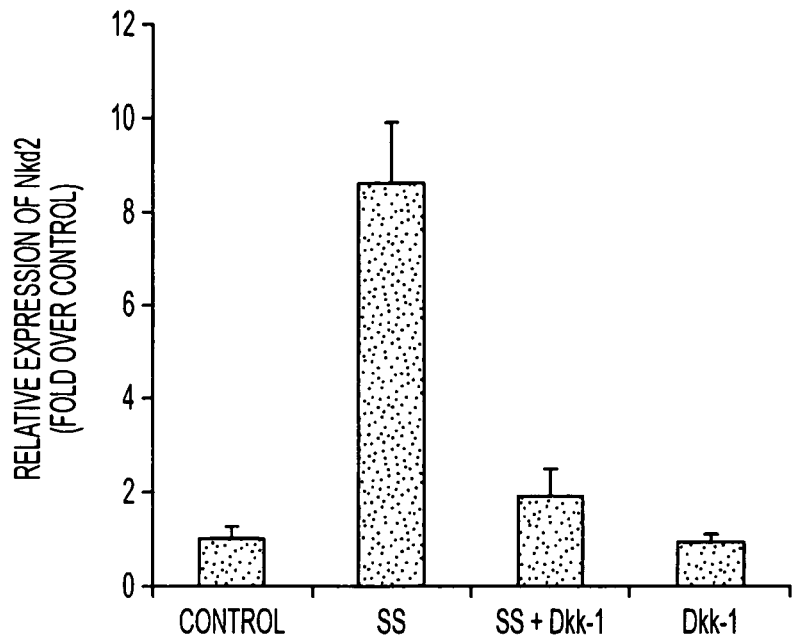
Figure 5D:
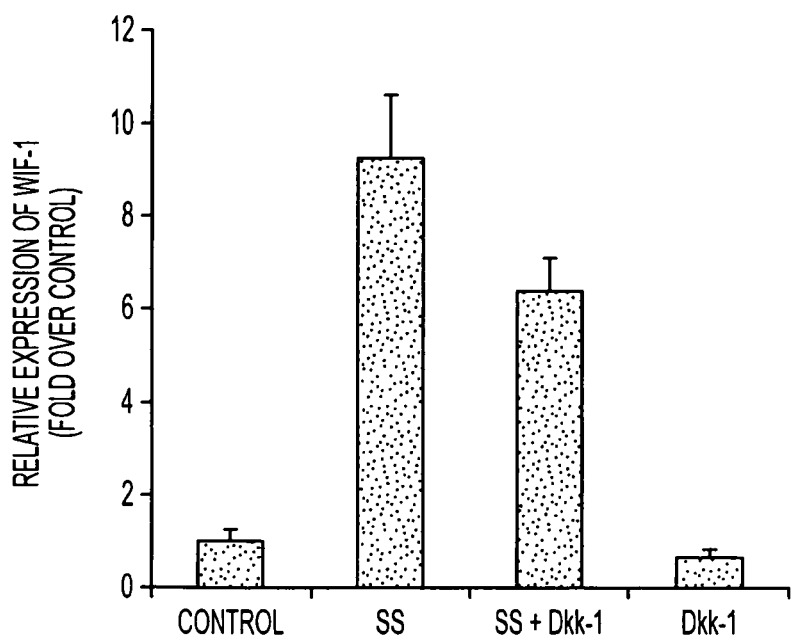
Figure 5E:
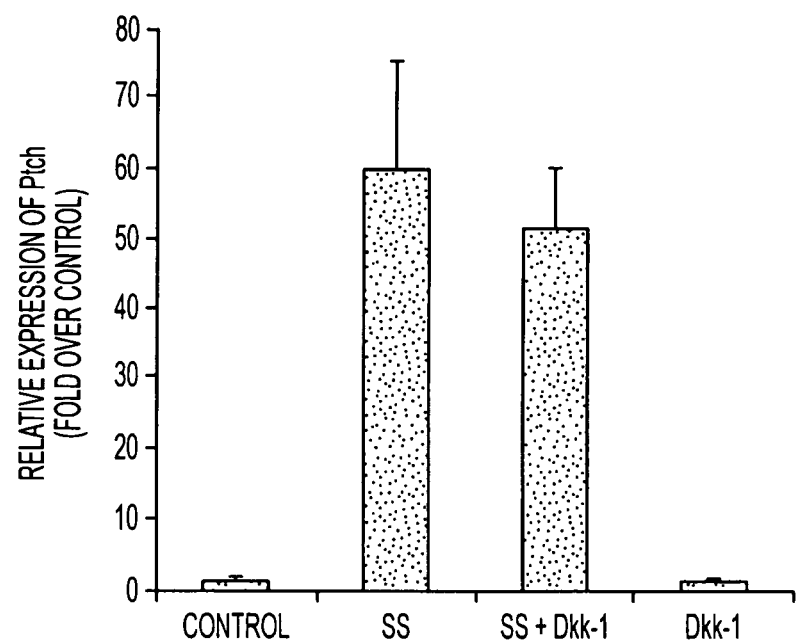

In addition to the TCF/Lef reporter assays and Western blots of β-catenin described above, we also examined the effect of osteogenic oxysterols on the expression of several genes that are known targets of Wnt signaling, namely Axin2, Cyclin D1, Naked Cuticle 2 (Nkd2) and Wnt Inhibitory factor-1 (Wif-1) (48-52). Results showed no significant change in Axin2 mRNA expression upon treatment of M2 cells with 5 µM SS or 200 ng/ml Shh after 8 and 48 hours, whereas LiCl induced its expression at both time points (FIGS. 4A and 4B). Oxysterols did not significantly induce Cyclin D1 mRNA expression, whereas Shh did cause a small but significant increase in its expression after 8 hours, but not 48 hours, of treatment (FIGS. 4C and 4D). LiCl did not induce the expression of Cyclin D1 in M2 cells at 8 hours and inhibited its baseline expression after 48 hours. mRNA expression of both Nkd2 and Wif-1, which are Wnt target genes that antagonize canonical Wnt signaling (50-52), were significantly induced by oxysterols 6 and 30 fold, respectively, after 48 hours (FIGS. 4E and 4F), but not after 8 hours. Shh treatment induced Wif-1, but not Nkd2 expression (FIGS. 4E and 4F). As anticipated from the inability of Shh to induce Nkd2 expression, the Hh pathway inhibitor, cylcopamine, at concentrations that completely abolished the induced expression of Hh target gene, Patched (Ptch), did not inhibit oxysterol-induced Nkd2 expression (FIG. 5A). In contrast, oxysterol-induced Wif1 expression was completely blocked by cyclopamine (FIG. 5B). Oxysterol-induced Nkd2 expression was almost completely inhibited by Dkk-1 (FIG. 5C), whereas oxysterol-induced Wif1 was only minimally inhibited (FIG. 5D). To assess whether Wnt pathway activation might regulate oxysterol-induced Hh pathway activity, we tested the effect of Dkk-1 on oxysterol-induced Ptch mRNA expression, and found that Dkk-1 did not inhibit Ptch expression (FIG. 5E).

Wnt3a Inhibits Osteogenic Differentiation of M2-10B4 Marrow Stromal Cells

Figure 6A:
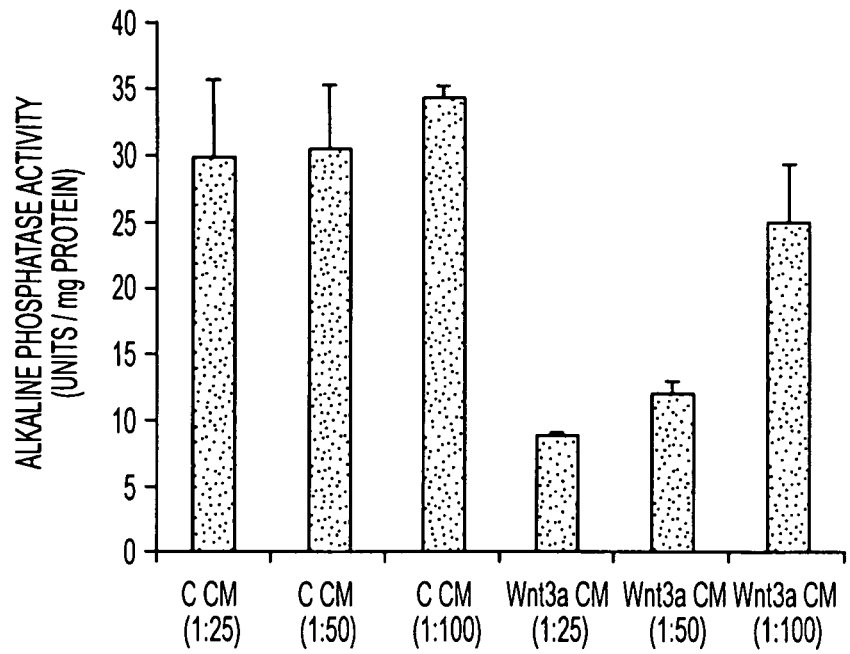
FIG. 6 shows how Wnt3a conditioned medium inhibits oxysterol-induced alkaline phosphatase activity in marrow stromal cells.
Figure 6B:
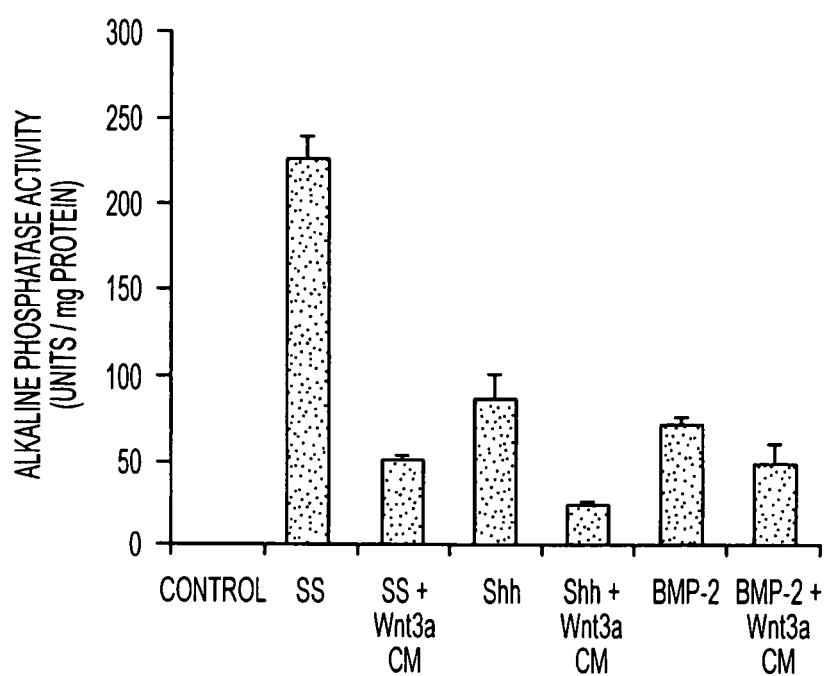

To examine the effect of Wnt signaling on osteogenic differentiation of M2 cells, we tested the effect of Wnt3a conditioned medium (CM) on ALP activity compared to control CM (C CM). M2 cells were treated in osteogenic medium for 6 days with either C CM or Wnt3a CM at 1:25, 1:50, or 1:100 dilutions. Spontaneous increase in ALP activity that is normally seen as M2 cells differentiate in osteogenic medium was inhibited by Wnt3a CM in a dose-dependent manner compared to C CM (FIG. 6A). To test if Wnt3a had any effect on ALP activity induced by osteoinductive compounds, M2 cells were treated with 1.25 µM SS, 200 ng/ml Shh, or 50 ng/ml BMP-2, alone or in combination with a 1:25 dilution of Wnt3a CM. Wnt3a CM significantly inhibited both SS- and Shh-induced ALP activity (FIG. 6B). However, Wnt3a CM did not significantly inhibit BMP-2-induced ALP activity (FIG. 6B).

Oxysterol-Induced Osteogenesis is Mediated Through the PI3-Kinase/Akt Pathway

Figure 7A:
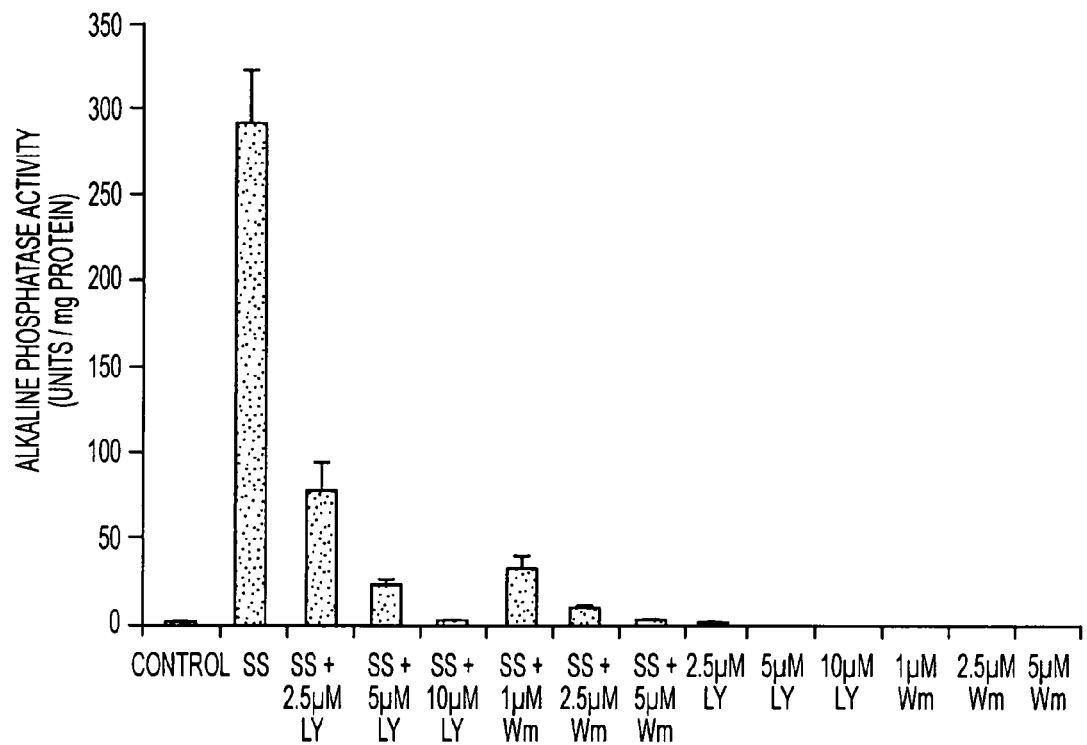
FIG. 7 shows how oxysterol-induced osteogenesis is mediated by the PI3-kinase pathway in marrow stromal cells.
Figure 7B:
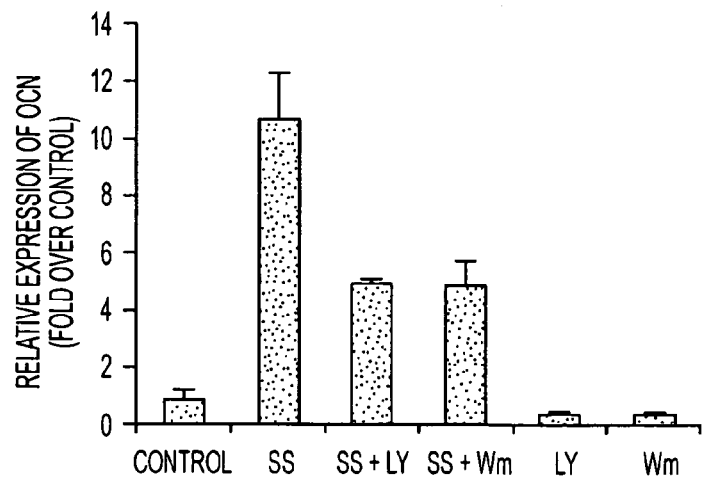
Figure 7C:
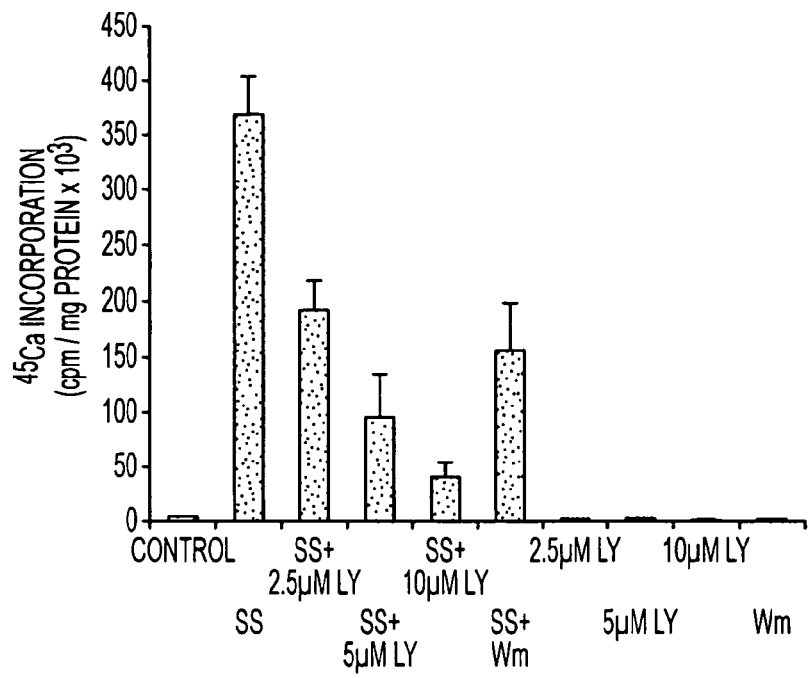
Figure 7D:
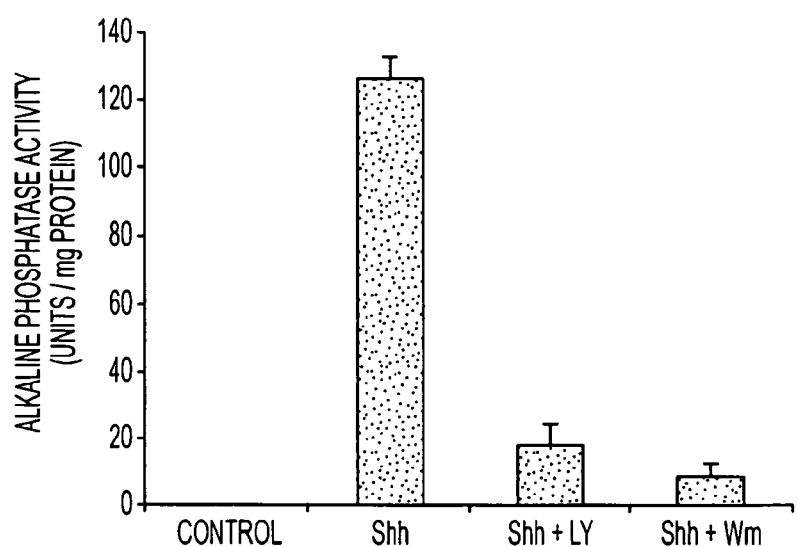
Figure 7E:
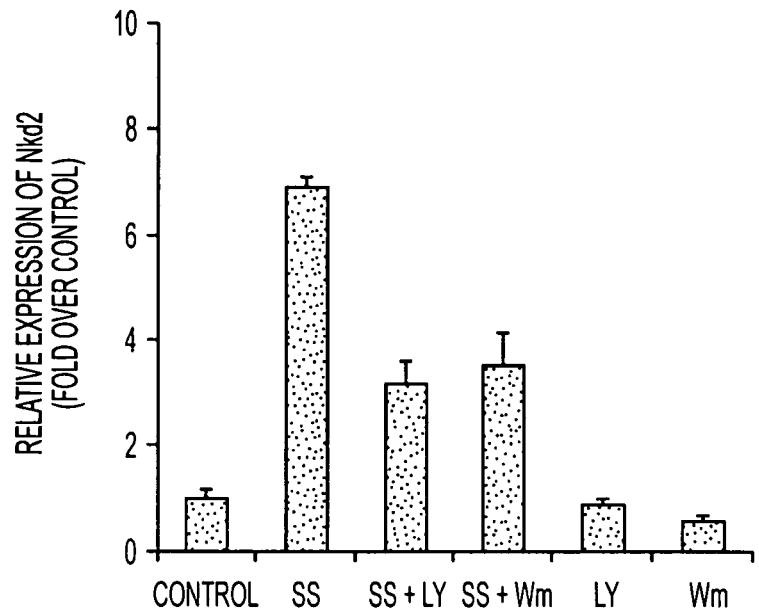
Figure 7F:
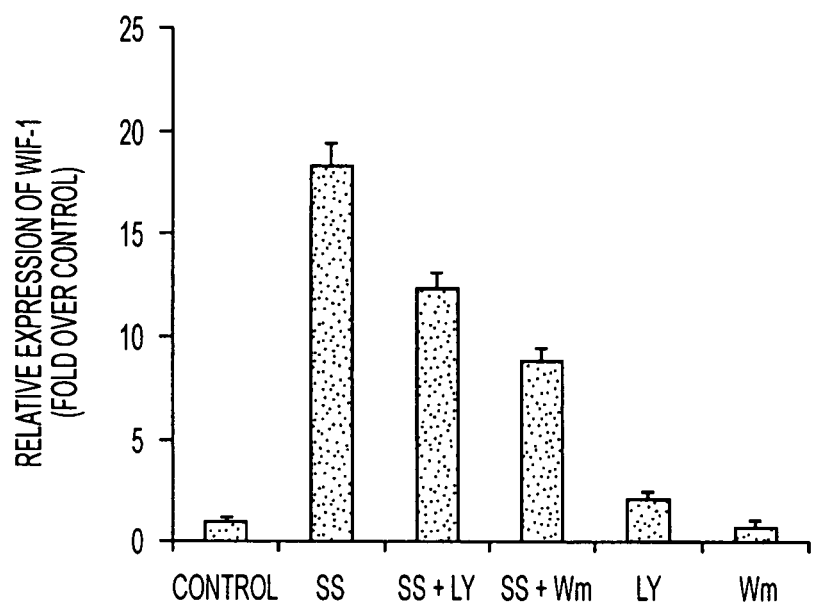

To further elucidate the signaling mechanism(s) by which oxysterols regulate osteoblastic differentiation of M2 cells, we tested the effects of the PI3-kinase pathway inhibitors, LY 294002 (LY) and wortmannin (Wm) on oxysterol-induced markers of osteogenic differentiation. Pre-treatment of M2 cells with either LY or Wm significantly inhibited oxysterol-induced ALP activity in a dose-dependent manner (FIG. 7A). Similarly, Q-RT-PCR analysis showed that pre-treatment with 5 µM of either LY or Wm significantly inhibited SS-induced OCN mRNA expression after 8 days in M2 cells (FIG. 7B). A $^{45}$Ca incorporation assay showed that LY and Wm significantly inhibited oxysterol-induced mineralization after 14 days of treatment (FIG. 7C). Similar to their inhibitory effect on oxysterol-induced ALP activity, LY and Wm also inhibited Shh-induced ALP activity in M2 cells (FIG. 7D). We examined the effects of LY and Wm on Nkd2 and Wif-1 mRNA expression in M2 cells and found that both LY and Wm caused partial yet significant inhibition of oxysterol-induced Nkd2 and Wif-1 mRNA expression (FIGS. 7E and 7F).

We have demonstrated the role of a Wnt-related signaling pathway in oxysterol-induced osteogenic differentiation of MSC. The Wnt signaling pathway plays a role in regulating the proliferation and differentiation of osteoblasts during bone formation. Hedgehog and Wnt signaling appear to cooperate in the development of osteoblasts in vivo (20-22, 30). Our results showed that some, but not all markers of osteogenic differentiation are blocked by Dkk-1. The inhibition by Dkk-1 of oxysterol-induced ALP activity and mineralization but not of OCN expression or Runx2 DNA binding activity is consistent with the observation that oxysterol-induced osteogenic differentiation of MSC is mediated by distinct mechanisms that regulate the different aspects of this process in MSC (14). Dkk-1-inhibitable effects of oxysterols do not appear to be β-catenin dependent, because the cytosolic levels of this protein were not affected upon treatment of MSC with oxysterols, and there was no apparent induction of TCF/Lef transcriptional activity in oxysterol-treated cells. These results are consistent with other reports that demonstrate the antagonistic effect of Dkk-1 on various biological effects independent of β-catenin. Lee et al. reported that Dkk-1 antagonized Wnt signaling in human mesothelioma cells deficient in fβ-catenin (29), and Peng et al. showed that Dkk-1 induced apoptosis in human placental choriocarcinoma cells occurred independent of β-catenin (28). However, because there were relatively high baseline cytosolic and nuclear levels of β-catenin in M2 cells under our experimental conditions, our findings do not rule out the potential cooperative interaction between β-catenin-dependent signaling and oxysterol-induced hedgehog pathway activity. Because β-catenin/TCF/Lef dependent and independent signaling by Wnts are classically referred to as canonical and non-canonical Wnt signaling, respectively, it appears that oxysterol-induced osteogenic effects in MSC best associate with the latter phenomenon. Dkk-1 also partially inhibited Shh- and BMP2-induced ALP activity in M2 cells, but its inhibitory effects were less potent on BMP2-induced ALP activity than that induced by oxysterols or Shh. This difference may be in part due to a higher activation of Wnt signaling by BMP2 and greater reliance of BMP2 on Wnt signaling in inducing osteogenic differentiation (53, 54), requiring greater concentration of Dkk-1 to inhibit this process. In contrast, oxysterols and Shh appear to induce osteogenic differentiation by hedgehog signaling as well as a Wnt signaling-related mechanism(s). We found no evidence of hedgehog signaling being induced by BMP2 in M2 cells as evidenced by the absence of Gli-1 and Ptch expression in response to BMP2. These results are consistent with previous reports that Dkk-1 inhibits the osteogenic effects of both Shh and BMP2 (30, 54), although it is not clear whether such reported inhibitory effects of Dkk-1 are solely due to inhibition of β-catenin dependent mechanisms or also interference with β-catenin independent events.

Figure 8:
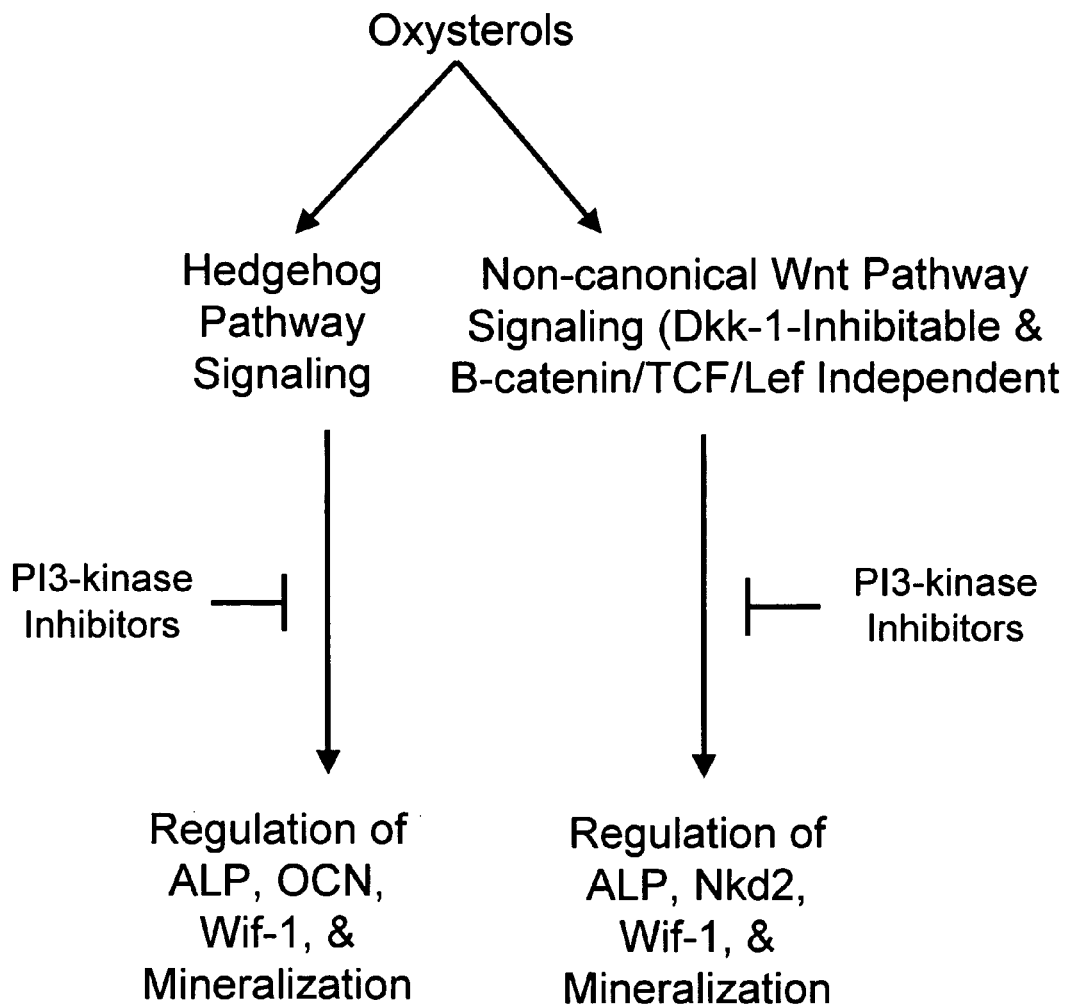
FIG. 8 shows molecular mechanisms by which osteogenic oxysterols induce osteogenic differentiation of marrow stromal cells.

Our present studies demonstrated that Wnt signaling target genes are selectively regulated by oxysterols and Shh and through distinct mechanisms. Axing was neither induced by oxysterols nor by Shh, and Cyclin D1 was only minimally induced at 8 hours but not at 48 hours. In contrast, Nkd2 was only induced by oxysterols, and not by Shh, whereas Wif-1 was induced by both oxysterols and Shh. Differential regulation of Nkd2 expression by oxysterols and Shh is a noteworthy difference between responses induced by these osteogenic molecules. These findings, in addition to the ability of cyclopamine to completely block oxysterol-induced Wif-1, but not Nkd2, and the ability of Dkk-1 to completely inhibit oxysterol-induced Nkd2, and only minimally Wif-1, suggest that the effect of oxysterols on these Wnt target genes is predominantly through either Wnt- or hedgehog-dependent signaling. Given these findings, and the fact that Dkk-I did not affect hedgehog pathway activation by oxysterols, the oxysterol-induced biological responses in MSC may be mediated through activation of two separate pathways: 1) the hedgehog signaling pathway, and 2) the non-canonical Wnt signaling pathway with overlapping as well as distinct effects (FIG. 8). That is, oxysterols activate two distinct signaling pathways: 1) the hedgehog signaling pathway, and 2) a Dkk-1-inhibitable & β-catenin/TCF/Lef independent pathway. Activation of these pathways mediate osteogenic differentiation of MSC and cooperatively or distinctly regulate the markers and genes associated with osteogenic differentiation and Wnt signaling including alkaline phosphatase (ALP) activity, osteocalcin (OCN) mRNA expression, Wif-1 and Nkd2 expression, and matrix mineralization.

PI3-kinase inhibitors LY and Wm were able to partially or completely inhibit all the above biological responses, including those that appear to be mediated through hedgehog signaling, as well as those mediated through Dkk-1-inhibitable signaling. LY and Wm did not inhibit oxysterol-induced hedgehog pathway activation, suggesting that PI3-kinase acts downstream of this pathway. As a measure of PI3-kinase activation by oxysterols, we examined whether oxysterols induced phosphorylation of Akt by Western blotting. Despite the consistent ability of LY and Wm to inhibit oxysterol-mediated responses, increased levels of phospho-Akt normalized to total Akt in oxysterol-treated M2 cells were not substantially induced after 10 min, 30 min, 4 hours, 8 hours, 24 hours, and 48 hours of treatments. There were significant baseline levels of phospho-Akt in M2 cells at all time points examined. However, only in 2 out of more than 8 experiments was a modest 1.5 fold increase in phospho-Akt levels observed, and only after 48 hours of treatment with oxysterols. Rather than PI3-kinase being activated by oxysterols, the basal activity of PI3-kinase may work cooperatively with oxysterols and Shh in inducing osteogenic differentiation of M2 cells. Cooperative and/or synergistic interactions between PI3-kinase and both hedgehog and Wnt signaling have been reported. Riobo et al. reported that PI3-kinase and Akt are essential for Shh signaling during neurogenic and chondrogenic differentiation and Gli activation in progenitor cells, and that their activation by insulin-like growth factor I significantly enhanced Shh-induced signaling (41). In their studies, Shh itself caused only a modest activation of PI3-kinase/Akt, but the baseline level of activity may have also contributed to hedgehog signaling since LY clearly reduced the baseline levels of phospho-Akt in their experimental system. Similarly, PI3-kinase/Akt signaling was shown to mediate morphological and migratory responses of endothelial cells to hedgehog signaling (43), and PI3-kinase and hedgehog signaling were found to converge on Nmyc (a gene that is a target of hedgehog signaling in neuronal cells) to regulate cell cycle progression in neuroprogenitor cells (42). Furthermore, it was reported that PI3-kinase/Akt pathway mediated Wnt3a-induced proliferation of NIH3T3 cells (55), and prevention of apoptosis by Wnt proteins was in part mediated through PI3-kinase/Aki signaling, irrespective of their ability to stimulate canonical Wnt signaling (35). Wnt5a and its receptor Ror2 in *Xenopus* were reported to mediate gene expression in part through PI3-kinase and independently of β-catenin/TCF/Lef (55). The role of PI3-kinase in Runx2-mediated osteogenic and chondrogenic differentiation was demonstrated in progenitor cells where inhibition by LY or a dominant-negative-Akt inhibited Runx2-dependent transcription and expression of osteogenic and chondrogenic differentiation markers (36). Our findings support the concept of cooperative interactions between hedgehog, Wnt, and PI3-kinase signaling, for example, with respect to oxysterol-induced osteogenic differentiation of MSC (FIG. 8).

We found that Wnt3a CM, a classic member of the Wnt family of proteins associated with the canonical Wnt signaling (57), inhibited spontaneous as well as oxsyterol- and Shh-induced ALP activity in MSC. This is consistent with reports by Boland et al. that Wnt3a suppressed osteogenic differentiation while promoting proliferation of human mesenchymal stem cells (57). It has been suggested that canonical Wnt signaling regulates the maintenance and proliferation of progenitor cells, which may need to be suppressed in order for these cells to undergo terminal osteogenic differentiation that may be induced by a mechanism in part dependent on non-canonical Wnt signaling (22). In support of this hypothesis, overexpression of Wnt5a as well as upregulation of Wnt11, both members of the non-canonical Wnt family, promote and enhance the osteogenic differentiation process in osteoprogenitor cells (57). In preliminary studies we found a two-fold increase in mRNA expression of Wnt5a, but not Wnt3a or Wnt10b, in oxysterol-treated M2 cells after 48 hours of treatment. Both Nkd2 and Wif-1 are antagonists of Wnt signaling, and their induction by osteogenic oxysterols supports their role in promoting the terminal osteogenic differentiation of progenitor cells through inhibition of canonical Wnt signaling and proliferative activity (57). However, the role of Wnt signaling in regulation of MSC is likely to be more complex, because other investigators have reported that canonical Wnt/β-catenin signaling may in fact play a pro-differentiation role when applied to a variety of osteoprogenitor cells in vitro (58-61). Such variations in the reported observations may be due to differences in experimental models used by different investigators, as well as differences in commitment stage of various progenitor cells to the osteogenic lineage. Despite these differences, in vitro and in vivo data clearly demonstrate the positive role of Wnt signaling in the development and maintenance of osteoblasts and bone, either through positive regulation of proliferation and maintenance of an osteoprogenitor pool, and/or through pro-osteogenic differentiation effects on these cells. Rodda and McMahon demonstrated distinct roles for hedgehog and Wnt signaling in specification, differentiation, and maintenance of osteoblast progenitors (62). That specific oxysterols mediate their biological effects in part through regulation of Wnt signaling, in addition to hedgehog signaling, supports their role in osteoblast biology.

EXAMPLES

Materials

M2-10B4 cells were purchased from American Type Culture Collection (Rockville, Md.). Oxysterols, β-glycerophosphate (βGP), and ascorbate were obtained from Sigma-Aldrich, Co. (St. Louis, Mo.). RPMI 1640 was obtained from Irvine Scientific (Santa Ana, Calif.), fetal bovine serum (1413S) was obtained from Hyclone (Logan, Utah), recombinant mouse Shh N-terminal peptide, recombinant human BMP2, and recombinant mouse Dickkopf related protein 1 (Dkk-1) were obtained from R&D Systems, Inc. (Minneapolis, Minn.), and cyclopamine, LY 294002, and wortmannin were obtained from EMD Biosciences, Inc. (La Jolla, Calif.). Wnt3a conditioned medium (Wnt3a CM) and empty vector conditioned medium (C CM) were generous gifts from Dr. Peter Tontonoz (UCLA, Los Angeles, Calif.).

Cell Cultures

M2-10B4 cells were maintained in RPMI 1640 with 10% heat-inactivated FBS, supplemented with 1 mM sodium pyruvate, 100 U/ml penicillin and 100 U/ml streptomycin as previously described (13). Treatments were performed in osteogenic differentiation medium containing 5% FBS, 50 μg/ml ascorbate, and 3 mM βGP.

Example 1

General Alkaline Phosphatase (ALP) Activity Assay

Colorimetric alkaline phosphatase (ALP) activity assay on whole cell extracts was performed as previously described (13).

Example 2

General $^{45}$Ca Incorporation Assay $^{45}$Ca incorporation assay as a measure of matrix mineralization in cell monolayers was performed as previously described (45).

Example 3

General Quantitative RT-PCR (Q-RT-PCR) Procedure

Total RNA was extracted with the RNA isolation kit from Stratagene (La Jolla, Calif.) according to the manufacturer's instructions. RNA was DNase-treated using the DNA-free kit from Ambion, Inc. (Austin, Tex.). 3 μg of RNA was reverse-transcribed using reverse transcriptase from Stratagene (La Jolla, Calif.) to make single stranded cDNA. The cDNAs were mixed with Qi SYBR Green Supermix from Bio-Rad Laboratories (Hercules, Calif.) for quantitative RT-PCR using a Bio-Rad I-cycler IQ quantitative thermocycler. All PCR samples were prepared in triplicate or quadruplicate. Each sample was added to duplicate wells of a 96-well plate. After 40 cycles of PCR, melt curves were analyzed in order to ensure primer specificity, and the identity of all PCR products were verified by sequencing and comparing with the complete mRNA sequence obtained from PubMed's GenBank. Fold changes in gene expression were calculated using the ΔΔCt method (14). All primers were designed using the Beacon Designer software from Bio-Rad Laboratories (Hercules, Calif.). Primers used are as follows: OCN (5'-TCTCTCTGACCTCACAGATGCC-3' (SEQ ID NO: 1) and 5'-TACCTTATTGCCCTCCTGCTTG-3' (SEQ ID NO: 2)), Axin2(5'GAGGCAGAAGCCACACA-GAGA-3' (SEQ ID NO: 3) and 5'-CTGGCCGACAGTG-CAAGAC-3' (SEQ ID NO: 4)), Cyclin D1(5'-GACACCAATCTCCTCAACGAC-3' (SEQ ID NO: 5) and 5'-TCACAGACCTCCAGCATCC-3' (SEQ ID NO: 6)), NKD2 (5'-GAAGACAACCGCCAAGAATG-3' (SEQ ID NO: 7) and 5'GGAGGAGTGATTGACAGAGG-3' (SEQ ID NO: 8)), WIF-1 (5'-CAAGTGTAAGTGCCCGAAAGG-3' (SEQ ID NO: 9) and 5'-CTGGCTCCATACCTCTTATTGC-3' (SEQ ID NO: 10)), and GAPDH (5'-ATTGTCAGCAAT-GCATCCTG-3' (SEQ ID NO: 11) and 5'-ATGGACTGTG-GTCATGAGCC-3' (SEQ ID NO: 12)).

Example 4

General Transient Transfection and Reporter Assay

M2-10B4 cells at 70% confluence were transfected for 24 hours using FuGENE 6 Transfection Reagent (Roche Applied Science, Indianapolis, Ind.) according to manufacturer's instructions. The wild-type and mutant TCF/LEF binding site driven luciferase constructs (TBE4-luc and TBE4-luc-mut, repectively) were generous gifts from Dr. Baruch Frenkel (University of Southern California, Los Angeles, Calif.), and the Cyclin D1 promoter element-driven luciferase construct (Cyclin D1-luc) was a generous gift from Dr. Fanxin Long (Washington University, St. Louis, Mo.). Firefly luciferase values were normalized to Renilla luciferase activity and pEGFP-NI was used to evaluate transfection efficiency. Cells were then treated for 24, 48, or 72 hours with test agents before measuring luciferase activity using the Dual-Luciferase Reporter 1000 Assay System (Promega, Madison, Wis.) according to the manufacturer's instructions.

Example 5

General Cytosolic Protein Extraction and Total Cell Lysate Preparation

M2-10B4 cells were dounce homogenized 25 times in HLB/P Buffer [10 mM HEPES/KOH, pH 7.9, 10 mM KCl, 1.5 mM $MgCl_2$, 0.5 mM DTT, 1:100 protease inhibitor cocktail (EMD Biosciences, Inc., La Jolla, Calif.), 1:100 phosphatase inhibitor cocktail I and II (Sigma, St. Louis, Mo.)], then spun down at 2,500 rpm for 5 minutes at 4° C. The supernatant was collected and spun down at 19,000 rpm for 30 minutes at 4° C. The supernatant after this spin was collected and saved as the cytosolic protein extract. For preparation of total cell lysates, M2-10B4 cells were incubated on ice for 15 minutes in lysis buffer (50 mM NaCl, 5 mM EDTA, pH 8.0, 5 mM EGTA, 10 mM HEPES/KOH, pH 7.9, 0.1% Triton X-100, and 1:100 protease inhibitor cocktail (EMD Biosciences, Inc., La Jolla, Calif.). For phosphorylated proteins 0.1 mM sodium vanadate ($Na_3VO_4$) was also included in the lysis buffer. Each sample was then sonicated and spun down at 12,000 rpm for 5 minutes at 4° C. The supernatant after this spin was collected and saved as the total cell lysate.

Example 6

General Western Blot Analysis

Protein concentrations were determined using the Bio-Rad protein assay (Hercules, Calif.), and SDS-PAGE was performed as previously described (46). Briefly, cytosolic extracts or total cell lysates (30 μg) were separated on a 10% Tris-HCl gel from Bio-Rad laboratories (Hercules, Calif.) and transferred overnight onto a nitrocellulose membrane from Amersham Biosciences (Piscataway, N.J.). Blocking was performed with 5% dry skim milk (Becton, Dickinson and Company, Sparks, Md.) in Tris-buffer saline containing 0.1% Tween-20 (TBS-T) for 2 hours at room temperature. Blots were then incubated with the monoclonal antibody against, phospho(Ser473)-Akt, or the polyclonal antibodies against Akt, β-catenin or β-actin (Cell Signaling Technology, Danvers, Mass.), following the instructions of the manufacturer. Binding of the primary antibody was detected by a secondary antibody labeled with horseradish peroxidase (Santa Cruz Biotechnology, Inc., Santa Ruz, Calif.). The blots were developed using enhanced chemiluminescence detection reagents (Perkin Elmer, Boston, Mass.).

Statistical Analysis

Computer-assisted statistical analyses were performed using the StatView 4.5 program. All p values were calculated using ANOVA and Fisher's projected least significant difference (PLSD) significant test. A value of $p<0.05$ was considered significant.

Example 7

The LRP5/6 Inhibitor, Dickkopf-1 (Dkk-1), Inhibits Oxysterol-Induced Osteogenic Differentiation in Marrow Stromal Cells Alkaline phosphatase (ALP) activity assay (see Example above) was performed in M2 cells pre-treated with 1 or 2 μg/ml Dkk-1 or vehicle for 2 h followed by treatment for 3 days with control vehicle or 2.5 μM of the oxysterol combination, SS (A); 200 ng/ml Shh (B); or 50 ng/ml BMP-2 (C) (See FIGS. 2A-2C). Results from a representative experiment are reported as the mean of quadruplicate determinations±S.D. and normalized to protein concentrations ($p<0.01$ for Control versus SS, Shh and BMP-2 and SS and Shh versus SS and Shh plus Dkk-1 at both concentrations; $p<0.02$ for BMP-2 versus BMP-2 plus 2 μg/mL Dkk-1).

$^{45}$Ca incorporation assay (see Example above) was used to measure mineralization in M2 cells pre-treated with 1 μg/ml Dkk-1 or vehicle for 2 h, and then treated with control vehicle or 2.5 μM SS 12 days (See FIG. 2D). Data from a representative experiment are reported as the mean of quadruplicate determinations±S.D, and normalized to protein concentrations ($p<0.01$ for Control versus SS and SS versus SS plus Dkk-1).

M2 cells were pre-treated with vehicle or 1 μg/ml Dkk-1 for 2 h followed by treatment with control vehicle or 5 μM SS for 6 days. RNA was isolated and analyzed by Q-RT-PCR for OCN expression (See FIG. 2E). Data from a representative experiment are reported as the mean of triplicate determination±S.D. and normalized to GAPDH expression (p<0.003 for Control versus SS with or without Dkk-1; p<0.001 for Control versus Dkk-1).

Example 8

Effect of Osteogenic Oxysterols on TCF/Lef Transcriptional Activity in Marrow Stromal Cells M2 cells were transfected with a luciferase reporter driven by 4 wild-type or mutant TCF/Lef DNA binding sites (TBE4-luc and TBE4-luc-mut, respectively) and analyzed for their response to 5 µM SS, 200 ng/ml Shh, 40 mM LiCl, or control vehicle after 24 h of treatment (see FIG. 3A). Data from a representative experiment are reported as the mean of triplicate samples±S.D. and normalized to Renilla luciferase activity (p<0.001 for Control versus LiCl with TBE4-luc expression vector).

M2 cells were transfected with a luciferase reporter driven by a Cyclin D1 promoter element (Cyclin D1-luc) and analyzed for their response to 5 µM SS, 40 mM LiCl, or control vehicle after 24 h of treatment (see FIG. 3B). Data from a representative experiment are reported as the mean of triplicate samples±S.D. and normalized to Renilla luciferase activity (p<0.01 for Control versus LiCl).

Example 9

Osteogenic Oxysterols Differentially Regulate Wnt Target Gene Expression in Marrow Stromal Cells M2 cells were treated with 5 µM SS, 200 ng/ml Shh, 40 mM LiCl, or control vehicle for 8 or 48 h. RNA was isolated and analyzed by Q-RT-PCR for Axing expression (See FIGS. 4A and 4B). Data from a representative experiment are reported as the mean of triplicate determination±S.D. and normalized to GAPDH expression (p<0.02 for Control versus LiCl at 8 h and 48 h, and for Control versus SS at 48 h).

M2 cells were treated with 5 µM SS, 200 ng/ml Shh, or control vehicle for 8 or 48 h. RNA was isolated and analyzed by Q-RT-PCR for Cyclin D1 expression (See FIGS. 4C and 4D). Data from a representative experiment are reported as the mean of triplicate determination±S.D. and normalized to GAPDH expression (p<0.05 for Control versus Shh at 8 h).

M2 cells were treated with 5 µM SS, 200 ng/ml Shh, or control vehicle for 48 h. RNA was isolated and analyzed by Q-RT-PCR for Nkd2 (E) and WIF-1 (F) expression (See FIGS. 4E and 4F). Data from a representative experiment are reported as the mean of triplicate determination±S.D. and normalized to GAPDH expression (p<0.01 for Control versus SS for both Nkd2 and WIF-1 expression; p<0.001 for Control versus Shh for WIF-1 expression).

Example 10

Osteogenic Oxysterols Differentially Regulate Wnt Target Gene Expression in Marrow Stromal Cells M2 cells were pre-treated for 2 h with vehicle or cyclopamine (Cyc) at the concentrations indicated. Next, cells were treated with 5 µM SS or control vehicle for 48 h. RNA was isolated and analyzed for Nkd2 (A) and WIF-1 (B) expression by Q-RT-PCR (See FIGS. 5A and 5B). Data from a representative experiment are reported as the mean of triplicate determination±S.D. and normalized to GAPDH expression (p<0.001 for Control versus SS for both, Nkd2 and Wif-1 expression, and for SS versus SS+Cyc at both, 2 and 4 µM, for Wif-1 expression).

M2 cells were pre-treated for 2 h with Dkk-1 or vehicle. Next, cells were treated with 5 µM SS or control vehicle for 48 h. RNA was isolated and analyzed for Nkd2 (C), Wif-1 (D), and Ptch (E) expression (See FIGS. 5C-5E). Data from a representative experiment are reported as the mean of triplicate determination±S.D. and normalized to GAPDH expression (p<0.01 for Control versus SS for Nkd2, Wif-1, and Ptch expression; p<0.001 for SS versus SS plus Dkk-1 for Nkd2 expression; p<0.03 for SS versus SS plus Dkk-1 for Wif-1 expression).

Example 11

Wnt3a Conditioned Medium Inhibits Oxysterol-Induced Alkaline Phosphatase Activity in Marrow Stromal Cells A cell-associated alkaline phosphatase activity (ALP) assay is used as a screen to identify potential osteoinductive oxysterols. The protocol is a modification of alkaline phosphatase assay kit from Sigma. Cells are cultured in 24-well tissue culture plates. After treatments with test agents, cells are rinsed twice with PBS and scraped into 200 ml of lysis buffer (0.2% NP-40 in 1 mM $MgCl_2$) and sonicated for 10 seconds. Next, 1 ml of reaction mixture is added to each well. Reaction mixture is 221 alkaline buffer (Sigma): stock substrate solution (1:1). Stock substrate solution is prepared by dissolving 40 mg of Sigma 104 phosphatase substrate in 10 ml of dd$H_2O$. After addition of reaction mixture to lysed cells, incubation is performed for 30 minutes at 37 C. The yellow color is indicative of alkaline phosphatase activity. The reaction is stopped by the addition of 12 ml of 1N NaOH to each well, and absorbance is determined at 405 nm. Alkaline phosphatase activity is calculated using p-nitrophenol as a standard, according to Sigma kit's instructions. Results are normalized to total protein in each well determined using the Bio-Rad protein assay solution (Bio-Rad Laboratories).

An ALP activity assay was performed in M2 cells treated for 6 days in osteogenic medium with various dilutions of Wnt3a conditioned medium (Wnt3a CM) or control conditioned medium (C CM) (See FIG. 6A). Results from a representative experiment are reported as the mean of triplicate determinations±S.D. and normalized to protein concentrations (p<0.05 for all C CM versus Wnt3a CM (1:25) and (1:50)).

An ALP activity assay in M2 cells treated for 3 days with 1.25 µM SS, 200 ng/ml Shh, 50 ng/ml BMP-2, or control vehicle, in combination with either C CM or Wnt3a CM at a 1:25 dilution was performed (See FIG. 6B). Results from a representative experiment are reported as the mean of quadruplicate determinations±S.D. and normalized to protein concentrations (p<0.02 for Control versus SS, Shh and BMP-2, and for SS and Shh versus SS and Shh plus Wnt3a CM).

Example 12

Oxysterol-Induced Osteogenesis is Mediated by the PI3-Kinase Pathway in Marrow Stromal Cells ALP activity assay in M2 cells pre-treated with various doses of the PI3-kinase inhibitors, LY 294002 (LY) or wormannin (Wm) or vehicle for 2 h followed by treatment for 3 days with 2.5 μM SS control vehicle was performed (See FIG. 7A). Results from a representative experiment are reported as the mean of quadruplicate determinations±S.D. and normalized to protein concentrations ($p<0.001$ for Control versus SS, and for SS versus SS plus LY or Wm at all concentrations).

M2 cells were pre-treated with 5 μM LY, 2.5 μM Wm, or vehicle for 2 h followed by treatment with 2.5 μM SS control vehicle for 6 days. RNA was analyzed for OCN expression by Q-RT-PCR and normalized to GAPDH ($p<0.01$ for Control versus SS and for SS versus SS+LY and SS+Wm) (See FIG. 7B).

$^{45}$Ca incorporation assay was used to measure mineralization in M2 cells pre-treated with various doses of LY, 1 μM Wm, or vehicle for 2 h, and then treated with 5 μM SS or control vehicle for 14 days (See FIG. 7C). Data from a representative experiment are reported as the mean of quadruplicate determinations±S.D. and normalized to protein concentrations ($p<0.001$ for Control versus SS, and for SS versus SS+LY and SS+Wm at all concentrations).

M2 cells were pretreated with 5 μM LY, 1 μM Wm, or vehicle for 2 h followed by treatment with 200 ng/ml Shh or control vehicle for 3 days. ALP activity assay was performed and results from a representative experiment are reported as the mean of quadruplicate determinations±S.D. and normalized to protein concentrations ($p<0.001$ for Control versus Shh and for Shh versus Shh+LY and Shh+Wm) (See FIG. 7D).

M2 cells were pre-treated for 2 h with 5 μM LY, 2.5 μM Wm, or vehicle followed by treatment with 5 μM SS or control vehicle for 48 h. RNA was isolated and analyzed for Nkd2 (FIG. 7E) and Wif-1 (FIG. 7F) expression. Data from a representative experiment are reported as the mean of triplicate determination±S.D. and normalized to GAPDH expression ($p<0.01$ for Control versus SS, and for SS versus SS plus LY and Wm for both Nkd2 and WIF-1 expression).

Example 13

Effect of Oxysterols on Alkaline Phosphatase Activity in M2-10B4 Marrow Stromal Cells M2-10B4 marrow stromal cells were treated with oxysterols at various doses for 3 days after which they were collected and analyzed by calorimetric assay for alkaline phosphatase activity (a marker of osteoblastic differentiation) (Table 1); the alkaline phosphatase assay described above was used. Results from a representative experiment are shown as the fold induction in alkaline phosphatase activity compared to control untreated cells

TABLE 1

| Oxysterol | Fold Induction |
|---|---|
| Oxy22 (2.5 μM) | 4 |
| Oxy22 (5 μM) | 9 |
| Oxy26 (2.5 μM) | 27 |
| Oxy26 (5 μM) | 76 |
| Oxy27 (2.5 μM) | 17 |
| Oxy27(5 μM) | 42 |
| Oxy28 (2.5 μM) | 59 |
| Oxy28 (5 μM) | 75 |
| Oxy39 (2.5 μM) | 52 |
| Oxy39 (5 μM) | 148 |
| Oxy40 (2.5 μM) | 28 |
| Oxy40 (5 μM) | 105 |
| Oxy41 (2.5 μM) | 46 |
| Oxy41 (5 μM) | 175 |

TABLE 1-continued

| Oxysterol | Fold Induction |
|---|---|
| Oxy42 (2.5 μM) | 166 |
| Oxy42 (5 μM) | 290 |
| Oxy48 (2.5 μM) | 11 |
| Oxy48 (5 μM) | 43 |
| Oxy49 (2.5 μM) | 170 |
| Oxy49 (5 μM) | 204 |

Example 14

Effect of Oxysterols on Alkaline Phosphatase Activity in M2-10B4 Marrow Stromal Cells M2-10B4 marrow stromal cells were treated with oxysterols at various doses for 3 days after which they were collected and analyzed by colorimetric assay for alkaline phosphatase activity (a marker of osteoblastic differentiation) (Table 2); the alkaline phosphatase assay described above was used. Results from a representative experiment are shown as the fold induction in alkaline phosphatase activity compared to control untreated cells.

TABLE 2

| Oxysterol | Fold Induction |
|---|---|
| Oxy20 (2.5 μM) | 36 |
| Oxy20 (5 μM) | 68 |
| Oxy27 (2.5 μM) | 17 |
| Oxy27(5 μM) | 42 |
| Oxy34 (2.5 μM) | 213 |
| Oxy34 (5 μM) | 250 |
| Oxy36 (2.5 μM) | 101 |
| Oxy36 (5 μM) | 191 |
| Oxy38 (2.5 μM) | 132 |
| Oxy38 (5 μM) | 246 |

Example 15

Effect of Various Oxysterol Molecules on Alkaline Phosphatase Activity in Marrow Stromal Cells. [Oxy50-Oxy54]

Figure 9:
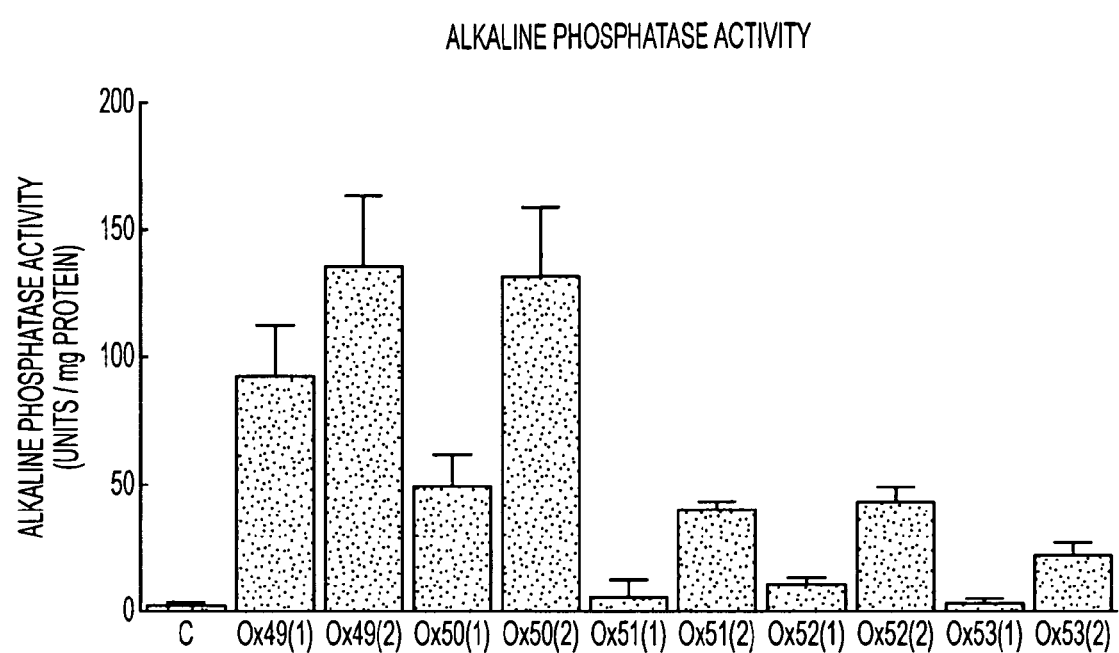
FIG. 9 shows the effect of various oxysterol molecules on alkaline phosphatase activity in marrow stromal cells.

M2-10B4 bone marrow stromal cells were treated in culture with control vehicle (C) or various oxysterol (Oxy) molecules as indicated at either 1.25 (1) or 2.5 (2) μM concentrations. After 3 days of treatment, alkaline phosphatase activity as a measure of early osteogenic differentiation of cells was measured in whole cell lysates (See FIG. 9 and Table 3); the alkaline phosphatase assay described above was used. Results are reported as the mean of quadruplicate determinations±SD ($p<0.001$ for C vs. all Oxy conditions except for Oxy51(1) and Oxy53(1) where $p>0.05$ and therefore not significant, and $p<0.05$ for C vs. Oxy52(1). Table 3 reports results as fold induction over control untreated cells.

TABLE 3

| Oxysterol | Fold Induction |
|---|---|
| Oxy49 (1.25 μM) | 46 |
| Oxy49 (2.5 μM) | 68 |
| Oxy50 (1.25 μM) | 25 |
| Oxy50 (2.5 μM) | 65 |
| Oxy51 (1.25 μM) | 3 |

TABLE 3-continued

| Oxysterol | Fold Induction |
| --- | --- |
| Oxy51 (2.5 µM) | 20 |
| Oxy52 (1.25 µM) | 5 |
| Oxy52 (2.5 µM) | 22 |
| Oxy53 (1.25 µM) | 2 |
| Oxy53 (2.5 µM) | 11 |

Example 16

Figure 11:
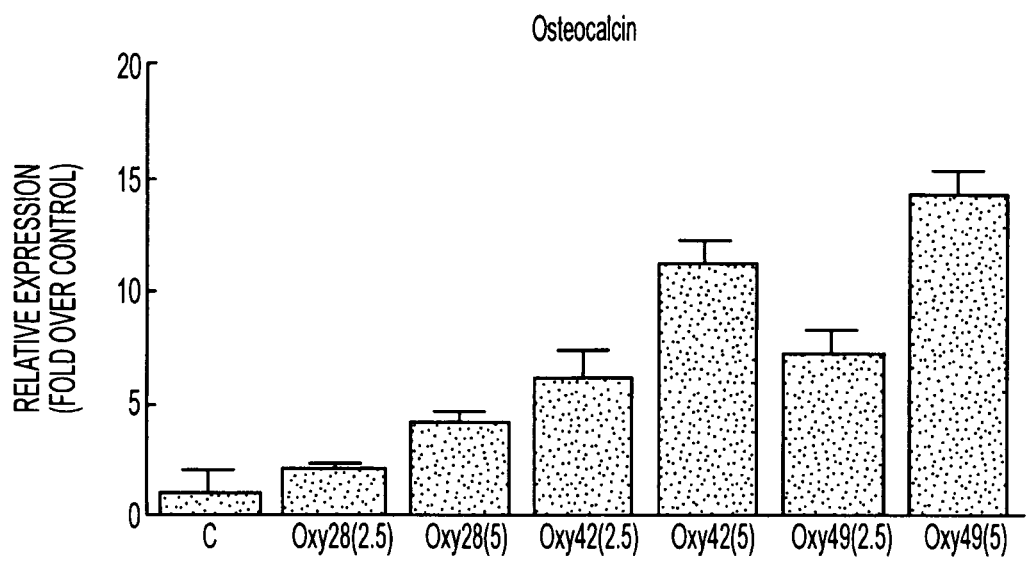
FIG. 11 shows the effect of various oxysterols on osteocalcin mRNA expression in bone marrow stromal cells.

Effect of Various Oxysterols on Osteocalcin mRNA Expression in Bone Marrow Stromal Cells M2-10B4 cells were treated with control vehicle (C) or various doses (µM) of oxysterols as indicated. After 6 days of treatments, mRNA was extracted from cells and analyzed by Q-RT-PCR for osteocalcin and GAPDH expression (See FIG. 11). Data from a representative experiment are reported as the mean of triplicate determinations±SD normalized to GAPDH.

Example 17

Effect of Various Oxysterols on Adipogenesis of Bone Marrow Stromal Cells

Figure 12:
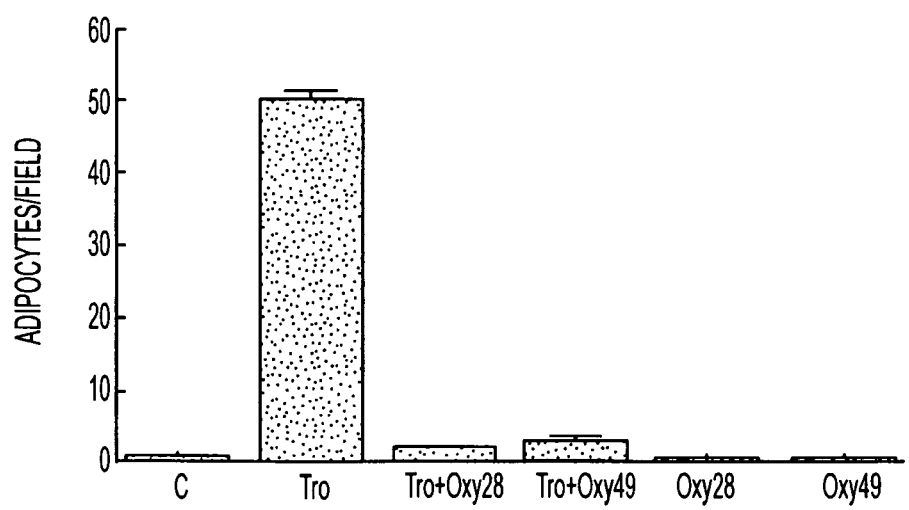
FIG. 12 shows the effect of various oxysterols on adipogenesis of bone marrow stromal cells.

M2-10B4 cells were treated with control vehicle (C) or the inducer of adipogenesis, Troglitazone (Tro, 10 µM), alone or in combination with various oxysterols (5 µM). After 10 days of treatments, cells were stained with Oil red O to detect adipocytes. Adipocytes were counted in triplicate wells per condition, 5 fields per well (See FIG. 12). Data from a representative experiment are reported as the mean of triplicate determinations±SD.

Figure 13:
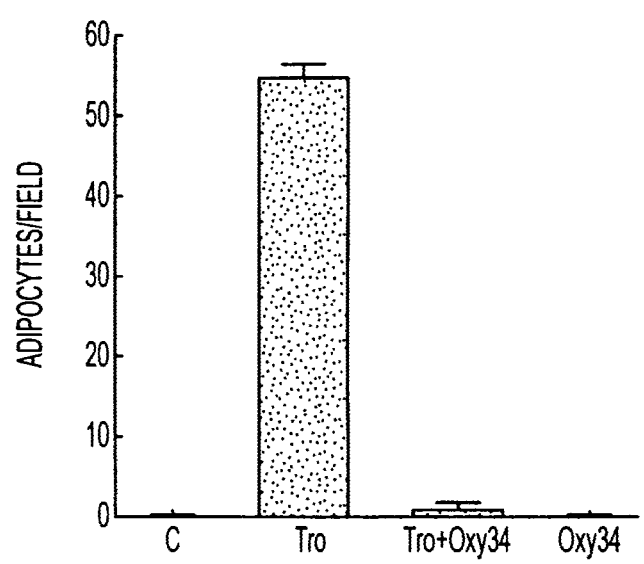
FIG. 13 shows the effect of various oxysterols on adipogenesis of bone marrow stromal cells.

For example, M2-10B4 cells were treated with control vehicle (C) or the inducer of adipogenesis, Troglitazone (Tro, 10 µM), alone or in combination with Oxy34 (5 µM). After 10 days of treatments, cells were stained with Oil red O to detect adipocytes. Adipocytes were counted in triplicate wells per condition, 5 fields per well. Data from a representative experiment are reported as the mean of triplicate determinations±SD (See FIG. 13).

Example 18

Effect of Oxy49 and Shh on Gli Induced Reporter Activity

Figure 14:
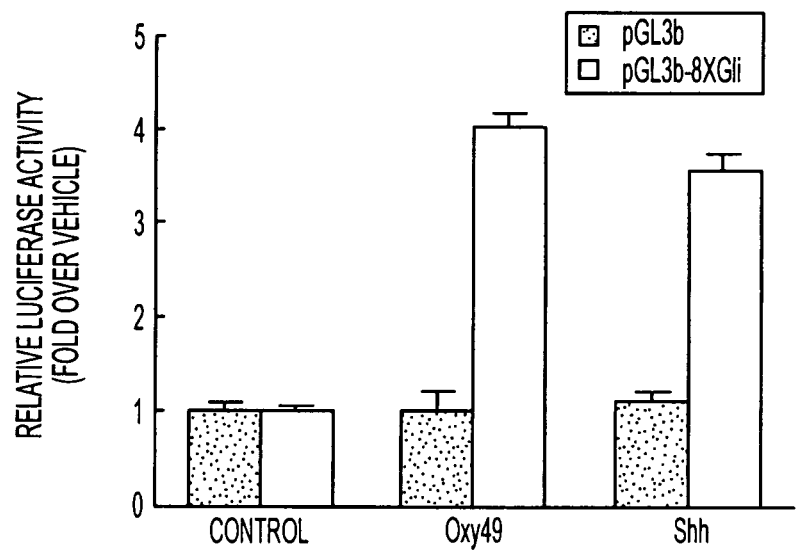
FIG. 14 shows the effect of Oxy49 and Shh on Gli induced reporter activity.

M2-10B4 bone marrow stromal cells were transfected with an 8XGli luciferase reporter or the empty vector (pGL3b). Cells were subsequently treated with control vehicle, 5 µM Oxy49, or 400 ng/ml recombinant human sonic hedgehog (Shh) as positive control. After 48 hours of treatments, reporter luciferase activity was measured and normalized to Renilla luciferase activity (See FIG. 14). Data from a representative experiment are reported as the mean of quadruplicate determinations±SD.

Example 19

Effect of Oxy34 and Shh on Gli Induced Reporter Activity

Figure 15:
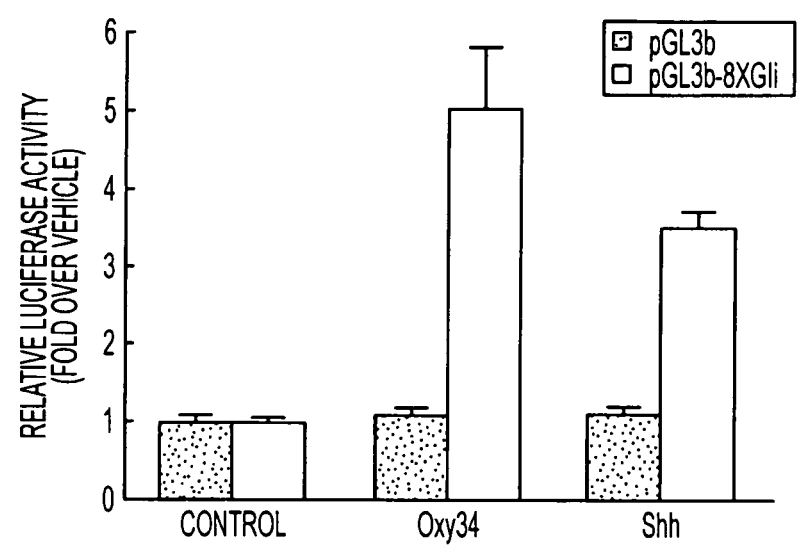
FIG. 15 shows the effect of Oxy34 and Shh on Gli induced reporter activity.

M2-10B4 bone marrow stromal cells were transfected with an 8XGli luciferase reporter or the empty vector (pGL3b). Cells were subsequently treated with control vehicle, 5 µM Oxy34, or 400 ng/ml recombinant human sonic hedgehog (Shh) as positive control. After 48 hours of treatments, reporter luciferase activity was measured and normalized to Renilla luciferase activity (See FIG. 15). Data from a representative experiment are reported as the mean of quadruplicate determinations±SD.

Example 20

Figure 16A:
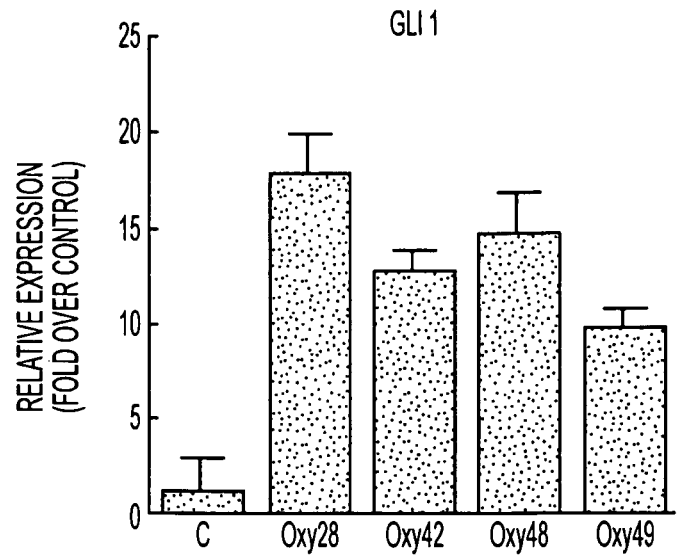
FIG. 16 shows the effect of various oxysterols on Gli 1 and Patched mRNA expression in bone marrow stromal cells.
Figure 16B:
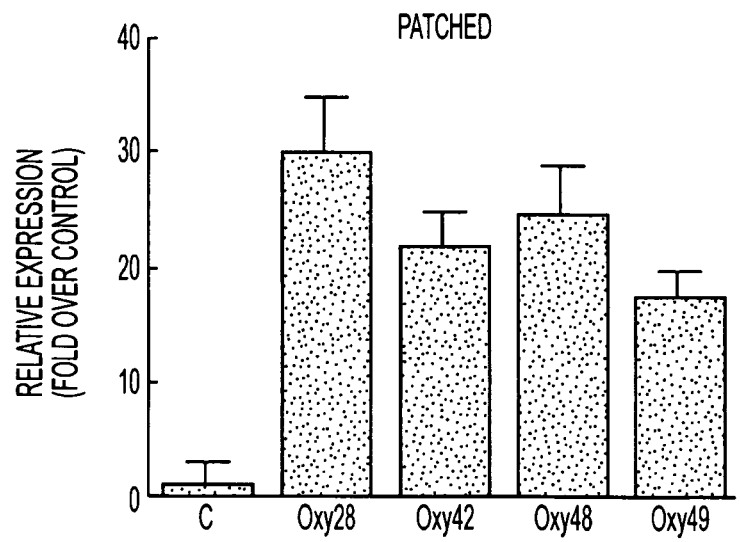

Effect of Various Oxysterols on Gli 1 and Patched mRNA Expression in Bone Marrow Stromal Cells M2-10B4 cells were treated with control vehicle (C) or various oxysterols (5 µM) as indicated. After 48 hours of treatments, mRNA was extracted from cells and analyzed by Q-RT-PCR for expression of hedgehog target genes Gli 1 and Patched (See FIGS. 16A and 16B). Data from a representative experiment are reported as the mean of triplicate determinations±SD normalized to GAPDH.

Example 21

Figure 17:
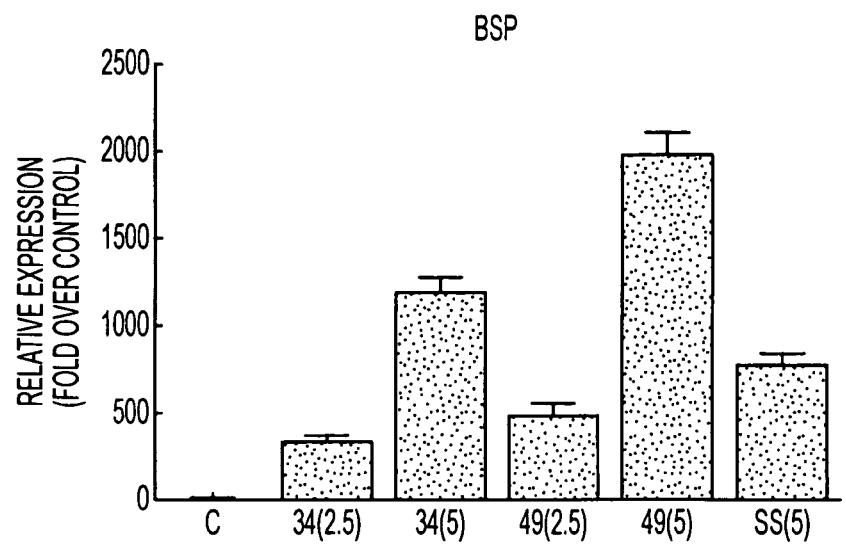
FIG. 17 shows the effect of various oxysterols on bone sialoprotein mRNA expression in bone marrow stromal cells.

Effect of Various Oxysterols on Bone Sialoprotein mRNA Expression in Bone Marrow Stromal Cells M2-10B4 cells were treated with control vehicle (C) or various doses (µM) of oxysterols (Oxy34 or Oxy49) as indicated. SS, refers to 5 µM each of 20S-hydroxycholesterol+22S-hydroxycholesterol used as a positive control. After 6 days of treatments, mRNA was extracted from cells and analyzed by Q-RT-PCR for BSP and GAPDH expression (See FIG. 17). Data from a representative experiment are reported as the mean of triplicate determinations±SD normalized to GAPDH.

Example 22

Effect of Various Oxysterol Molecules on Bone Sialoprotein (BSP) Expression in Marrow Stromal Cells. [Oxy50-Oxy54]

Figure 10:
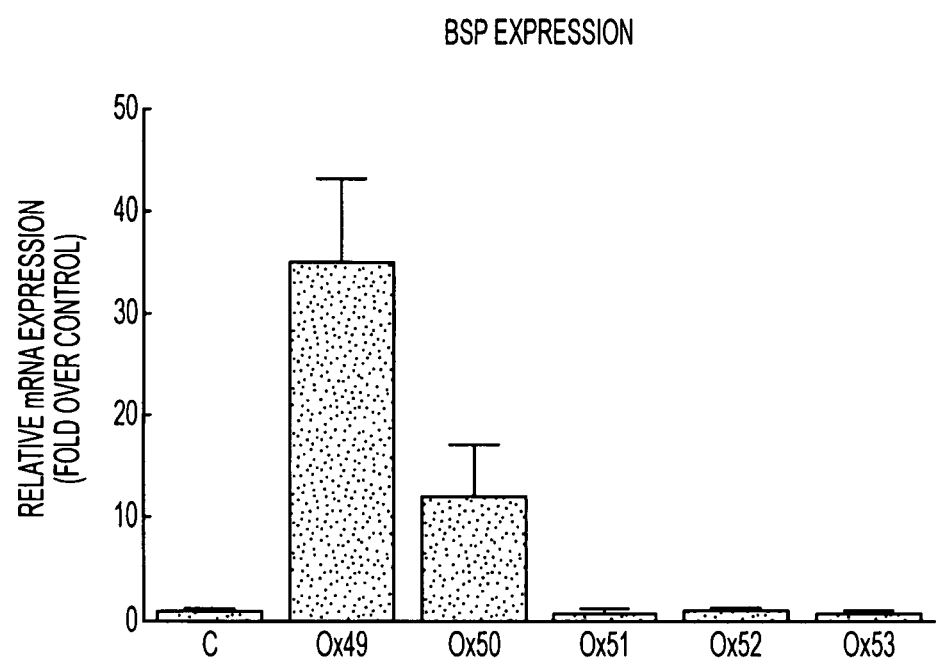
FIG. 10 shows the effect of various oxysterol molecules on bone sialoprotein (BSP) expression in marrow stromal cells.

M2-10B4 bone marrow stromal cells were treated in culture with control vehicle (C) or various oxysterol (Oxy) molecules as indicated at 2.5 µM concentration. After 48 hours of treatment, RNA was isolated and analyzed for BSP expression by Q-RT-PCR as a measure of osteogenic differentiation (See FIG. 10). Results are reported as the mean of triplicate determinations±SD ($p<0.001$ for C vs. Oxy49 and Oxy50)

Example 23

Effect of Various Oxysterols on Mineralization of Marrow Stromal Cells

Figure 18:
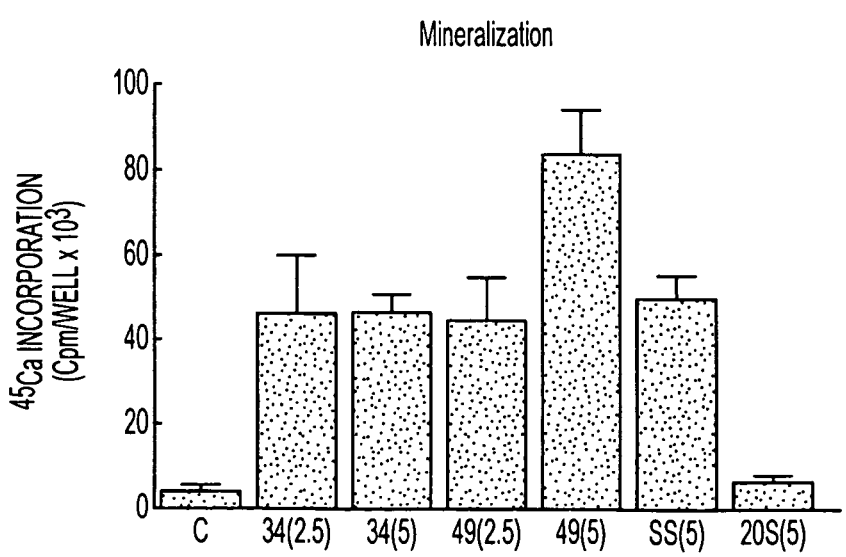
FIG. 18 shows the effect of various oxysterols on mineralization of marrow stromal cells.

M2-10B4 cells were treated for 14 days with control vehicle (C) or various concentrations (µM) of oxysterols as indicated. SS refers to 20S-hydroxycholesterol+22S-hydroxycholesterol in combination. After 12 days with refeeding every $5^{th}$ day, $^{45}$Ca was added and on day 14, $^{45}$Ca incorporation was measured (See FIG. 18). Data from a representative experiment are reported as the mean of quadruplicate determinations±SD. The data indicate that administration of oxysterol compound Oxy34 or Oxy49 or the oxysterol combination SS increased mineralization. The oxysterols Oxy34 and Oxy49 induce BSP expression; Oxy34 and Oxy49 have a hydroxyl group substituted onto the 6-carbon of the B-ring. A hydroxyl group substituent on the number 6 carbon of the B-ring was observed to result in increased osteoinductive potential of the Oxy molecules. The oxysterol 20S does not have a hydroxyl group substituted onto the 6-carbon of the B-ring.

Hedgehog Signaling:

All of the oxysterols presented in FIG. 1 activated the hedgehog signaling pathway as assessed by at least one of the following methodologies:

1. Luciferase reporter activity using a reporter construct with 8X-Gli binding sites
2. Q-RT-PCR analysis of the induction of hedgehog pathway target gene expression Gli 1 and Patched
3. Inhibition of the osteoinductive effects of the oxysterols by hedgehog pathway inhibitor, cyclopamine Expression of Bone Sialoprotein (BSP):

We considered the ability of oxysterols to induce the expression of BSP in M2-10B4 marrow stromal cells. Oxysterols that induce BSP expression, such as Oxy34 and Oxy49, can be potent inducers of osteoblastic differentiation and mineralization in M2-10B4 cell cultures. Oxysterols that induce other markers of osteoblastic differentiation including 1) alkaline phosphatase activity and 2) osteocalcin mRNA expression, but not BSP expression, induce mineralization at higher doses than those oxysterols which also induce BSP expression, for example Oxy34 and Oxy49. Oxysterols that induce 1) alkaline phosphatase activity, 2) osteocalcin mRNA expression, and 3) BSP expression can be optimal in inducing bone growth. Such osteogenesis or bone mineral formation can be assessed by $^{45}$Ca incorporation assay in cultures of M2-10B4 cells.

Based on our structure-activity relationship studies discussed herein, it appears that the OH groups on C3 and C20 of an oxysterol are important for the induction of osteogenesis as measured by the induction of various markers of osteogenic differentiation including alkaline phosphatase activity and osteocalcin mRNA expression. The induction of bone sialoprotein (BSP) mRNA expression may be a prerequisite for the maximal potency of oxysterols, such as the Oxy molecules considered herein, to induce mineralization in cultures of M2-10B4 marrow stromal cells when used at nanomolar to low micromolar concentrations. Therefore, induction of BSP expression may be important for the osteoinductive property of oxysterols. The osteoinductive potential of oxysterols appears to increase when a double bond is added between C25 and C27 of 20(S)-hydroxycholesterol. Therefore, we envision all molecules and their variations that contain the basic structure of 20(S)-hydroxycholesterol with an added double bond at the end of the fatty acid side chain, for example, between C25 and C27, and a hydroxyl group on C6 of the B ring, as being useful for inducing osteogenesis, bone mineralization, and other biochemical phenomena. An example is Oxy49 shown below:

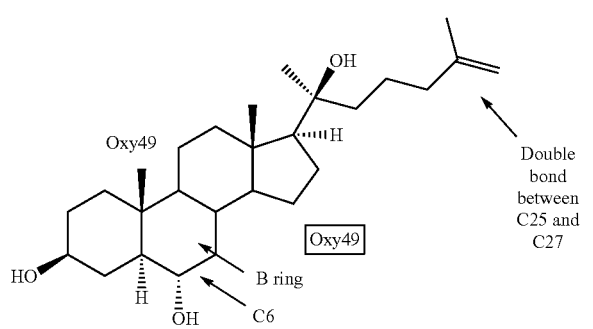

Synthesis Example 1

Oxy22

1-((3S,8S,9S,10R,13S,14S,17S)-2,3,4,7,8,9,10,11,12,13,14,15,16,17-Tetradecahydro-3-[(1,1-dimethylethyl)dimethylsilyloxy]-10,13-dimethyl-1H-cyclopenta[a]phenanthren-17-yl)ethanone (1)

To a stirred solution of pregnenolone (5.0 g, 15.8 mmol) in anhydrous dimethylformamide (DMF, 180 mL) was added imidazole (2.7 g, 39.7 mmol). The reaction was allowed to stir for 20 min followed by slow addition of tert-butyldimethylsilyl chloride (3.6 g, 23.9 mmol). After stirring for 12 h at ambient temperature, the reaction mixture was poured over ice. The precipitates were collected and dissolved in diethyl ether. The organic phases were washed with brine, dried over $Na_2SO_4$ and evaporated in vacuo to yield compound 1 (6.7 g, 15.6 mmol, 98%) as a white powder, which was used without further purification. The spectroscopic data were identical to those reported in the literature (66).

(3S,8S,9S,10R,13S,14S,17R)-17-(2,3,4,7,8,9,10,11,12,13,14,15,16,17-Tetradecahydro-17-((S)-2-Hydroxy-5-phenylpent-2-yl)10,13-dimethyl-1H-cyclopenta[a]phenanthren-3-ol (2, [Oxy22])

To a stirred suspension of magnesium turnings (106.7 mg, 4.4 mmol) in anhydrous diethyl ether (3.5 mL) was added (3-bromopropyl)benzene (199.0 mg, 1.22 mmol). After stirring under reflux for 2 h, the initially produced Grignard reagent was cannulated into a solution of the protected pregnenolone 1 (300 mg, 0.70 mmol) in anhydrous tetrahydrofuran (THF, 20 mL) and the solution was refluxed for an additional 2 h. The mixture was cooled in an ice bath and treated with satd. $NH_4Cl$. The solution was filtered through Celite and the precipitate washed three times with diethyl ether. The filtrate was extracted twice with diethyl ether. The organic layers were combined and washed with satd. NaCl, dried over $Na_2SO_4$ and evaporated in vacuo to afford a residue, which was subjected to flash column chromatography on silica gel. Elution with hexane-diethyl ether (2:1 v/v) afforded the alcohol. The silyl ether was then treated with a 1.0 M solution of tetrabutylammonium fluoride (TBAF) in THF (1.0 mL, 1.0 mmol), and the mixture was allowed to stir at 20° C. After stirring for 12 h, the reaction was treated with water and extracted three times with diethyl ether and the organic layer was washed with satd. NaCl. The organic phases were collected, dried over $Na_2SO_4$ and concentrated in vacuo to give an oil. Flash column chromatography of this oil (silica gel, 1:2 hexane/diethyl ether) yielded the diol 2 (170.0 mg, 56% over 2 steps) as a white powder.

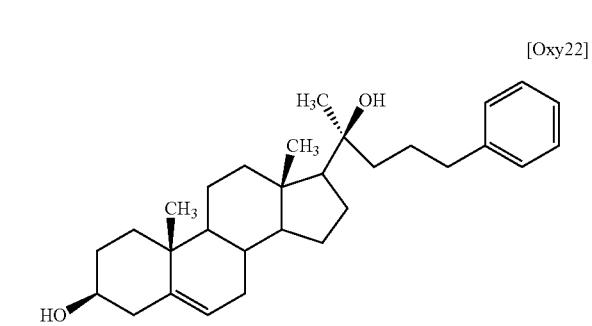 [SMILES: C[C@]12CCC3C(CC=C4C[C@@H](O)CC[C@@]43C)C1CCC2[C@@](C)(O)CCCc1ccccc1]

¹H NMR (CDCl₃; 400 MHz) δ: 7.30-7.26 (2H, m), 7.20-7.19 (3H, m), 5.35 (1H, m), 3.56-3.48 (1H, m), 2.61-2.56 (2H, m), 2.28-2.23 (2H, m), 2.20-2.17 (1H, m), 2.08-2.05 (1H, m), 1.85-1.39 (16H, m), 1.26 (3H, s), 1.18-1.07 (4H, m), 1.00 (3H, s), 0.85 (3H, s). ¹³C NMR (CDCl₃, 100 MHz) δ: 142.5, 140.8, 128.4, 128.3, 125.8, 121.6, 75.2, 71.7, 57.6, 56.9, 50.0, 43.6, 42.7, 42.3, 40.1, 37.2, 36.5, 31.8, 31.6, 31.3, 26,4, 26.41, 23.8, 22.3, 20.9, 19.4, 13.6.

Synthesis Example 2

Oxy27

(3S,8S,9S,10R,13S,14S,17S)-17-((S)-2-Hydroxy-4-phenylbutan-2-yl)-10,13-dimethyl-2,3,4,7,8,9,10,11,12,13,14,15,16,17-tetradecahydro-1H-cyclopenta[a]phenanthren-3-ol (3, [Oxy27])

The Grignard reagent prepared from (2-bromoethyl)benzene (958 mg, 5.17 mmol) in 10.0 mL of anhydrous diethyl ether in the presence of magnesium turnings (500 mg, 20.6 mmol) was added to pregnenolone 1 (300 mg, 0.69 mmol) under similar conditions to those described for the preparation of 2. Desilylation was carried out as above with TBAF to afford the diol 3 (Oxy27) (200.0 mg, 69% over 2 steps) as a white powder.

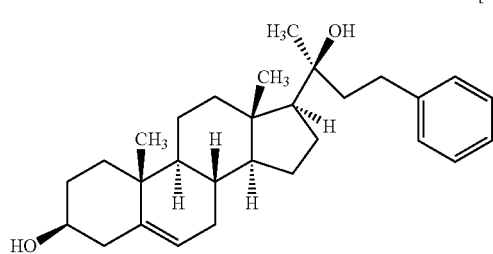

[Oxy27]

¹H NMR. (CDCl₃; 400 MHz) δ: 7.30-7.26 (2H, m), 7.20-7.19 (3H, m), 5.35 (1H, m), 3.56-3.48 (1H, m), 2.61-2.56 (2H, m), 2.28-2.23 (2H, m), 1.85-1.39 (16H, m), 1.26 (3H, s), 1.18-1.07 (4H, m), 1.00 (3H, s), 0.85 (3H, s). ¹³C NMR (CDCl₃, 100 MHz) δ: 142.5, 140.8, 128.4, 128.3, 125.8, 121.6, 75.2, 71.7, 57.6, 56.9, 50.0, 43.6, 42.7, 42.3, 40.1, 37.2, 36.5, 31.8, 31.3, 26.4, 26.41, 23.8, 22.3, 20.9, 19.4, 13.6.

Synthesis Example 3

Oxy26

(2S)-2-(3S,10R,13S)-3-[(1,1-Dimethylethyl)dimethylsilyloxy]-10,13-dimethyl-2,3,4,7,8,9,10,11,12,13,14,15,16,17-tetradecahydro-1H-cyclopenta[a]phenanthren-17-yl)-pent-4-yn-2-ol (4)

To a stirred suspension of magnesium turnings (6.0 g, 246.9 mmol) in anhydrous diethyl ether (150 mL) and mercuric chloride (700 mg, 2.6 mmol) was slowly added a solution of propargyl bromide (7.0 g, 58.8 mmol) in diethyl ether (50 mL). After stirring under reflux for 20 min, the initially produced Grignard reagent was cannulated into a solution of the protected pregnenolone 1 (4.5 g, 14.2 mmol) in anhydrous THF (20 mL) and the mixture was refluxed for an additional 1 h. The mixture was quenched with satd. NH₄Cl in an ice bath for 30 min and extracted three times with diethyl ether. The organic layer was washed with satd. NaCl. The organic phases were collected, dried over Na₂SO₄ and concentrated in vacuo to afford a crude yellow solid. Flash column chromatography (silica gel, 1:10 diethyl ether/hexane v/v) yielded the propargylic alcohol 4 (3.65 g, 72%) as a white powder. The spectroscopic data was identical to that reported in the literature (67).

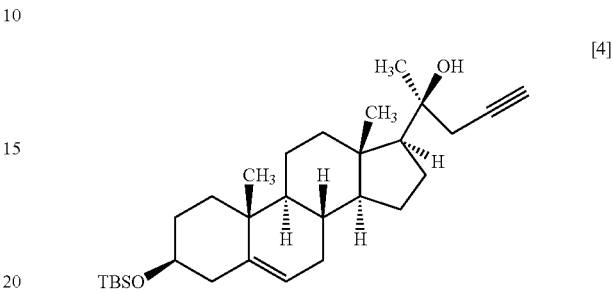

[4]

(S)-2-((3S,8S,9S,10R,13S,14S,17S)-3-[(1,1-Dimethylethyl)dimethylsilyloxy]-10,13-dimethyl,2,3,4,7,8,9,10,11,12,13,14,15,16,17-tetradecahydro-1H-cyclopenta[a]phen-anthren-17-yl)-5-(thiophen-2-yl)pent-4-yn-2-ol (5)

To a solution of the propargylic alcohol 4 (500 mg, 1.4 mmol) in anhydrous THF (8.0 mL) was added diisopropylethylamine (8.0 mL), 2-bromothiophene (680 mg, 4.2 mmol), Pd(PPh₃)₄ (81 mg, 0.070 mmol) and CuI (42 mg, 0.22 mmol) (68). The reaction mixture was refluxed under a nitrogen atmosphere for 12 h. The solvent was then removed under reduced pressure to give a residue which was purified by flash column chromatography (silica gel, 1:3 diethyl ether/hexane v/v) to afford the silyl ether 5 (160 mg, 21%) as an off-white powder.

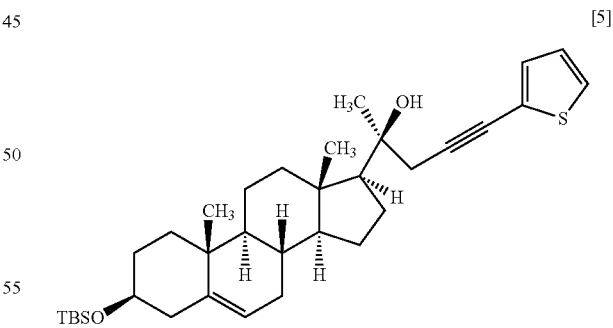

[5]

¹H NMR (CDCl₃; 400 MHz) δ: 7.19 (1H, dd, J=5.2, 1.2 Hz), 7.14 (1H, dd, J=3.6, 1.1 Hz), 6.95 (1H, dd, J=5.2, 3.6 Hz), 5.33-5.31 (1H, m), 3.52-3.44 (1H, m), 2.58 (1H, q, J=19.6 Hz), 2.19-1.49 (18H, m), 1.47 (3H, s), 1.26-1.03 (4H, m), 1.01 (3H, s), 0.89 (9H, s), 0.87 (3H, s), 0.06 (6H, s). ¹³C NMR (CDCl₃, 100 MHz) δ: 141.6, 131.3, 126.8, 126.3, 123.7, 121.1, 90.9, 89.9, 75.2, 74.5, 57.7, 56.9, 50.1, 42.8, 40.0, 37.4, 36.6, 35.2, 32.1, 32.0, 31.5, 31.4, 27.0, 26.0, 23.8, 22.5, 21.2, 19.4, 18.3, 13.5, −4.6.

(3S,8S,9S,10R,13S,14S,17S)-17-((S)-2-Hydroxy-5-(thiophen-2-yl)pent-4-yn-2-yl)-10,13-dimethyl-2,3,4,7,8,9,10,11,12,13,14,15,16,17-tetradecahydro-1H-cyclopenta-[a]phenanthren-3-ol (6, [Oxy26])

The silyl ether 5 (50 mg, 0.90 mmol) was dissolved in THF and treated with a 1.0 M solution of tetrabutylammonium fluoride in THF (2.0 mL, 2.0 mmol) and the mixture was allowed to stir at 20° C. After stirring for 12 h, the reaction was treated with water and extracted three times with diethyl ether and the organic layer was washed with satd. NaCl. The organic phases were collected, dried over $Na_2SO_4$ and concentrated in vacuo to give an oil. Flash column chromatography of this oil (silica gel, 1:3 hexane/diethyl ether v/v) yielded the diol 6 (Oxy26) (42.0 mg, 96%) as a white powder.

[Oxy26]

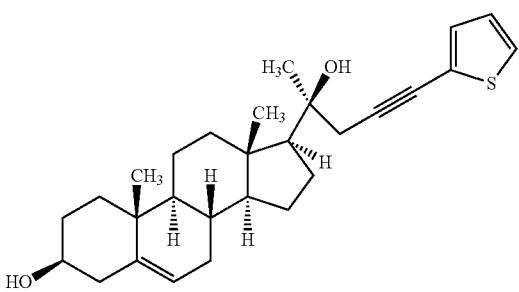

$^1$H NMR ($CDCl_3$; 400 MHz) δ: 7.19 (1H, dd, J=5.2, 1.2 Hz), 7.14 (1H, dd, J=3.6, 1.1 Hz), 6.95 (1H, dd, J=5.2, 3.6 Hz), 5.33-5.31 (1H, m), 3.52-3.44 (1H, m), 2.58 (1H, q, J=19.6 Hz), 2.19-1.49 (18H, m), 1.47 (3H, s), 1.26-1.03 (4H, m), 1.01 (3H, s), 0.87 (3H, s). $^{13}$C NMR ($CDCl_3$, 100 MHz) δ: 141.6, 131.3, 126.8, 126.3, 123.7, 121.1, 90.9, 89.9, 75.2, 74.5, 57.7, 56.9, 50.1, 42.8, 40.0, 37.4, 36.6, 35.2, 32.1, 32.0, 31.5, 31.4, 27.0, 23.8, 22.5, 21.2, 19.4, 13.5

Synthesis Example 4

Oxy39

(R)-2-((3S,8S,9S,10R,13S,14S,17S)-3-[(1,1-Dimethylethyl)dimethylsilyloxy]-10,13-dimethyl-2,3,4,7,8,9,10,11,12,13,14,15,16,17-tetradecahydro-1H-cyclopenta[a]phe-nanthren-17-yl)but-3-yn-2-ol (7)

To a solution of trimethylsilylacetylene (500 mg, 5.01 mmol) in 5.0 mL of anhydrous THF, was added n-butyllithium (1.0 mL, 2.5 mmol) at 0° C. After 30 min, a solution of the pregnenolone 1 (500 mg, 1.58 mmol) in THF (10 mL) was added slowly. The reaction was quenched after 1 h with satd. $NH_4Cl$ and extracted twice with diethyl ether. The organic layers were combined and washed with satd. NaCl, dried over $Na_2SO_4$ and evaporated in vacuo to afford a crude solid, which upon treatment with potassium carbonate (600 mg, 4.34 mmol) in 6.0 mL mixture of methanol/THF (5:1 v/v) yielded the crude desilylated propargylic alcohol. The solvent was removed and extracted with diethyl ether. The organic phases were collected, dried over $Na_2SO_4$ and evaporated in vacuo to give a residue which was purified by column chromatography on silica gel using hexane-diethyl ether (2:1 v/v) as eluent to afford the silyl ether 7 (360 mg, 78% over two steps) as a white solid.

[7]

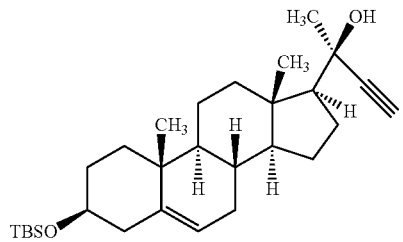

$^1$H NMR ($CDCl_3$; 400 MHz) δ: 5.32-5.31 (1H, m), 3.52-3.44 (1H, m), 2.51 (1H, s), 2.23-2.12 (5H, m), 1.99-1.95 (2H, m), 1.82-1.57 (9H, m), 1.49 (3H, s), 1.28-1.04 (5H, m), 0.98 (3H, s), 0.96 (3H, s), 0.83 (9H, s), 0.06 (6H, s). $^{13}$C NMR ($CDCl_3$, 100 MHz) δ: 141.7, 121.0, 87.5, 73.8, 72.6, 71.3, 60.0, 55.3, 50.1, 43.3, 42.8, 40.3, 37.4, 36.6, 32.8, 32.1, 31.9, 31 4, 26.0, 25.1, 24.2, 20.8, 19.5, 18.3, 13.4, −4.6.

(3S,8S,9S,10R,13S,14S,17S)-17-((S)-4-(2-Fluorophenyl)-2-hydroxybutan-2-yl)-10,13-dimethyl-2,3,4,7,8,9,10,11,12,13,14,15,16,17-tetradecahydro-1H-cyclopenta[a]phen-anthren-3-ol (8, [Oxy39])

To a solution of the propargylic alcohol 7 (300 mg, 0.66 mmol) in anhydrous THF (5.0 mL) was added diisopropylamine (5.0 mL), 2-fluoro-1-bromobenzene (404 mg, 2.3 mmol), $Pd(PPh_3)_4$ (42 mg, 0.036 mmol) and CuI (16 mg, 0.0.84 mmol) (68). The reaction mixture was refluxed under a nitrogen atmosphere for 12 h. The solvent was removed under reduced pressure to give a residue which was purified by flash column chromatography (silica gel, 1:3 diethyl ether/hexane v/v) to afford the aryl alkyne product (139 mg, 38%) as an off-white powder. Catalytic hydrogenation with Pd/C (10% mol) in ethyl acetate (3.0 mL) under a hydrogen atmosphere for 12 h afforded a crude mixture which was filtered through Celite using ethyl acetate and the solvent was removed under reduced pressure. This residue was treated with a 1.0 M solution of tetrabutylammonium fluoride in THF (2.0 mL, 2.0 mmol), and the mixture was allowed to stir at 20° C. After stirring for 12 h, the reaction was treated with water and extracted three times with diethyl ether and the organic layer was washed with satd. NaCl. The organic phases were collected, dried over $Na_2SO_4$ and concentrated in vacuo to give an oil. Flash column chromatography of this oil (silica gel, 1:3 hexane/diethyl ether v/v) afforded the diol 8 (Oxy39) in quantitative yield as a white powder.

[8] [Oxy39]

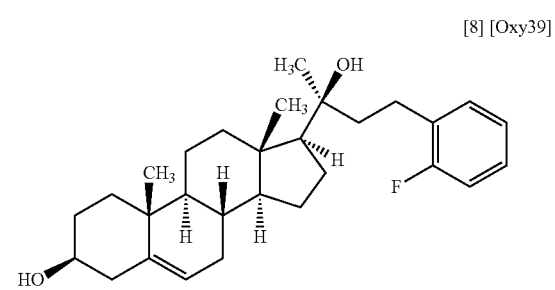

$^1$H NMR ($CDCl_3$; 400 MHz) δ: 7.20-7.13 (2H, m), 7.07-6.97 (2H, m), 5.331-5.32 (1H, m), 3.53-3.45 (1H, m), 2.66 (2H, t, J=19.6 Hz), 2.15-1.45 (18H, m), 1.39 (3H, s), 1.26-1.04 (6H, m), 1.01 (3H, s), 0.88 (3H, s). $^{13}$C NMR (CDCl$_3$, 100 MHz) δ: 163.1, 159.9, 141.6, 130.5, 130.4, 129.6, 129.4, 127.5, 127.4, 124.0, 123.9, 121.1, 115.3, 115.1, 75.1, 72.6, 58.0, 57.0, 50.1, 44.1, 42.8, 42.7, 40.2, 37.4, 36.7, 32.1, 31.8, 31.4, 26.1, 24.0, 23.8, 22.4, 20.9, 19.4, 13.6. $^{19}$F (CDCl$_3$; 400 MHz) δ: −119.7

Synthesis Example 5

Oxy42

(3S,8S,9S,10R,13S,14S,17S)-17-((S)-2-Hydroxy-5-(thiophen-2-yl)pentan-2-yl)-10,13-dimethyl-2,3,4,7,8,9,10,11,12,13,14,15,16,17-tetradecahydro-1H-cyclopenta[a]phen-anthren-3-ol (9, [Oxy42])

To a solution of the alkyne silyl ether 5 (40 mg, 0.72 mmol) in 2.0 mL of a mixture of dichloromethane/absolute ethanol (1:1 v/v), was added Pd/C (20% mol). The reaction was left under a hydrogen atmosphere for 12 h. The crude mixture was filtered through Celite using dichloromethane and the solvent was removed under reduced pressure. The residue was treated with a 1.0 M solution of tetrabutylammonium fluoride in THF (2.0 mL, 2.0 mmol), and the mixture was allowed to stir at 20° C. After stirring for 12 h, the reaction was treated with water and extracted three times with diethyl ether and the organic layer was washed with satd. NaCl. The organic phases were collected, dried over Na$_2$SO$_4$ and concentrated in vacuo to give an oil. Flash column chromatography of this oil (silica gel, 1:3 hexane/diethyl ether v/v) afforded the diol 9 (Oxy42) in quantitative yield as a white powder.

[9] [Oxy42]

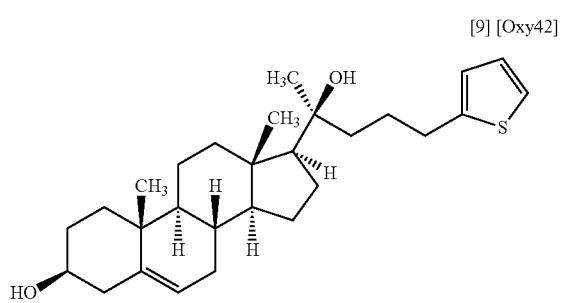

$^1$H NMR (CDCl$_3$; 400 MHz) δ: 7.19 (1H, dd, J=5.2, 1.2 Hz), 7.14 (1H, dd. J=3.6, 1.1 Hz), 6.95 (1H, dd, J=5.2, 3.6 Hz), 5.36-5.34 (1H, m), 3.55-3.51 (1H, m), 2.83-2.80 (2H, m), 2.29-1.45 (22H, m), 1.28 (3H, s), 1.26-1.03 (4H, m), 1.01 (3H, s), 0.86 (3H, s). $^{13}$C NMR (CDCl$_3$, 100 MHz) δ: 145.4, 140.8, 126.7, 124.1, 122.9, 121.6, 75.1, 71.8, 57.8, 56.9, 50.0, 43.3, 42.7, 42.3, 37.2, 36.5, 32.3, 31.8, 31.7, 31.6, 31.3, 30.4, 26.4, 23.8, 22.3, 20.9, 19.4, 13.6.

Synthesis Example 6

Oxy40

(3S,8S,9S,10R,13S,14S,17S)-2,3,4,7,8,9,10,11,12,13,14,15,16,17-Tdtradecahydro-3-[(1,1-dimethylethyl)dimethylsilyloxy]-17-((S)-2-hydroxy-6-methylhept-6-en-2-yl)-10,13-dimethyl-1H-cyclopenta[a]phenanthrene (10)

The coupling reaction of the protected pregnenolone 1 (500.0 mg, 1.16 mmol) with 5-bromo-2-methyl-1-pentene (199.0 mg, 1.22 mmol) in the presence of samarium diiodide was performed as reported (69a) to afford the 20S-hydroxy steroid 10 (419.0 mg, 0.82 mmol, 71%) as a white powder. The spectroscopic data were identical to those reported in the literature (69b).

[10]

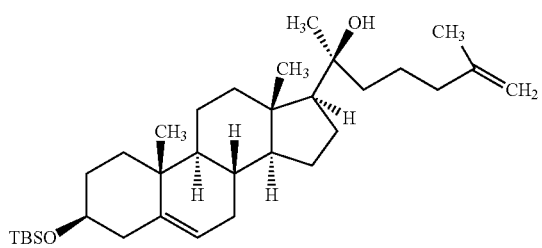

(S)-6-((3S,8S,9S,10R,13S,14S,17S)-3-[(1,1-Dimethylethyl)dimethylsilyloxy]-10,13-dimethyl,2,3,4,7,8,9,10,11,12,13,14,15,16,17-tetradecahydro-1H-cyclopenta[a]phen-anthren-17-yl)-2-methylheptane-1,6-diol (11)

To a solution of the dienyl silyl ether 10 (30 mg, 0.055 mmol) in THF (1.0 mL) cooled to 0° C. was added 0.08 mL of BH$_3$ (1.0 M in THF). The reaction was allowed to warm to 20° C. over 3 h. A mixture of 1.2 mL of NaOH (10%) and 0.3 mL of H$_2$O$_2$ (30%) was then added at 0° C. and the mixture was allowed to warm to 20° C. over 1 h (70a). The reaction mixture was extracted three times with diethyl ether. The organic phases were collected, dried over Na$_2$SO$_4$ and evaporated in vacuo to afford an oil. Flash column chromatography of this crude oil (silica gel, 1:1 hexane/diethyl ether v/v) afforded the diol 11 (12 mg, 40%) as a undetermined diastereomeric mixture.

[11]

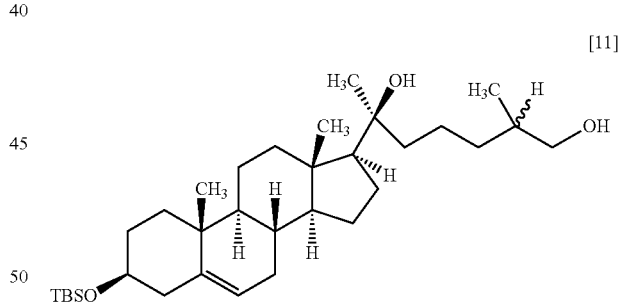

$^1$H NMR (CDCl$_3$; 500 MHz) δ: 5.32-5.31 (1H, m), 3.87-3.81 (2H, m), 3.52-3.48 (1H, m), 2.35-1.43 (22H, m), 1.25-1.24 (7H, m), 1.23 (3H, s), 1.09 (3H, s), 1.0 (3H, s), 0.90 (3H, dd, J=6.7, 2.7 Hz), 0.88 (9H, s), 0.05 (6H, s).

(6S)-6-(3S,8S,9S,10R,13S,14S,17S)-3-Hydroxy-10,13-dimethyl-2,3,4,7,8,9,10,11,12, 13,14,15,16,17-tetradecahydro-1H-cyclopenta[a]phenanthren-17-yl)-2-methylhep-tane-1,6-diol (12, [Oxy40])

The dihydroxy silyl ether 11 (12 mg, 0.023 mmol) was dissolved in THF and treated with a 1.0 M solution of tetrabutylammonium fluoride in THF (0.10 mL, 0.10 mmol), and the mixture was allowed to stir at 20° C. After stirring for 12 h, the reaction was treated with water and extracted three times with diethyl ether and the organic layer was washed with satd. NaCl. The organic phases were collected, dried over Na$_2$SO$_4$ and concentrated in vacuo to give an oil. Flash column chromatography of this oil (silica gel, 1:3 hexane/diethyl ether v/v) yielded the triol 12 (Oxy40) (12.0 mg, 96%).

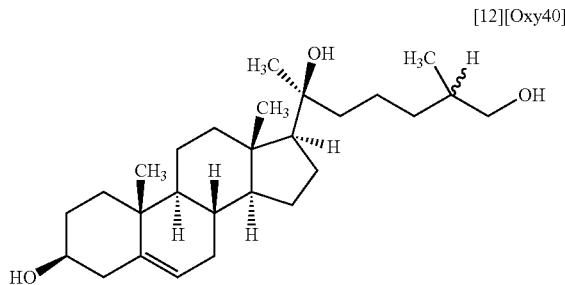

[12][Oxy40]

$^1$H NMR (CDCl$_3$; 500 MHz) δ: 5.32-5.31 (1H, m), 3.87-3.81 (2H, m), 3.52-3.48 (1H, m), 2.35-1.43 (22H, m), 1.25-1.24 (7H, m), 1.23 (3H, s), 1.09 (3H, s), 1.0 (3H, s), 0.90 (3H, dd, J=6.7, 2.7 Hz).

Synthesis Example 7

Oxy41

(6S)-6-((3S,5S,6S,8R,9S,10R,13S,14S,17S)-3-[(1,1-Dimethylethyl)dimethylsilyloxy]-6-hydroxy-10,13-dimethylhexadecahydro-1H-cyclopenta[a]phenanthren-17-yl)-2-methylheptane-1,6-diol (13)

To a solution of the dienyl silyl ether 10 (100 mg, 0.19 mmol) in THF (3.0 mL) at 0° C., added 1.0 M of BH$_3$ in THF (2.0 mL, 2.0 mmol). The reaction was allowed to warm to 20° C. over 3 h. A mixture of 5.0 mL of NaOH (10%) and 1.5 mL of H$_2$O$_2$ (30%) was then added at 0° C. and the mixture was allowed to warm to 20° C. over 1 h. The reaction mixture was extracted three times with diethyl ether. The organic phases were collected, dried over Na$_2$SO$_4$ and evaporated in vacuo to afford an oil. Flash column chromatography of this crude oil (silica gel, 1:4 hexane/diethyl ether v/v) afforded the trihydroxy silyl ether 13 (70 mg, 52%) as an undetermined diastereomeric mixture.

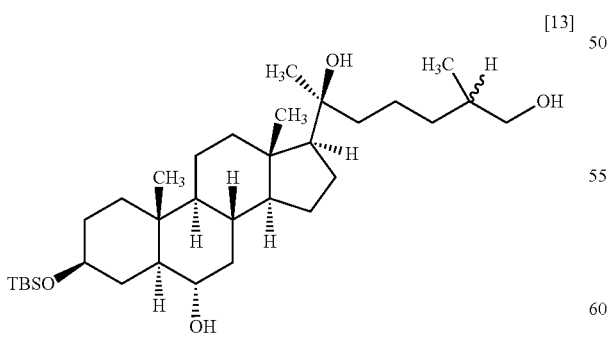

[13]

$^1$H NMR (CDCl$_3$; 500 MHz) δ: 3.62-3.48 (2H, m), 3.43-3.37 (2H, m), 1.20-0.94 (31H, m), 0.90 (3H, dd, J=6.7, 2.7 Hz), 0.88 (9H, s), 0.86 (3H, s), 0.82 (3H, s), 0.08 (3H, s), 0.05 (6H, s), $^{13}$C NMR (CDCl$_3$, 125 MHz) δ: 75.0, 71.9, 69.4, 68.2, 68.1, 56.2, 54.2, 53.7, 51.7, 43.0, 42.8, 41.5, 41.0, 40.1, 39.8, 37.3, 36.1, 35.6, 33.5, 32.4, 31.5, 25.8, 23.6, 22.5, 21.2, 20.9, 16.6, 13.6, 13.4, −4.7.

(3S,5S,6S,8R,9S,10R,13S,14S,17S)-3-Hydroxy-17-((S)-2-hydroxy-6-methylhept-6-en-2-yl)-10,13-dimethylhexadecahydro-1H-cyclopenta[a]phenanthren-6-yl acetate (14, [Oxy41])

To a solution of the trihydroxy silyl ether 13 (50 mg, 0.071 mmol) in anhydrous dichloromethane (2.0 mL) was added dimethylaminopyridine (14.4 mg, 0.12 mmol) followed by p-toluenesulfonyl chloride (15 mg, 0.079 mmol). After stirring for 3 h, the reaction was treated with satd. NaHCO$_3$ and extracted three times with dichloromethane. The organic phases were collected, dried over Na$_2$SO$_4$ and concentrated under reduced pressure. Flash column chromatography (silica gel, 1:4 hexane/diethyl ether v/v) yielded the tosylate intermediate (35.0 mg, 70%) as a white powder. Treatment of this crude material with 5.0 mL of acetic anhydride and pyridine mixture (1:1 v/v) (70b) followed by purification via flash column chromatography (silica gel, 1:2 hexane/diethyl ether v/v) afforded the tosyloxy acetate in quantitative yield.

To a solution of the acetate intermediate (35 mg, 0.050 mmol) in anhydrous acetonitrile (3.0 mL) was added lithium iodide (60 mg, 0.45 mmol). The reaction was refluxed for 3 h. The mixture was then treated with water and extracted three times with diethyl ether. The organic phases were collected, dried over Na$_2$SO$_4$ and concentrated under reduced pressure. The crude residue was treated with 1,8-diazabicyclo[5.4.0]undec-7-ene (DBU) (15 mg, 0.099 mmol) in 3.0 mL of acetonitrile and refluxed for 2 h (70c). The reaction was treated with satd. NH$_4$Cl and extracted with diethyl ether. The organic phases were dried over Na$_2$SO$_4$ and concentrated under reduced pressure. Deprotection of the tert-butyldimethylsilyl ether was performed under conditions similar to those described for the preparation of 12 to afford the alkene acetate 14 (Oxy41) in quantitative yield.

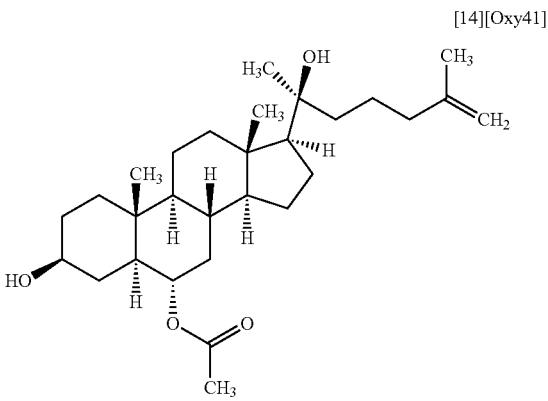

[14][Oxy41]

$^1$H NMR (CDCl$_3$; 500 MHz) δ: 4.70-4.65 (3H, M), 3.57-3.54 (1H, m), 2.03 (3H, s), 2.01-1.71 (6H, m), 1.61 (3H, s), 1.57-1.31 (16H, m), 1.27 (3H, s) 1.21-0.90 (7H, m), 0.86 (3H, s), 0.83 (3H, s). $^{13}$C NMR (CHCl$_3$, 125 MHz) δ: 170.7, 145.7, 109.9, 72.4, 70.9, 57.6, 56.2, 53.5, 48.6, 43.4, 42.9, 40.0, 38.1, 37.4, 37.1, 36.5, 33.4, 32.1, 31.0, 29.6, 26.2, 23.6, 22.3, 22.2, 22.1, 21.2, 20.9, 13.6, 13.3.

Synthesis Example 8

Oxy48

(3S,5S,6S,8R,9S,10R,13S,14S,17S)-17-((2S)-2,7-Dihydroxy-6-methylheptan-2-yl)-10,13-dimethyl-liexadecahydro-1H-cyclopenta[a]phenanthrene-3,6-diol (15, [Oxy48])

Deprotection of the tert-butyldimethylsilyl ether 13 was performed under conditions similar to those described for the preparation of 12 to afford 15 (Oxy48) in quantitative yield.

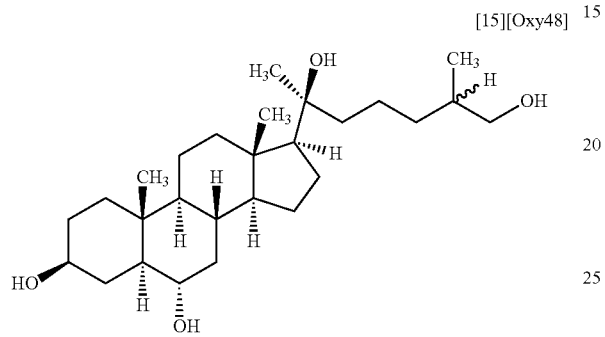

[15][Oxy48]

$^1$H NMR (CDCl$_3$; 500 MHz) δ: 3.62-3.48 (2H, m), 3.43-3.37 (2H, m), 1.20-0.94 (32H, m), 0.90 (3H, dd, J=6.7, 2.7 Hz), 0.86 (3H, s), 0.82 (3H, s), 0.08 (3H, s). $^{13}$C NMR (CDCl$_3$, 125 MHz) δ: 75.0, 71.9, 69.4, 68.2, 68.1, 56.2, 53.7, 51.7, 43.0, 42.8, 41.5, 41.0, 40.1, 39.8, 37.3, 36.1, 35.6, 33.5, 32.4, 31.5, 23.6, 22.5, 21.2, 20.9, 16.6, 13.6, 13.4.

Synthesis Example 9

Oxy49

(3S,5S,6S,8R,9S,10R,13S,14S,17S)-17-((S)-2-Hydroxy-6-methylhept-6-en-2-yl)-10,13-dimethylhexadecahydro-1H-cyclopenta[a]phenanthrene-3,6-diol (16, [Oxy49])

To a solution of the acetate 14 (10 mg, 0.022 mmol) in methanol (1.0 mL) was added KOH (4 mg, 0.073 mmol) and the mixture was allowed to stir for 1 h. The solvent was then removed in vacuo to yield a crude residue which was purified by flash column chromatography (silica gel, 5% methanol in diethyl ether) to afford the alkene triol 16 (Oxy49) in quantitative yield.

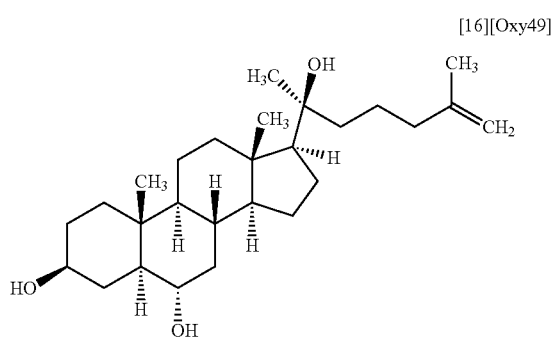

[16][Oxy49]

$^1$H NMR (CDCl$_3$; 500 MHz) δ: 4.70-4.67 (2H, m0, 3.50-3.49 (1H, m), 3.45-3.35 (1H, m), 1.98-1.70 (10H, m), 1.71 (3H, s), 1.45-1.31 (10H, m), 1.25 (3H, s), 1.19-0.88 (10H, m), 0.86 (3H, s), 0.82 (3H, s). $^{13}$C NMR (CDCl$_3$, 125 MHz) δ: 145.7, 109.9, 72.4, 70.9, 57.6, 56.2, 53.5, 48.6, 43.4, 42.9, 40.0, 38.1, 37.4, 37.1, 36.5, 33.4, 32.1, 31.0, 29.6, 26.2, 23.6, 22.3, 22.2, 22.1, 21.2, 13.6, 13.3.

Synthesis Example 10

Oxy28

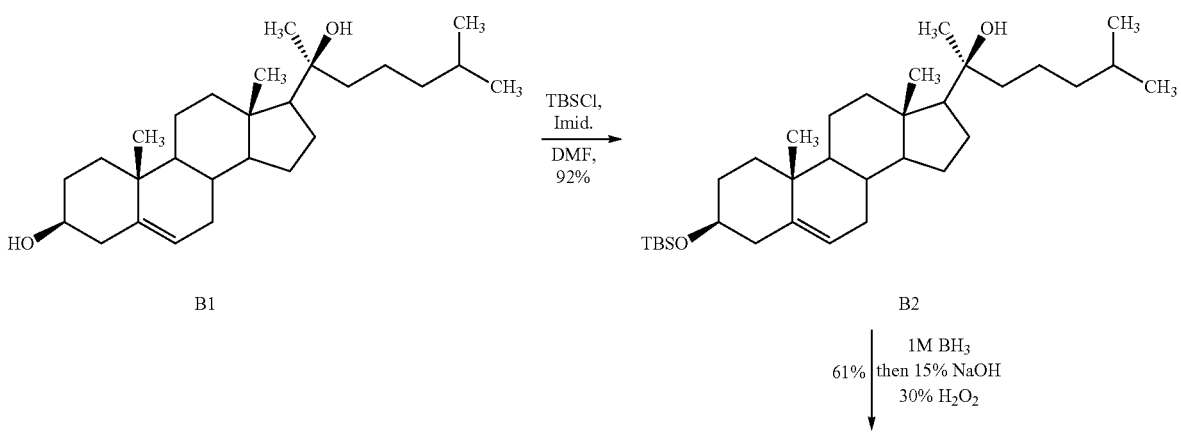

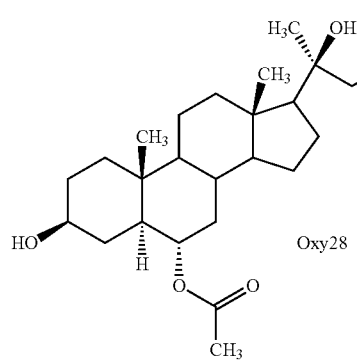

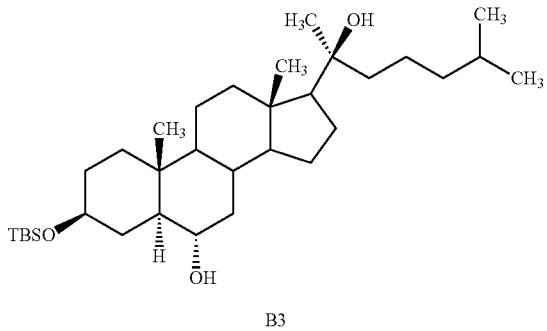

To a stirred solution of B1 (18.0 mg, 0.045 mmol) and imidazole (9.1 mg, 0.134 mmol) in DMF (3 mL) was added TBSCl (8.8 mg, 0.058 mmol) at 0° C. The reaction was allowed to warm to 23° C. and stirred overnight. The reaction was quenched with 50% $NH_4Cl$ (10 mL) and extracted with diethyl ether (15 mL). The combined organic layers were dried over $MgSO_4$, concentrated under vacuum and purified by column chromatography (33% ethyl acetate in hexane) to yield 21.3 mg (92%) of B2 as a white solid. $^1H$ NMR δ 5.31 (m, 1H), 3.48 (m, 1H), 2.31-0.83 (m, 27H), 1.27 (s, 3H), 1.00 (s, 3H), 0.89 (s, 9H), 0.87 (d, 6H, J=6.7 Hz), 0.86 (s, 3H), 0.05 (s, 6H).

To a solution of B2 (18.0 mg, 0.035 mmol) in THF (1 mL) was added 1.0 M borane in THF (0.098 mL, 0.098 mmol) at 0° C., and the reaction mixture was stirred for 14 h at 23° C. 15% aqueous sodium hydroxide solution (0.3 mL) and 30% hydrogen peroxide (0.15 mL) were added to the reaction mixture at 0° C. After being stirred for 4 h at 23° C., the reaction mixture was diluted with water and the crude product was isolated by ethyl acetate extraction. Concentration gave an oily product which was purified by flash column chromatography. Elution with 20% ethyl acetate in hexane gave alcohol B3 (11.4 mg, 61%) as a colorless oil. $^1H$ NMR δ 3.52 (m, 1H), 3.40 (m, 1H), 2.17-0.57 (m, 28H), 1.26 (s, 3H), 0.88 (s, 9H), 0.88 (s, 3H), 0.86 (s, 3H), 0.82 (d, 6H, J=8.4 Hz), 0.05 (s, 6H).

To a solution of the alcohol B3 (5.0 mg, 0.009 mmol), triethylamine (0.013 mL, 0.093 mmol) and 4-(dimethylamino)pyridine (0.1 mg, 0.001 mmol) in $CH_2Cl_2$ (3 mL) was added acetic anhydride (0.005 mL, 0.047 mmol). The reaction was stirred at 23° C. until TLC indicated completion of the reaction. The reaction was diluted with diethyl ether (15 mL) and quenched with water (10 mL). The organic phase was separated, dried over $MgSO_4$, concentrated under vacuum and then purified by column chromatography (20% ethyl acetate in hexane) to give 5.0 mg (93%) of the desired acetate.

This acetate (3.0 mg, 0.005 mmol) was dissolved in methanol (1 mL). Catalytic amount of p-toluenesulfonic acid (0.2 mg, 0.001 mmol) was then added and the reaction mixture was stirred at 23° C. until TLC indicated completion of the reaction. The reaction was diluted with ethyl acetate (10 mL) and quenched with 5% $NaHCO_3$ solution (5 mL). The organic phase was separated, dried over $MgSO_4$, concentrated under vacuum and then purified by column chromatography (50% ethyl acetate in hexane) to give 1.7 mg (72%) of the desired acetate B4 (Oxy28). $^1H$ NMR δ 4.68 (m, 1H), 3.55 (m, 1H), 2.17-0.57 (m, 28H), 2.03 (s, 3H), 1.26 (s, 3H), 0.87 (d, 6H, J=6.5 Hz), 0.87 (s, 3H), 0.83 (s, 3H).

Synthesis Example 11

Oxy51

(3S,8S,9S,10R,13S,14S,17S)-10,13-dimethyl-17-(2-methyl-1,3-dioxolan-2-yl)-2,3,4,7, 8,9,10,11,12,13, 14,15,16,17-tetradecahydro-1H-cyclopenta[a] phenanthren-3-yl acetate (C1)

To a solution of pregnenolone acetate (11.4 g, 32 mmol) in 160 mL benzene were added pyridinium p-toluene sulfonate (1.61 g, 6.4 mmol) and ethylene glycol (5.5 mL, 6.12 g, 98.6 mmol). The mixture was refluxed under Dean-Stark apparatus at 110° C. for 12 h. The reaction mixture was diluted with diethyl ether, washed with water and satd NaCl sequentially, dried over $Na_2SO_4$ and concentrated in vacuo. Purification of the crude solid by recrystallization in hot hexane provided acetal C1 (10 g, 78%) as colorless crystals.

[C1]

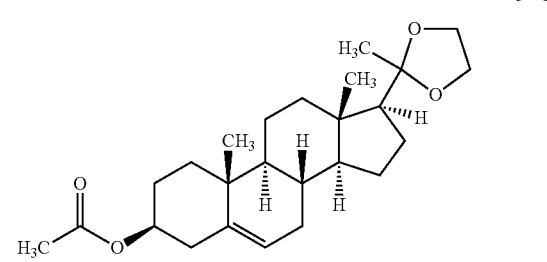

$^1H$ NMR (CDCl$_3$; 400 MHz) δ: 5.37-5.36 (1H, m), 4.63-4.56 (1H, m), 4.02-3.82 (4H, m), 2.32-2.29 (1H, m), 2.02 (3H, s), 1.87-1.43 (16H, m), 1.29 (3H, s), 1.23-1.06 (3H, m), 1.01 (3H, s), 0.77 (3H, s). $^{13}C$ NMR (CDCl$_3$, 100 MHz) δ: 170.5, 139.7, 122.5, 112.0, 74.0, 65.2, 63.2, 58.2, 56.5, 50.0, 41.8, 39.4, 38.1, 37.0, 36.6, 31.8, 31.4, 27.8, 24.6, 23.8, 23.0, 21.4, 20.8, 19.3, 12.9.

1-((3S,5S,6S,8R,9S,10R,13S,14S,17S)-3,6-bis(tert-butyldimethylsilyloxy)-10,13-dimethylhexadeca-hydro-1H-cyclopenta[a]phenanthren-17-yl)ethanone (C2)

To a solution of acetal C1 (5.0 g, 12 mmol) in THF (150 mL) at 0° C., was added 1.0 M $BH_3$ in THF (40.0 mL, 40 mmol). The reaction was allowed to warm to 20° C. over 5 h. Upon completion, a mixture of 150 mL of NaOH (10%) and 75 mL of $H_2O_2$ (33%) was added at 0° C. and allowed to warm to 20° C. over 4 h. The reaction mixture was extracted three times with diethyl ether (100 mL×3). The organic phases were collected, dried over $Na_2SO_4$ and evaporated in vacuo to afford an oil. The crude acetal diol (5.1 g, 13.5 mmol) was dissolved in acetone (250 mL) and treated with 1 M HCl (50 mL, 50 mmol). After 30 min under reflux, the resulting mixture was quenched with 1 M NaOH at 0° C. and the organic solvent was evaporated. The aqueous layer was extracted with diethyl ether three times (50 mL×3). The organic layer was washed with satd. NaCl, dried over $Na_2SO_4$, and concentrated under reduced pressure. The crude ketone (4.32 g, 12.9 mmol) was dissolved in anhydrous dimethylformamide (DMF, 50 mL) and imidazole (15.0 g. 22 mmol) was added. The reaction was allowed to stir for 20 min followed by slow addition of tert-butyldimethylsilyl chloride (9.8 g, 65 mmol). After stirring for 12 h at ambient temperature, the reaction mixture was quenched with water and extracted three times with diethyl ether (150 mL×3). The organic layers were washed with 1 M NaOH, dried over $Na_2SO_4$ and evaporated in vacuo to give an oil. Purification of the residue by column chromatography (silica gel, 5:1 hexane/diethyl ether v/v) afforded bis(tert-butyldimethylsilyloxy) ketone C2 (3.5 g, 52% over three steps) as a white powder.

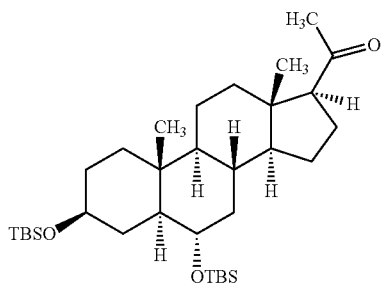
[C2]

$^1$H NMR (CDCl$_3$; 400 MHz) δ: 3.54-3.46 (1H, m), 3.39-3.33 (1H, m), 2.53 (1H, t, J=8.8 Hz), 2.20-2.14, (1H, m), 2.10 (3H, s), 2.01-1.97 (1H, m), 1.88-1.82 (1H, m), 1.73-0.89 (17H, m), 0.88 (18H, s), 0.79 (3H, s), 0.59 (3H, s), 0.043 (3H, s), 0.040 (3H, s), 0.03 (3H, s), 0.02 (3H, s). $^{13}$C NMR (CDCl$_3$, 100 MHz) δ: 209.5, 72.2, 70.1, 63.7, 56.4, 53.7, 51.8, 44.2, 41.9, 38.9, 37.6, 36.3, 34.3, 33.2, 31.7, 31.5, 25.94, 25.92, 24.4, 22.7, 21.1, 18.3, 18.1, 13.5, 13.4, −4.06, −4.61, −4.69, −4.73.

(S)-2-((3S,5S,6S,8R,9S,10R,13S,14S,17S)-3,6-bis(tert-butyldimethylsilyloxy)-10,13-dimethylhexadecahydro-1H-cyclopenta[a]phenanthren-17-yl)pent-4-yn-2-ol (C3)

To a stirred suspension of magnesium turnings (4.0 g, 164.6 mmol) was slowly added a solution of propargyl bromide (4.0 g, 33.7 mmol) in diethyl ether (50 mL) and mercuric chloride (cat). After stirring under reflux for 20 min, the initially produced Grignard reagent was cannulated into a solution of bis(tert-butyldimethylsilyloxy) C2 (2.74 g, 4.9 mmol) in anhydrous THF (150 mL) and left under reflux for an additional 1 h. The mixture was quenched with satd. NH$_4$Cl over an ice bath for 30 min and extracted three times with diethyl ether. The organic layer was washed with satd. NaCl. The organic phases were collected, dried over $Na_2SO_4$ and concentrated in vacuo to afford a crude yellow solid. Flash column chromatography (silica gel, 3:1 hexane/diethyl ether v/v) yielded bis(tert-butyldimethylsilyloxy) propargyl alcohol C3 (2.61 g, 88%) as a white powder.

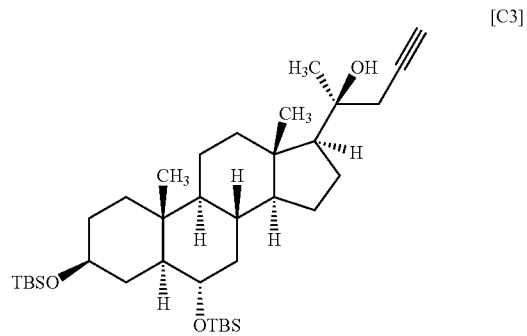
[C3]

$^1$H NMR (CDCl$_3$; 400 MHz) δ: 3.53-3.44 (1H, m), 3.38-3.32 (1H, m), 2.38-2.34 (1H, dd, J=16.4, 2.4 Hz), 2.29-2.24 (1H, dd, J=16.4, 2.8 Hz), 2.04 (1H, t, J=2.4 Hz), 1.85-1.63 (11H, m), 1.39 (3H, s), 1.27-0.89 (11H, m), 0.87 (18H, s), 0.81 (3H, s), 0.79 (3H, s), 0.033 (3H, s), 0.030 (3H, s), 0.02 (3H, s), 0.01 (3H, s). $^{13}$C NMR (CDCl$_3$, 100 MHz) δ: 81.2, 73.9, 72.3, 71.2, 70.3, 57.4, 56.3, 53.7, 51.8, 42.9, 41.8, 40.0, 37.6, 36.3, 33.9, 33.7, 33.2, 31.7, 26.7, 25.9, 23.7, 22.3, 21.0, 18.3, 18.1, 13.6, 13.5, −4.03, −4.60, −4.67, −4.72.

(S)-2-((3S,5S,6S,8R,9S,10R,13S,14S,17S)-3,6-bis(tert-butyldimethylsilyloxy)-10,13-dimethylhexadecahydro-1H-cyclopenta[a]phenanthren-17-yl)-5-(thiophen-2-yl)pent-4-yn-2-ol (C4)

To a solution of bis(tert-butyldimethylsilyloxy) propargyl alcohol C3 (200 mg, 0.33 mmol) in anhydrous tetrahydrofuran (4.0 mL) was added diisopropylethylamine (4.0 mL), 2-bromothiophene (0.1 mL, 170 mg, 1.02 mmol), Pd(PPh$_3$)$_4$ (60 mg, 0.052 mmol), and CuI (30 mg, 0.48 mmol). The reaction mixture was heated at 70° C. under N$_2$ atmosphere for 4.5 h. Upon completion, the solvent was removed under reduced pressure followed by flash column chromatography (silica gel, 1:3 diethyl ether/hexane v/v) to afford bis(tert-butyldimethylsilyloxy) thiophene C4 (184 mg, 81%) as an off-white powder.

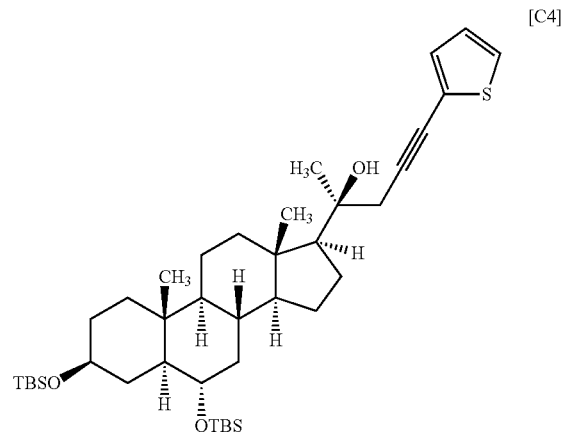
[C4]

$^1$H NMR (CDCl$_3$; 400 MHz) δ: 7.19 (1H, dd, J=5.2, 1.2 Hz), 7.14 (1H, dd, J=3.6, 0.8 Hz), 6.94 (1H, dd, J=5.2, 3.6 Hz), 3.60-3.52 (1H, m), 3.44-3.38 (1H, m), 2.56 (2H, q, J=16.8 Hz), 2.11-1.49 (10H, m), 1.45 (3H, s), 1.29-0.91 (12H, m), 0.89 (18H, s), 0.84 (3H, s), 0.81 (3H, s), 0.051 (3H, s), 0.49 (3H, s), 0.038 (3H, s), 0.033 (3H, s). $^{13}$C NMR (CDCl$_3$, 100 MHz) δ: 131.2, 126.7, 126.1, 123.6, 90.7, 76.4, 74.3, 72.2, 70.2, 57.6, 56.2, 53.6, 51.7, 42.9, 41.7, 39.9, 37.5, 36.1, 35.1, 33.6, 33.1, 31.6, 26.9, 25.8, 23.6, 22.3, 20.9, 18.2, 17.9, 13.5, 13.4, −4.2, −4.73, −4.79, −4.84.

(3S,5S,6S,8R,9S,10R,13S,14S,17S)-17-((S)-2-hydroxy-5-(thiophen-2-yl)pent-4-yn-2-yl)-10,13-dimethylhexadecahydro-1H-cyclopenta[a]phenanthrene-3,6-diol (C5, [Oxy51])

Compound C4 (80 mg, 0.90 mmol) was dissolved in 6.0 mL of THF/CH$_3$CN (1:1 v/v) and treated with HF/pyridine (0.1 mL). After stirring for 1 h at 20° C., the reaction was treated with water and extracted three times with diethyl ether (10 mL×3). The combined organic layers were washed with satd. NaHCO$_3$ followed by satd. NaCl. The organic phases were collected, dried over Na$_2$SO$_4$ and concentrated in vacuo to give an oil. Flash column chromatography of the residue (silica gel, 5% methanol/95% diethyl ether) yielded C5 (Oxy51) (37.7 mg, 69%) as a white powder.

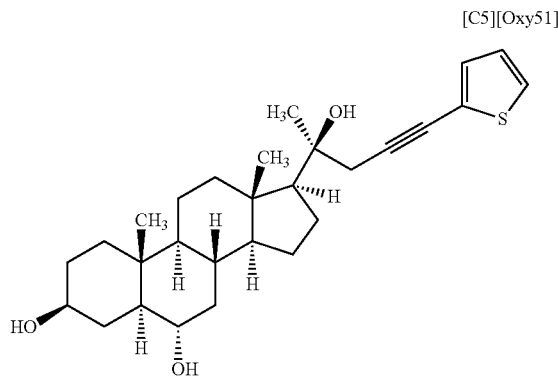

[C5][Oxy51]

$^1$H NMR (CDCl$_3$; 400 MHz) δ: 7.19 (1H, dd, J=5.2, 1.2 Hz), 7.14 (1H, dd, J=3.6, 0.8 Hz), 6.94 (1H, dd, J=5.2, 3.6 Hz), 3.60-3.52 (1H, m), 3.44-3.38 (1H, m), 2.56 (2H, q, J=16.8 Hz), 2.11-1.49 (12H, m), 1.45 (3H, s), 1.29-0.91 (12H, m), 0.84 (3H, s), 0.81 (3H, s). $^{13}$C NMR (CDCl$_3$, 100 MHz) δ: 131.4, 126.8, 126.3, 123.6, 90.8, 76.5, 74.4, 71.2, 69.4, 57.7, 56.3, 53.7, 51.7, 43.0, 41.4, 39.9, 37.3, 36.3, 33.7, 32.3, 30.9, 29.7, 26.9, 23.7, 22.4, 21.0, 13.6, 13.5.

Synthesis Example 12

Oxy50

(3S,5S,6S,8R,9S,10R,13S,14S,17S)-17-((S)-2-hydroxy-5-(thiophen-2-yl)pentan-2-yl)-10,13-dimethylhexadecahydro-1H-cyclopenta[a]phenanthrene-3,6-diol (C6, [Oxy50])

To a solution of compound C4 (10 mg, 0.015 mmol) in 2.0 mL mixture of dichloromethane/95% ethanol (1:1 v/v), was added 5% anhydrous Pd/C (3.4 mg). The reaction was left under H$_2$ atmosphere for 8 h. Upon completion, the crude mixture was filtered through Celite using dichloromethane and the solvent was removed under reduced pressure. The crude product (10 mg, 0.90 mmol) was dissolved in THF/CH$_3$CN (0.6 mL, 1:1 v/v) and treated with HF/pyridine (20 μL). After stirring for 1 h at 20° C., the reaction was treated with water and extracted three times with diethyl ether (10 mL×3). The combined organic layers were washed with satd. NaHCO$_3$ followed by satd. NaCl. The organic phases were collected, dried over Na$_2$SO$_4$ and concentrated in vacuo to give an oil. Flash column chromatography of the residue (silica gel, 5% methanol/95% diethyl ether) yielded C6 (Oxy50) (42.0 mg, 96%) as a white powder.

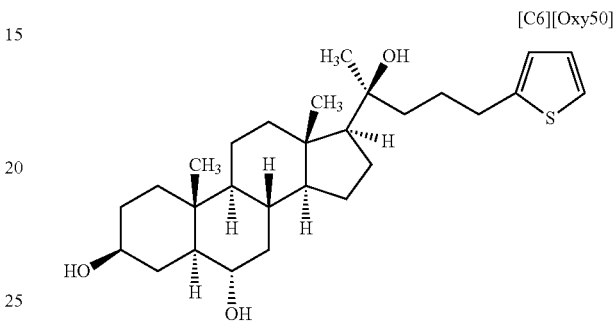

[C6][Oxy50]

$^1$H NMR (CDCl$_3$; 500 MHz) δ: 7.11 (1H, dd, J=5.2, 1.2 Hz), 6.91 (1H, dd, J=5.1, 3.4 Hz), 6.78-6.77 (1H, m), 3.60-3.54 (1H, m), 3.44-3.39 (1H, m), 2.86-2.75 (2H, m), 2.19-1.40 (18H, m), 1.26 (3H, s), 1.22-0.83 (10H, s), 0.82 (3H, s), 0.81 (3H, s). $^{13}$C NMR (CDCl$_3$, 125 MHz) δ: 145.2, 126.6, 124.0, 122.8, 74.9, 71.1, 69.3, 57.7, 56.2, 53.6, 51.5, 43.1, 42.8, 41.4, 40.3, 37.1, 36.1, 33.5, 32.1, 30.9, 30.3, 26.5, 26.2, 23.5, 22.2, 20.9, 13.6, 13.3.

Synthesis Example 13

Oxy53

(3S,5S,6S,8R,9S,10R,13S,14S,17S)-17-((S)-2-hydroxy-5-phenylpentan-2-yl)-10,13-dimethylhexadecahydro-1H-cyclopenta[a]phenanthrene-3,6-diol (C7, [Oxy53])

To a stirred suspension of magnesium turnings (1.3 g, 53.5 mmol) was added 1-bromo-3-phenylpropane (2.1 g, 10.5 mmol) in anhydrous diethyl ether (10 mL). After stirring under reflux for 30 min, the initially produced Grignard reagent was cannulated into a solution of bis(tert-butyldimethylsilyloxy) ketone C2 (300 mg, 0.53 mmol) in anhydrous THF (15 mL) and left under reflux. After 12 h, the mixture was quenched with satd. NH$_4$Cl at 0° C. extracted twice with diethyl ether. The organic layers were combined and washed with satd. NaCl, dried over Na$_2$SO$_4$ and evaporated in vacuo to afford a residue, which was subjected to column chromatography on silica gel. Elution with hexane-diethyl ether (5:1 v/v) afforded the alcohol (200 mg, 55%) followed by desilylation with HF/pyridine (0.24 mL) in THF/CH$_3$CN (12 mL, 1:1 v/v). After stirring for 1 h at 20° C., the reaction was treated with water and extracted three times with diethyl ether (10 mL×3). The organic layers were combined and washed with satd. NaHCO$_3$ followed by satd. NaCl. The organic phases were collected, dried over Na$_2$SO$_4$ and concentrated in vacuo to give an oil. Flash column chromatography (silica gel, 5% methanol/95% diethyl ether) yielded triol C7 (Oxy53) (100 mg, 76%) as a white powder.

[C7][Oxy53]

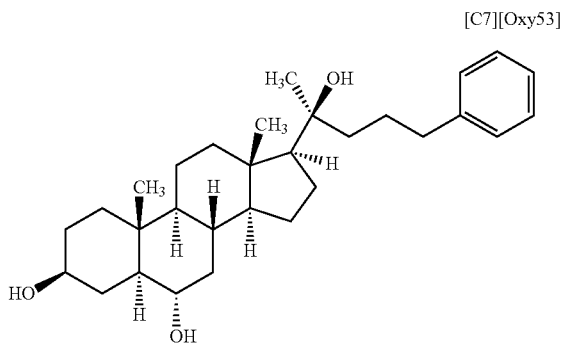

¹H NMR (CDCl₃; 400 MHz) δ: 7.29-7.25 (2H, m), 7.19-7.16 (3H, m), 3.61-3.53 (1H, m), 3.44-3.38 (1H, m), 2.64-2.52 (2H, m), 2.21-1.29 (19H, m), 1.25 (3H, s), 1.32-0.88 (9H, m), 0.82 (3H, s), 0.81 (3H, s). ¹³C NMR (CDCl₃, 100 MHz) δ: 142.5, 128.4, 128.3, 125.8, 75.1, 71.2, 69.4, 57.7, 56.3, 53.7, 51.7, 43.6, 42.9, 41.5, 40.2, 37.3, 36.5, 36.3, 33.6, 32.3, 31.0, 26.4, 23.7, 22.3, 21.9, 21.0, 13.7, 13.5.

Synthesis Example 14

Oxy52

(3S,5S,6S,8R,9S,10R,13S,14S,17S)-17-((S)-2-hydroxy-4-phenylbutan-2-yl)-10,13-dimethylhexadecahydro-1H-cyclopenta[a]phenanthrene-3,6-diol (C8, [Oxy52])

The Grignard addition to bis(tert-butyldimethylsilyloxy) ketone C2 (300 mg, 0.53 mmol) with (2-bromoethyl)benzene (940 mg, 5.1 mmol) in 5.0 mL of anhydrous diethyl ether in the presence of magnesium turnings (620 mg, 25.5 mmol) was performed under similar conditions as described for the preparation of Oxy53 followed by desilylation as above with HF/pyr to afford C8 (Oxy52) (200.0 mg, 86% over 2 steps) as a white powder.

[C8][Oxy52]

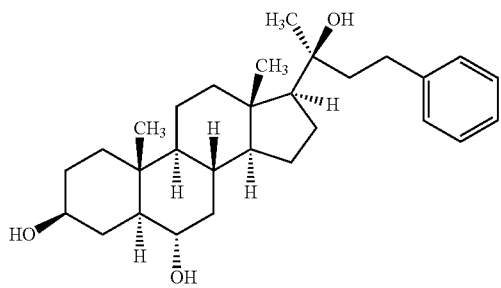

¹H NMR (CDCl₃; 400 MHz) δ: 7.29-7.25 (2H, m), 7.21-7.17 (3H, m), 3.62-3.54 (1H, m), 3.45-3.39 (1H, m), 2.65-2.59 (2H, m), 2.21-1.29 (19H, m), 1.36 (3H, s), 1.32-0.88 (9H, m), 0.86 (3H, s), 0.81 (3H, s). ¹³C NMR (CDCl₃, 100 MHz) δ: 142.6, 128.4, 128.3, 125.7, 75.1, 71.2, 69.5, 58.0, 56.3, 53.7, 51.7, 45.7, 42.9, 41.5, 40.2, 37.3, 36.3, 33.7, 32.3, 31.0, 30.7, 26.3, 23.7, 22.4, 21.0, 13.8, 13.5.

Synthesis Example 15

Oxy20

(3S,8S,9S,10R,13S,14S)-17-((S,E)-2-hydroxy-6-methylhept-3-en-2-yl)-10,13-dimethyl-2,3,4,7,8,9,10,11,12,13,14,15,16,17-tetradecahydro-1H-cyclopenta[a]phenanthren-3-ol, [Oxy20]

The stereoselective synthesis of the compound Oxy20 was carried out according to published procedures (72). The silylated pregnenolone was subjected to stereoselective addition of the anion of 4-methyl-1-pentyne formed by reaction of the acetylene with n-butyllithium to provide the propargylic alcohol in 84% yield. Hydrogenation of the resulted propargylic alcohol in the presence of Lindlar catalyst gave a mixture of the (Z)- and (E)-allylic alcohols (90:10). Both isomers were separated chromatographically to afford the (Z)-isomer in 68% yield and the (E)-isomer in 7% yield. The minor (E)-isomer (100 mg, 0.19 mmol) was desilylated in the presence of tetrabutylammonium fluoride in THF (0.8 mL, 0.8 mmol) to give the corresponding diol Oxy20 (70 mg, 89%) as a white powder.

[Oxy20]

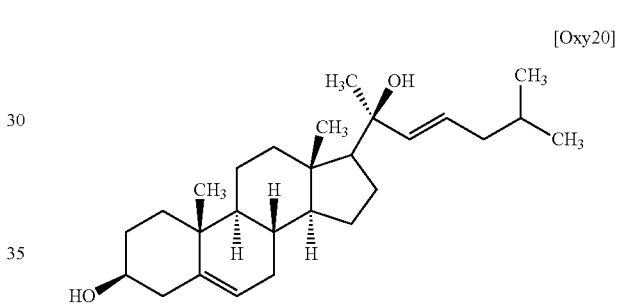

¹H NMR (CDCl₃; 400 MHz) δ: 5.56 (1H, d, J=15.5 Hz), 5.51 (1H, dt, J=15.5, 6.5 Hz), 5.35-5.33 (1H, m), 3.55-3.47 (1H, m), 2.28-1.81 (6H, m), 1.66-1.38 (13H, m), 1.32 (3H, s), 1.23-1.07 (4H, m), 1.00 (3H, s), 0.98-0.90 (2H, m), 0.87 (6H, d, J=6.6 Hz), 0.82 (3H, s). ¹³C NMR (CDCl₃, 100 MHz) δ: 140.8, 139.1, 125.0, 121.6, 75.4, 71.8, 59.9, 56.8, 50.1, 42.8, 42.3, 41.7, 40.2, 37.2, 36.5, 31.8, 31.7, 31.3, 29.2, 28.5, 23.9, 23.3, 22.4, 22.3, 20.9, 19.4, 13.8.

Aspects of Bioactive/Pharmaceutical Compositions

Formulations or compositions suitable for oral administration can consist of liquid solutions, such as an effective amount of an oxysterol dissolved in diluents, such as water, saline, or fruit juice; capsules, sachets or tablets, each containing a predetermined amount of the active ingredient, as solid, granules or freeze-dried cells; solutions or suspensions in an aqueous liquid; and oil-in-water emulsions or water-in-oil emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Suitable formulations for oral delivery can also be incorporated into synthetic and natural polymeric microspheres, or other means to protect the agents of the present invention from degradation within the gastrointestinal tract.

Formulations suitable for parenteral administration (e.g., intravenous) include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (i.e., lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The oysterols of the present disclosure, alone or in combination with other therapeutic agents, can be made into aerosol formulations to be administered via inhalation. These aerosol formulations can be placed into pressurized acceptable propellants, such as dichlorodifluoromethane, propane, nitrogen, and the like.

Oxysterols, alone or in combination with other therapeutic agents, can also be made into suitable formulations for transdermal application and absorption. Transdermal electroporation or iontophoresis also can be used to promote and/or control the systemic delivery of the agents and/or pharmaceutical compositions of the present invention through the skin (73).

Suitable formulations for topical administration include lozenges comprising the active ingredient in a flavor, usually sucrose and acacia or tragacanth; pastilles comprising the active ingredient in an inert base, such as gelatin and glycerin, or sucrose and acacia; mouthwashes comprising the active ingredient in a suitable liquid carrier; or creams, emulsions, suspensions, solutions, gels, creams, pastes, foams, lubricants, sprays, suppositories, or the like.

A person skilled in the art will appreciate that a suitable or appropriate formulation can be selected, adapted or developed based upon the particular application at hand. In addition, the pharmaceutical compositions of the present invention may be prepared for administration by a variety of different routes, whether systemic, local, or both. Such examples, include, but are not limited to, administrations performed intraarticularly, intracranially, intradermally, intrahepatically, intramuscularly, intraocularly, intraperitoneally, intrathecally, intravenously, subcutaneously, transdermally, or directly into a atherosclerotic site, such as by direct injection, direct application, and/or by implanting a device into in an artery or other appropriate tissue site.

An oxysterol may be formulated to be contained within, or, adapted to release by a surgical or medical device or implant. In certain aspects, an implant may be coated or otherwise treated with an oxysterol. For example, hydrogels, or other polymers, such as biocompatible and/or biodegradable polymers, may be used to coat an implant with the compositions of the present invention (i.e., the composition may be adapted for use with a medical device by using a hydrogel or other polymer). Polymers and copolymers for coating medical devices with an agent are well-known in the art. Examples of implants include, but are not limited to, angioplasty balloons, stents, drug-eluting stents, sutures, prosthesis, vascular catheters, dialysis catheters, vascular grafts, prosthetic heart valves, cardiac pacemakers, implantable cardioverter defibrillators or IV needles. Merely by way of example, a stent or stent graft typically includes a slender fabric tubular graft portion and is normally used to reinforce or strengthen a weak spot in a body passageway, such as a blood vessel. Insertion of a stent graft may be performed by use of a catheter. Placement may be facilitated by balloon expansion, such as during or following a balloon angioplasty procedure, or, alternatively, the stent graft may be self expanding.

Dosages for oxysterols of the invention can be in unit dosage form, such as a tablet or capsule. The term "unit dosage form," as used herein, refers to physically discrete units suitable as unitary dosages for animal (e.g., human) subjects, each unit containing a predetermined quantity of an agent of the invention, alone or in combination with other therapeutic agents, calculated in an amount sufficient to produce the desired effect in association with a pharmaceutically acceptable diluent, carrier, or vehicle.

One skilled in the art can routinely determine the appropriate dose, schedule, and method of administration for the exact formulation of the composition being used, in order to achieve the desired effective amount or effective concentration of the agent in the individual patient. One skilled in the art also can readily determine and use an appropriate indicator of the "effective concentration" of the compounds, for example, the oxysterols, of the present invention by a direct or indirect analysis of appropriate patient samples (e.g., blood and/or tissues), in addition to analyzing the appropriate clinical symptoms of the disease, disorder, or condition.

The dose of an oxysterol, or composition thereof, administered to an animal or mammal, particularly a human, in the context of the present invention should be sufficient to effect at least a therapeutic response in the individual over a reasonable time frame. The exact amount of the dose will vary from subject to subject, depending on the species, age, weight and general condition of the subject, the severity or mechanism of any disorder being treated, the particular agent or vehicle used, its mode of administration and the like. The dose used to achieve a desired concentration in vivo will be determined by the potency of the particular oxysterol employed, the pharmacodynamics associated with the oxysterol in the host, with or without additional agents, the severity of the disease state of infected individuals, as well as, in the case of systemic administration, the body weight and age of the individual. The size of the dose may also be determined by the existence of any adverse side effects that may accompany the particular agent, or composition thereof, employed. It is generally desirable, whenever possible, to keep adverse side effects to a minimum.

For example, a dose can be administered in the range of from about 5 ng (nanograms) to about 1000 mg (milligrams), or from about 100 ng to about 600 mg, or from about 1 mg to about 500 mg, or from about 20 mg to about 400 mg. For example, the dose can be selected to achieve a dose to body weight ratio of from about 0.0001 mg/kg to about 1500 mg/kg, or from about 1 mg/kg to about 1000 mg/kg, or from about 5 mg/kg to about 150 mg/kg, or from about 20 mg/kg to about 100 mg/kg. For example, a dosage unit can be in the range of from about 1 ng to about 5000 mg, or from about 5 ng to about 1000 mg, or from about 100 ng to about 600 mg, or from about 1 mg to about 500 mg, or from about 20 mg to about 400 mg, or from about 40 mg to about 200 mg of a compound according to the present invention.

A dose can be administered once per day, twice per day, four times per day, or more than four times per day as required to elicit a desired therapeutic effect. For example, a dose administration regimen can be selected to achieve a blood serum concentration of a compound of the present invention in the range of from about 0.01 to about 1000 nM, or from about 0.1 to about 750 nM, or from about 1 to about 500 nM, or from about 20 to about 500 nM, or from about 100 to about 500 nM, or from about 200 to about 400 nM. For example, a dose administration regime can be selected to achieve an average blood serum concentration with a half maximum dose of a compound of the present invention in the range of from about 1 µg/L (microgram per liter) to about 2000 µg/L, or from about 2 µg/L to about 1000 µg/L, or from about 5 µg/L to about 500 µg/L, or from about 10 µg/L to about 400 µg/L, or from about 20 µg/L to about 200 µg/L, or from about 40 µg/L to about 100 µg/L.

A therapeutically effective dose of an oxysterol as described herein may include one which has a positive clinical effect on a patient as measured by the ability of the agent to improve atherosclerosis, or other related cardiovascular diseases or conditions. A therapeutically effective dose of an oxysterol may also include one which has a positive clinical effect on reducing the risk of developing atherosclerosis, or other related conditions. The therapeutically effective dose of each agent can be modulated to achieve the desired clinical effect, while minimizing negative side effects. The dosage of the agent may be selected for an individual patient depending upon the route of administration, severity of the disease, age and weight of the patient, other medications the patient is taking and other factors normally considered by an attending physician, when determining an individual regimen and dose level appropriate for a particular patient.

By way of example, the invention may include elevating endogenous, circulating oxysterol levels over the patient's basal level. In a normal adult levels are about 10-400 ng/ml depending on age and type of oxysterol, as measured by mass spectrometry. Those skilled in the art of pharmacology would be able to select a dose and monitor the same to determine if an increase circulating levels over basal levels has occurred.

When given in combined therapy, the other agent can be given at the same time as the oxysterol, or the dosing can be staggered as desired. The two (or more) drugs also can be combined in a composition. Doses of each can be less when used in combination than when either is used alone. Certain embodiments may also include treatment with an additional agent which acts independently or synergistically with an oxysterol to improve vascular condition.

Oxysterols may also be administered to cells and tissues and subjects at risk of atherosclerosis, in dosages and by routes effective to reduce, eliminate, prevent, or treat atherosclerotic lesions. Another embodiment of the invention is a kit useful for any of the methods disclosed herein, either in vitro or in vivo. Such a kit can comprise one or more of the oxysterols or pharmaceutical compositions discussed herein. Optionally, the kits comprise instructions for performing the method. Optional elements of a kit of the invention include suitable buffers, pharmaceutically acceptable carriers, or the like, containers, or packaging materials. The reagents of the kit may be in containers in which the reagents are stable, e.g., in lyophilized form or stabilized liquids. The reagents may also be in single use form, e.g., in single dosage form. A skilled worker will recognize components of kits suitable for carrying out any of the methods of the invention.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

REFERENCES

1. Caplan A I. 1994. The mesengenic process. Clin. Plast Surg 21: 429-435.
2. Majors A K, Boehm C A, Nitto H, Midura R J, Muschler G F. 1997. Characterization of human bone marrow stromal cells with respect to osteoblastic differentiation. J Orthop Res 15:546-557.
3. Prockop D J. 1997. Marrow stromal cells as stem cells for nonhematopoietic tissues. Science 276:71-74.
4. Vaananen H K. 2005. Mesenchymal stem cells. Ann Med 37:469-479.
5. Pittenger M F, Mackay A M, Beck S C, Jaiswal R K, Douglas R, Mosca J D, Moorman M A, Simonetti D W, Craig S, Marshak D R. 1999. Multilineage potential of adult human mesenchymal stem cells. Science 284:143-147.
6. Riggs B L, Melton L J. 1992. The prevention and treatment of osteoporosis. N Engl J Med 327:620-627.
7. Cummings S R, Melton L J. 2002. Epidemiology and outcomes of osteoporotic fractures. Lancet 359: 1761-1767.
8. Rodan G A, Martin T J. 2000. Therapeutic approaches to bone diseases. Science 289:1508-1514.
9. Goltzman D. 2002. Discoveries, drugs and skeletal disorders. Nat Rev Drug Discov 1:784-796.
10. Mundy G R. 2002. Directions of drug discovery in osteoporosis. Annu Rev Med 53:337-354.
11. Schroepfer G J. 2000. Oxysterols: Modulators of cholesterol metabolism and other processes. Phyiol Rev 80:361-554.
12. Bjorkhem I, Dicsfalusy U. 2002. Oxysterols: Friends, foes, or just fellow passengers? Arterioscler Thromb Vasc Biol 22:734-742.
13. Kha H T, Basseri B, Shouhed D, Richardson J, Tetradis S, Hahn T J, Parhami F. 2004. Oxysterols regulate differentiation of mesenchymal stem cells: Pro-bone and anti-fat. J Bone Miner Res 19:830-840.
14. Richardson J A, Amantea C M, Kianmand B, Tetradis S, Lieberman J R, Hahn T J, Parhami F. 2007. Oxysterol-induced osteoblastic differentiation of pluripotent mesenchymal cells is mediated through a PKC- and PICA-dependent pathway. J Cell Biochem 100:1131-1145.
15. Dwyer J R, Sever N, Carlson M, Nelson S F, Beachy P A, Parhami F. 2007. Oxysterols are novel activators of the hedgehog signaling pathway in pluripotent mesenchymal cells. J Biol Chem 282: 8959-8968.
16. Kim W K, Meliton V, Amantea C M, Hahn T J, Parhami F. 2007. 20(S)-hydroxycholesterol inhibits PPARgamma expression and adipogenic differentiation of bone marrow stromal cells through a hedgehog-dependent mechanism. J Bone Miner Res 22:1711-1719.
17. Gordon M D, Nusse R. 2006. Wnt signaling: multiple pathways, multiple receptors, and multiple transcription factors. J Biol Chem 281:22429-22433.
18. Clevers H. 2006. Wnt/β-catenin signaling in development and disease. Cell 127:469-480.
19. Willert K, Jones K A. 2006. Wnt signaling: is the party in the nucleus? Genes Dev 20:1394-1404.
20. Johnson M L, Harnish K, Nusse R, Van Hul W. 2004. LRP5 and Wnt signaling: a union made for bone. J Bone Miner Res 19:1749-1757.
21. Gaur T, Lengner C J, Hovhannisyan H, Bhat R A, Bodine P V N, Komm B S, Javed A, Van Wijnen A J, Stein J L, Stein G S, Lian J B. 2005. Canonical Wnt signaling promotes osteogenesis by directly stimulating Runx2 gene expression. J Biol Chem 280:33132-33140.
22. Westendorf J J, Kahler R A, Schroeder T M. 2004. Wnt signaling in osteoblast and bone diseases. Gene 341:19-39.
23. Bennett C N, Ross S E, Longo K A, Bajnok L, Hemati N, Johnson K W, Harrison S D, MacDougald O A. 2002. Regulation of Wnt signaling during adipogenesis. J Biol Chem 277:30998-31004.
24. Kennell J A, MacDougald O A. 2005. Wnt signaling inhibits adipogenesis through β-catenin-dependent and -independent mechanisms. J Biol Chem 280:24004-24010.
25. Gong Y, Slee R B, Fukai N, Rawadi G, Roman-Roman S, Reginato A M, Wang H, Cundy T, Glorieux F H, et al. 2001. LDL receptor-related protein 5 (LRP5) affects bone accrual and eye development. Cell 107:513-523.
26. Boyden L M, Mao J, Belsky J, Mitzner L, Farhi A, Mitnick M A, Wu D, Insogna K, Lifton R P. 2004. N Engl J Med 364: 1513-1521.
27. Bafico A, Liu G, Yaniv A, Gazit A, Aaronson S A. 2001. Novel mechanism of Wnt signalling inhibition mediated by Dickkopf-1 interaction with LRP6/Arrow. Nature Cell Biol 3:683-686.
28. Peng S, Miao C, Li J, Fan X, Cao Y, Duan E. 2006. Dickkopf-1 induced apoptosis in human placental choriocarcinoma is independent of canonical Wnt signaling. Biochem Biophysic Res Comm 350:641-647.
29. Lee A Y, He B, You L, Xu Z, Mazieres J, Reguart N, Mikami I, Batra S, Jablons D M. 2004. Dickkopf-1 antagonizes Wnt signaling independent of β-catenin in human mesothelioma. Biochem Biophysic Res Comm 323:1246-1250.
30. Hu H, Thlton M J, Tu X, Yu K, Ornitz D M, Long F. 2004. Sequential roles of Hedgehog and Wnt signaling in osteoblast development. Development 132:49-60.
31. Silva-Vargas V, Lo Celso C, Giangreco A, Ofstad T, Prowse D M, Braun K M, Watt F M. 2005. β-catenin and hedgehog signal strength can specify number and location of hair follicles in adult epidermis without recruitment of bulge stem cells. Develop Cell 9:121-131.
32. Mullor J L, Dahmane N, Sun T, Altaba A R. 2001. Wnt signals are targets and mediators of Gli function. Current Biol 11:769-773.
33. Taipale J, Beachy P A. 2001. The hedgehog and Wnt signalling pathways in cancer. Nature 411:349-354.
34. Debiais F, Lefevre G, Lemonnier J, Le Mee S, Lasmoles F, Mascarelli F, Marie P J. 2004. Fibroblast growth factor-2 induces osteoblast survival through a phosphatidylinositol 3-kinase-dependent, -β-catenin-independent signaling pathway. Experimental Cell Res 297: 235-246.
35. Almeida M. Han L, Bellido T, Manolagas S C, Kousteni S. 2005. Wnt proteins prevent apoptosis of both uncommitted osteoblast progenitors and differentiated osteoblasts by β-catenin-dependent and -independent signaling cascades involving Src/ERK and Phosphatidylinositol 3-kinase/Akt. J Biol Chem 280:41342-41351.
36. Fujita T, Azuma Y, Fukuyama R, Hattori Y, Yoshida C, Koida M, Ogita K, Komori T. 2004. Runx2 induces osteoblast and chondrocyte differentiation and enhances their migration by coupling with PI3K-Akt signaling. J Cell Biol 166:85-95.
37. Ghosh-Choudhury N, Abboud S L, Nishimura R, Celeste A, Mahimainathan L, Choudhurry G G. 2002. Requirement of BMP-2-induced phosphatidylinositol 3-kinase and Akt serine/threonine kinase in osteoblast differentiation and Smad-dependent BMP-2 gene transcription. J Biol Chem 277:33361-33368.
38. Ghosh-Choudhury N, Mandal C C, Choudhurry G G. 2007. Statin-induced Ras activation integrates the phosphatidylinositol 3-kinase signal to Akt and MAPK for bone morphogenetic protein-2 expression in osteoblast differentiation. J Biol Chem 282:4983-4993.
39. Peng X, Xu P, Chen M, Hahn-Windgassen A, Skeen J, Jacobs J, Sundararajan D, Chen W S, Crawford S E, Coleman K G, Hay N. 2007. Dwarfism, impaired skin development, skeletal muscle atrophy, delayed bone development, and impeded adipogenesis in mice lacking Akt1 and Akt2. Genes Dev 17:1352-1365.
40. Liu X, Bruxvoort K J, Zylstra C R, Liu J, Cichowski R, Faugere M C, Bouxsein M L, Wan C, Williams B O, Clemens T L. 2007. Lifelong accumulation of bone in mice lacking Pten in osteoblasts. Proc Natl Acad Sci 104: 2259-2264.
41. Riobo N A, Lu K, Ai X, Haines G M, Emerson C P. 2006. Phosphoinositide 3-kinase and Akt are essential for Sonic Hedgehog signaling. Proc Natl Acad Sci 103:4505-4510,
42. Kenney A M, Widlund H R, Rowitch D H. 2003. Hedgehog and PI-3 kinase signaling converge on Nmycl to promote cell cycle progression in cerebellar neuronal precursors. Development 131:217-228.
43. Fu J, Liu W, Zhou J, Sun H, Xu H, Luo L, Zhang H, Zhou Y. 2006. Sonic hedgehog protein promotes bone marrow-derived endothelial progenitor cell proliferation, migration and VEGF production by PI 3-kinase/Akt signaling pathways. Acta Pharmacol Sinica 27:685-693.
44. Kanda S. Mochizuki Y, Suematsu T, Miyata Y, Nomata K, Kanetake H. 2003. Sonic hedgehog induces capillary morphogenesis by endothelial cells through phosphoinositide 3-kinase. J Biol Chem 278:8244-8249.
45. Parhami F, Morrow A D, Balucan J, Leitinger N, Watson A D, Tintut Y, Berliner J A, Demer L L. 1997. Lipid oxidation products have opposite effects on calcifying vascular cell and bone cell differentiation. Arterioscl Thromb Vasc Biol 17:680-687.
46. Parhami F, Jackson S M, Tintut Y, Le V, Balucan J P, Territo M, Demer L L. 1999. Atherogenic diet and minimally oxidized low density lipoprotein inhibit osteogenic and promote adipogenic differentiation of marrow stromal cells. J Bone Miner Res 14:2067-2078.
47. Smith E, Frenkel B. 2005. Glucocorticoids inhibit the transcriptional activity of LEF/TCF in differentiating osteoblasts in a glycogen synthase kinase-3β-dependent and -independent manner. J Biol Chem 280:2388-2394.
48. Tetsu O, McCormick F. 1999. β-Catenin regulates expression of cyclin D1 in colon carcinoma cells. Nature 398:422-426.
49. Jho E, Zhang T, Domon C, Joo C, Freund J, Costantini F. 2002. Wnt/β-catenin/Tcf signaling induces the transcription of Axin2, a negative regulator of the signaling pathway. Mol Cell Biol 22:1172-1183.
50. Wharton K A, Zimmermann G, Rousset R, Scott M P. 2001. Vertebrate proteins related to drosophila Naked Cuticle bind Dishevelled and antagonize Wnt signaling. Develop Biol 234: 93-106.
51. Van Raay T J, Coffey R J, Solnica-Krezel L. 2007. Zebrafish Naked1 and Naked2 antagonize both canonical and non-canonical Wnt signaling. Develop Biol 309:151-168.
52. Reguart N, He B, Xu Z, You L, Lee A Y, Mazieres J, Mikami I, Batra S, Rosell R, McCormick F, Jablons D M.

2004. Cloning and characterization of the promoter of human Wnt inhibitory factor-1. Biochem Biophys Res Comm 323:229-234.
53. Mbalaviele G, Sheikh S, Stains J P, Salazar V S, Cheng S, Chen D, Civitelli R. 2005. β-Catenin and BMP-2 synergize to promote osteoblast differentiation and new bone formation. Cell Biochem 94:403-418.
54. Rawadi G, Vayssiere B, Dunn F, Baron R, Roman-Roman S. 2003. BMP-2 controls alkaline phosphatase expression and osteoblast mineralization by a Wnt autocrine loop. J Bone Miner Res 18:1842-1853.
55. Kim S, Lee W, Choi K. 2007. The PI3 kinase-Akt pathway mediates Wnt3a-induced proliferation. Cell Signal 19:511-518.
56. Schambony A, Wedlich D. 2007. Wnt-5A/Ror2 regulate expression of XPAPC through an alternative noncanonical signaling pathway. Develop Cell 12:779-792.
57. Boland G M, Perkins G, Hall D J, Tuan R S. 2004. Wnt3a promotes proliferation and suppresses osteogenic differentiation of adult human mesenchymal stem cells. J Cell Biochem 93:1210-1230.
58. Bennett C N, Longo K A, Wright W S, Suva L J, Lane T F, Hankenson K D, MacDougald O A. 2005. Regulation of osteoblastogenesis and bone mass by Wnt10b. Proc Natl Acad Sci 102: 3324-3329.
59. Day T F, Guo X, Garrett-Beal L, Yang Y. 2005. Wnt/β-catenin signaling in mesenchymal progenitors controls osteoblast and chondrocyte differentiation during vertebrate skeletogenesis. Develop Cell 8:739-750.
60. Hill T P, Spater D, Taketo M M, Birchmeier W, Hartmann C. 2005. Canonical Wnt/β-catenin signaling prevents osteoblasts from differentiating into chondrocytes. Develop Cell 8: 727-738.
61. Clement-Lacroix P, Ai M, Morvan F, Roman-Roman S, Vayssiere B, Belleville C, Estrera K, Warman M L, Baron R, and Rawadi G. 2005. LrpS-independent activation of Wnt signaling by lithium chloride increases bone formation and bone mass in mice. Proc Natl Acad Sci 102: 17404-17411.
62. Rodda S J, McMahon A P. 2006. Distinct roles for Hedgehog and canonical Wnt signaling in specification, differentiation, and maintenance of osteoblast progenitors. Development 133: 3231-3244.
63. Cohen (2003) *Am J Med Gen* 123A, 5-28; Mullor et al. (2002) *Trends Cell Bio* 12, 562-569.
64. Velgova, H Cerny, Vaclav; Sorm, Frantisek; Slama, Karel. Steroids. CXXVI. Further compounds with anti-sclerotization effect on *Pyrrhocoris apterus* larvae; structure and activity correlations. Collection of Czechoslovak Chemical Communications (1969), 34(11), 3354-76.
67. Sheikh, Younus M.; Djerassi, Carl. Mass spectrometry in structural and stereochemical problems. CCXXX. Preparation of 5α,20α and 5α,17α,20α-cholestane-3β,6α-diol. Electron impact induced fragmentation of steroidal Δ 17(20), Δ 20(21) and Δ 20(22) olefins. Journal of Organic Chemistry (1973), 38(20), 3545-53.
66. Drew, J.; Letellier, M.; Morand, P.; Szabo, A. G. *J Org. Chem.* 1987, 52, 4047-4052.
67. Burger, A; Colobert, F.; Hetru, C.; Luu, B. *Tetrahedron* 1988, 44, 1141-1152.
68. De la Rosa, M. A.; Velarde, E.; Guzman, A. *Synth. Commun.* 1990, 20, 2059-2064.
69. (a) Parhami, F.; Jung, M. E.; Dwyer, J. R.; Nyuyen, K. "Preparation of oxysterol compounds that stimulate the hedgehog pathway for treatment of various disorders," PCT Int. Appl. 2007, 83 pp. (b) Honda, T.; Katoh, M.; Yamane, S. J. *Chem. Soc., Perkin Trans.* 1, 1996, 2291-2296.
70. (a) Cadot, C.; Poirier, D.; Philip, A. *Tetrahedron* 2006, 62, 4384-4392. (b) Kametani, T.; Tsubuki, M.; Higurashi, K.; Honda, T. *J Org. Chem.* 1986, 51, 2932-2939. (c) Poza, J.; Rega, M.; Paz, V.; Alonso, B.; Rodriguez, J.; Salvador, N.; Fernandez, A.; Jimene-z, C. *Bioorg. Med. Chem.* 2007, 15, 4722-4740.
71. (a) Bunta, W.; Yoshiaki, N.; Takehiko, O.; Hisashi, M. *Steroids* 2004, 69, 483-493. (b) Velgova, H.; Cerny, V.; Sorm, F.; Slama, K. *Collect. Czech. Chem. Commun.* 1969, 34, 3354-3375.
72. Watanabe, B.; Nakagawa, Y.; Ogura, T.; Miyagawa, H. *Steroids* 2004, 69, 483-493.
73. Theiss et al. (1991), *Meth. Find. Exp. Clin. Pharmacol.* 13: 353-359.
74. Aghaloo T, Amantea C, Cowan C, Richardson J, Wu B, Parhami F, Tetradis S. Oxysterols enhance osteoblast differentiation in vitro and bone healing in vivo. *J Orthop Res* 25:1488-1497; 2007.

---

We claim:

1. A compound having Formula I,

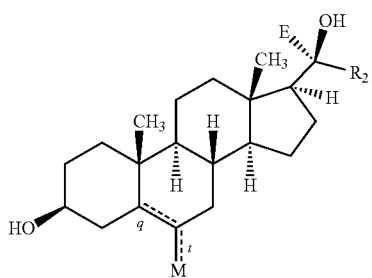

(Formula I)

wherein q is a single bond or a double bond,
wherein t is a single bond,
wherein at least one of q and t is a single bond,
wherein M is selected from the group consisting of hydrogen (—H), hydroxy (—OH), formoxy (—O(C=O)H), acyloxy (—O(C=O)—$C_{1-6}$alkyl), alkoxy (—O—$C_{1-6}$alkyl), sulfhydryl (—SH), alkylthio (—S—$C_{1-6}$alkyl), amino (—$NH_2$), methylamino (—$NHCH_3$), alkylamino (—NH—$C_{1-6}$alkyl), formamido (—NH(C=O)H), acetamido (—NH(C=O)$CH_3$), and alkylamido (—NH(C=O)—$C_{1-6}$alkyl),
wherein E is $C_{1-6}$ alkyl,
wherein $R_2$ is selected from the group consisting of $C_{2-6}$ alkyl, $C_{2-6}$ alkenys, $C_{8-12}$ phenalkyl, thiophene-substituted $C_{5-11}$ alkyl, $C_{5-12}$ aralkenyl, $C_{5-12}$ aralkynyl, halogen-substituted $C_{4-12}$ aralkyl, halogen-substituted $C_{5-12}$ aralkenyl halogen-substituted $C_{5-12}$ aralkynyl, alkyl-substituted $C_{5-18}$ aralkyl alkyl-substituted $C_{6-18}$ aralkenyl, alkyl-substituted $C_{6-18}$ aralkynyl, hydroxy-substituted $C_6$ alkyl, and hydroxy-substituted $C_{2-6}$ alkenyl,
wherein when q is a single bond, M is hydroxy, and E is methyl, then $R_2$ is not 4-methylpentyl vinyl, 1-hydroxzy-4-methylpentyl, 3-hydroxy-3-methylbutyl, 4-hydroxy-4methylpentyl 1,4-dihydroxy-4-methylpentyl, 1,5-dihydroxy-4-methylpentyl, or 2-phenylethenyl, wherein when q is a single bond, M is hydroxy, and E is methyl, then $R_2$ is not 4-methylpentyl or 4-methylpent-3-enyl, wherein when q is a double bond, M is hydrogen, and E is methyl, then $R_2$ is not ethyl, vinyl, n-propyl, allyl, 1-propenyl, n-butyl, t-butyl, 1-methylpropyl, n-pentyl, 3-methylbutyl, 3-methylpentyl, 4-methylpentyl, 4-methylpent-3-enyl, 4-methylpent-4-enyl, 1-hydroxy-4-methylpentyl, 4-hydroxy-4-methylpentyl, 4-hydroxy-4-methylpent-1-enyl, 4-hydroxy-4-methylpent-2-enyl, 1,4-dihydroxy-4-methylpentyl, 1-(2-pyridinyl) ethyl, or 3-methyl-4-hydroxybutyl, wherein when q is a double bond, M is hydrogen, and E is 4-methylpentyl, then $R_2$ is not hydroxymethyl, wherein when q is a double bond and M is hydrogen, then $R_2$ is not methyl-substituted benzyl, wherein the compound is not

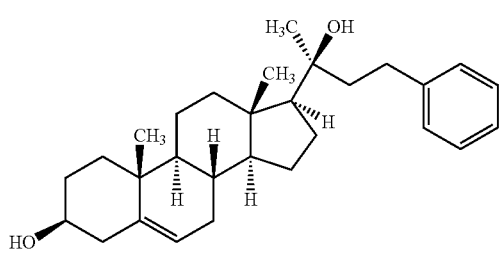

[Oxy27]

and wherein the compound is inductive of a biological response in a mammalian cell, the response selected from the group consisting of stimulated osteoblastic differentiation, inhibited adipocyte differentiation, stimulated cartilage formation, stimulated hair growth, and/or stimulated angiogenesis.

2. The compound of claim 1, wherein the compound is selected from the group consisting of

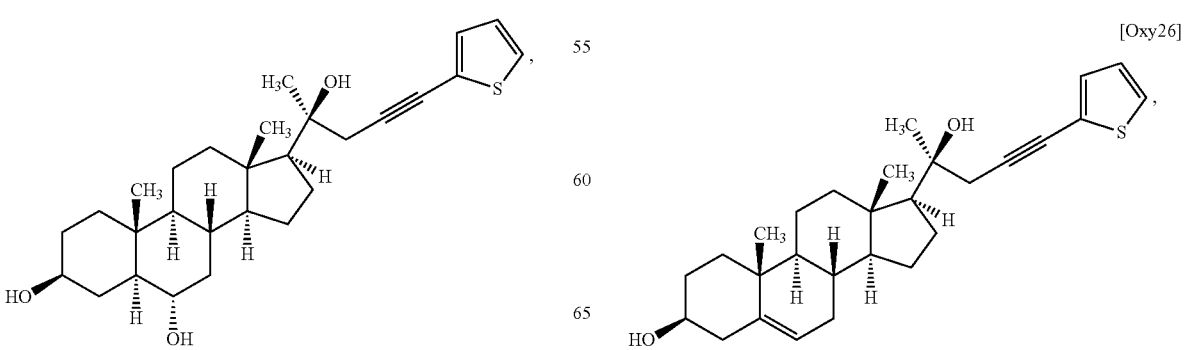

[Oxy51]

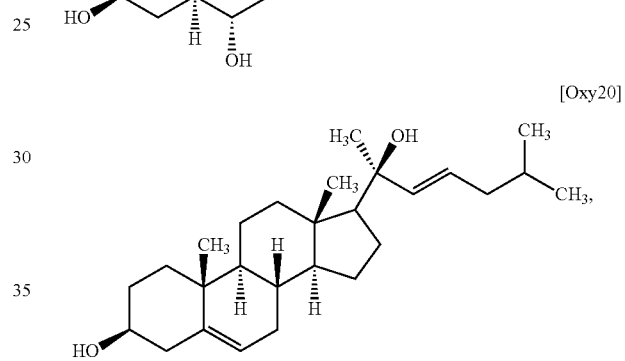

[Oxy52]

[Oxy53]

[Oxy20]

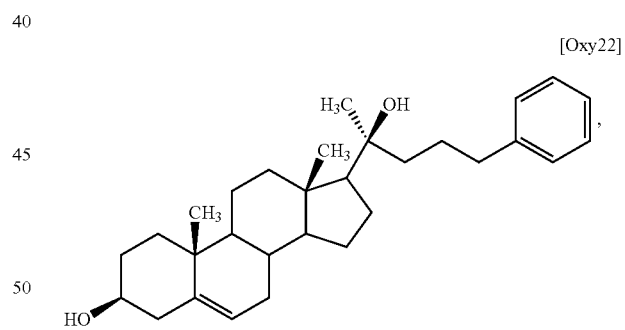

[Oxy22]

[Oxy26]

[Oxy39]

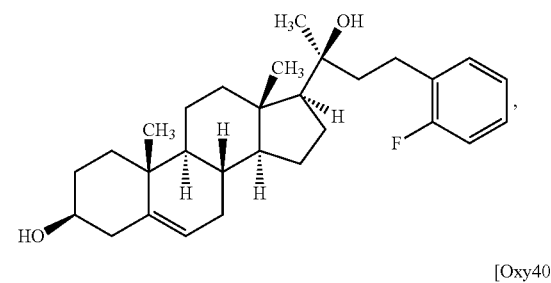

[Oxy40]

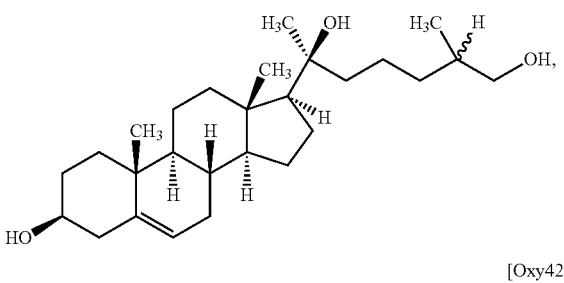

[Oxy42]

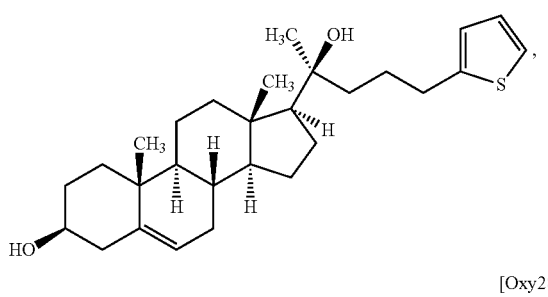

[Oxy28]

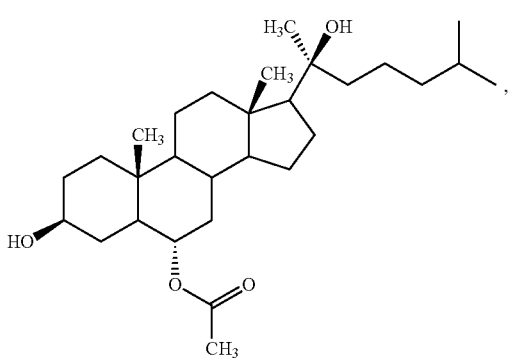

[Oxy41]

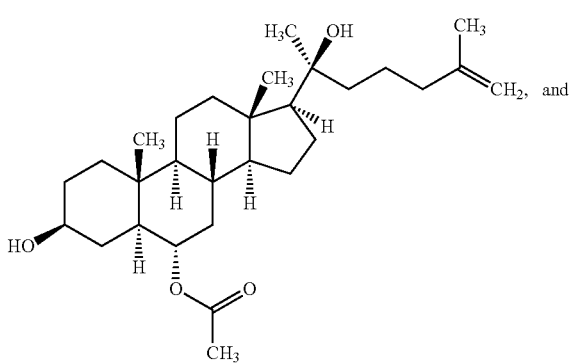, and

[Oxy48]

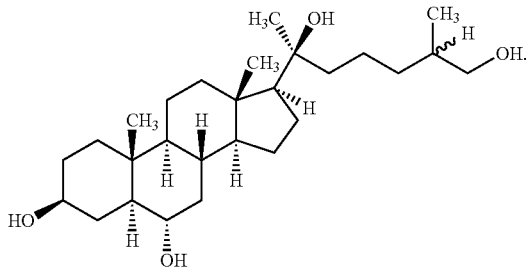

3. A bioactive composition comprising a compound of claim 1 and a pharmaceutically acceptable carrier.

4. The bioactive composition of claim 3, further comprising at least one additional agent, selected from the group consisting of parathyroid hormone, sodium fluoride, insulin-like growth factor I (ILGF-I), insulin-like growth factor II (ILGF-II), transforming growth factor beta (TGF-β), a cytochrome P450 inhibitor, an osteogenic prostanoid, bone morphogenetic protein 2 (BMP 2), bone morphogenetic protein 4 (BMP 4), bone morphogenetic protein 7 (BMP 7), and bone morphogenetic protein 14 (BMP 14).

5. The compound of claim 1, wherein q is a single bond.

6. The compound of claim 5, wherein E is —CH$_3$.

7. The compound of claim 6, wherein M is —OH or —O(C═O)CH$_3$.

8. The compound of claim 7, wherein R$_2$ is selected from the group consisting of C$_{2-6}$ alkyl, C$_{2-6}$ alkenyl, C$_{8-12}$ phenalkyl, thiophene-substituted C$_{5-11}$ alkyl, C$_{5-12}$ aralkynyl, and hydroxy-substituted C$_6$ alkyl.

9. The compound of claim 8, wherein the compound is

[Oxy50]

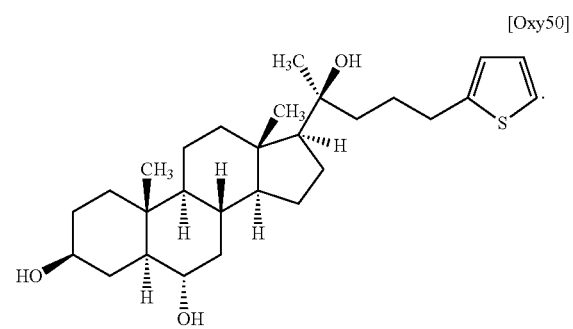

10. The compound of claim 8, wherein the compound is

[Oxy49]

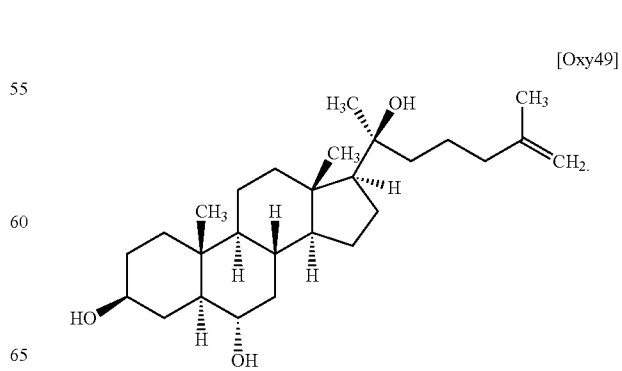

11. The compound of claim 1, wherein q is a double bond.

12. The compound of claim 11, wherein E is —$CH_3$.

13. The compound of claim 12, wherein M is hydrogen.

14. The compound of claim 13, wherein $R_2$ is selected from the group consisting of $C_{2-6}$ alkenyl, $C_{8-12}$ phenalkyl, thiophene-substituted $C_{5-11}$ alkyl, $C_{5-12}$ aralkynyl, and halogen-substituted $C_{4-12}$ aralkyl.

* * * * *